US008765733B2

(12) United States Patent
Frank et al.

(10) Patent No.: US 8,765,733 B2
(45) Date of Patent: Jul. 1, 2014

(54) AMINE SUBSTITUTED METHANESULFONAMIDE DERIVATIVES AS VANILLOID RECEPTOR LIGANDS

(71) Applicant: Gruenenthal GmbH, Aachen (DE)

(72) Inventors: Robert Frank, Aachen (DE); Gregor Bahrenberg, Monschau-Konzen (DE); Thomas Christoph, Aachen (DE); Bernhard Lesch, Aachen (DE); Jeewoo Lee, Seoul (KR)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/626,282

(22) Filed: Sep. 25, 2012

(65) Prior Publication Data

US 2013/0079320 A1   Mar. 28, 2013

Related U.S. Application Data

(60) Provisional application No. 61/539,170, filed on Sep. 26, 2011.

(30) Foreign Application Priority Data

Sep. 26, 2011  (EP) ..................................... 11007805

(51) Int. Cl.
*A61K 31/00* (2006.01)
*C07D 211/68* (2006.01)
(52) U.S. Cl.
USPC ...... 514/210.2; 514/318; 546/194; 546/276.4
(58) Field of Classification Search
USPC .................... 514/210.2, 318; 546/194, 276.4
See application file for complete search history.

(56) References Cited

U.S. PATENT DOCUMENTS 7,799,782 B2 * 9/2010 Munson et al. ............ 514/234.5
2007/0105861 A1 5/2007 Lee et al.

FOREIGN PATENT DOCUMENTS

| JP | 2005-314407 A | 11/2005 |
|---|---|---|
| WO | WO 2007/045462 A2 | 4/2007 |
| WO | WO 2007/045462 A3 | 6/2007 |
| WO | WO 2011/109441 A1 | 9/2011 |

OTHER PUBLICATIONS

European Search Report dated Dec. 13, 2011 (six (6) pages).
Bennett et al., "A Peripheral Mononeuropathy in Rat That Produces Disorders on Pain Sensation Like Those Seen in Man", 1988, Pain, vol. 33, pp. 87-107.
Kim et al., "An Experimental Model for Peripheral Neuropathy Produced by Segmental Spinal Nerve Ligation in the Rat", 1992, Pain, vol. 50, pp. 355-363.
D'Amour et al., "A Method for Determining Loss of Pain Sensation", The Biologic Research Laboratory, University of Denver, 1941, pp. 74-79.
DuBuisson et al., "The Formalin test: A Quantitative Study of the Analgesic Effects of Morphine, Meperidine, and Brain Stem Stimulation in Rats and Cats", 1977, Pain, vol. 4, pp. 161-174.
Smith et al., "March's Advanced Organic Chemistry: Reactions, Mechanisms, and Structure" 6th Edition—Table of Content (four (4) pages), 2007.
Carey et al. "Advanced Organic Chemistry—Part A:Structure and Mechanisms", 5th Edition (twenty-two (22) pages), 2007.
Carey et al., "Advanced Organic Chemistry—Part B: Reactions and Synthesis", 5th Edition (twenty-nine (29) pages), 2007.
Smith, "Compendium of Organic Synthetic Methods", A John Wiley & Sons Inc., 2009, Table of Content (fifteen (15) pages).
Cheng et al., "Relationship Between the Inhibition Constant ($K_1$) and the Concentration of Inhibitor Which Causes 50 Per Cent Inhibition ($I_{50}$) of and Enzymatic Reaction", Biochemical Pharmacology, 1973, vol. 22, pp. 3099-3108.
U.S. Appl. No. 13/626,329, filed Sep. 25, 2012.
U.S. Appl. No. 13/626,315, filed Sep. 25, 2012.
G. Ahern, Activation of TRPV1 by the Satiety Factor Oleoylethanolamide, The Journal of Biological Chemistry, vol. 278, No. 33, Aug. 15, 2003, pp. 30429-30434.
L.A. Birder et al., Altered urinary bladder function in mice lacking the vanilloid receptor TRPV1, Nature Neuroscience, vol. 5, No. 9, Sep. 2002, pp. 856-860.
E. Bodo et al., A Hot New Twist to Hair Biology: Involvement of Vanilloid Receptor-1 (VR1/TRPV1) Signaling in Human Hair Growth Control, American Journal of Pathology, vol. 166, No. 4, Apr. 2005, pp. 985-998.
D. Dawbarn et al., Intranigral Injection of Capsaicin Enhances Motor Activity and Depletes Nigral 5-Hydroxytryptamine But Not Substance P, Neuropharmacology, vol. 20, pp. 341-346, 1981.
P. Geppetti et al., Activation and sensitisation of the vanilloid receptor: role in gastrointestinal inflammation and function, British Journal of Pharmacology, 2004, vol. 141, No. 8, pp. 1313-1320.
J. Ghilardi et al., Selective Blockade of the Capasicin Receptor TRPV1 Attenuates Bone Cancer Pain, The Journal of Neuroscience, Mar. 23, 2005, vol. 25, No. 12, pp. 3126-3131.
P. Holzer, TRPV1 and the gut: from a tasty receptor for a painful vanilloid to a key player in hyperalgesia, European Journal of Pharmacology 500, 2004, pp. 231-241.
H. Rami et al., The therapeutic potential of TRPV1 (VR1) antagonists: clinical answers await, Drug Discover Today: Therapeutic Strategies, vol. 1, No. 1, 2004, pp. 97-104.
C. Maggi, Therapeutic Potential of Capsaicin-like Molecules: Studies in Animals and Humans, Life Sciences, vol. 51, 1992, pp. 1777-1781.
S. Marinelli et al., Presynaptic Facilitation of Glutamatergic Synapses to Dopaminergic Neurons of the Rat Substantia Nigra by Endogenous Stimulation of Vanilloid Receptors, The Journal of Neuroscience, Apr. 15, 2003, vol. 23, No. 8, pp. 3136-3144.
Pan et al., Sensing Tissue Ischemia: Another New Function for Capsaicin Receptors?, Circulation Journal of the American Heart Association, Circulation 2004, vol. 110, Issue 13, pp. 1826-1831.

(Continued)

Primary Examiner — Rei-tsang Shiao
(74) *Attorney, Agent, or Firm* — Crowell & Moring LLP

(57) ABSTRACT

The invention relates to amine substituted methanesulfonamide derivatives as vanilloid receptor ligands, to pharmaceutical compositions containing these compounds and also to these compounds for use in the treatment and/or prophylaxis of pain and further diseases and/or disorders.

23 Claims, No Drawings

(56) References Cited

OTHER PUBLICATIONS

H. Schultz, The spice of life is at the root of cardiac pain, Journal of Physiology (2003), 551.2, p. 400.

Y. Yiangou et al., Vanilloid receptor 1 immunoreactivity in inflamed human bowel, The Lancet, vol. 357, p. 1338-1339, Apr. 28, 2001.

M. Zahner et al., Cardiac vanilloid receptor 1-expressing afferent nerves and their role in the cardiogenic sympathetic reflex in rats, Journal of Physiology (2003) 551.2, pp. 515-523.

T. Sprenger et al., Migraine pathogenesis and state of pharmacological treatment options, BMC Medicine 2009, 7:71.

G.A. Lambert et al., The effects of the TRPV1 receptor antagonist SB-705498 on trigeminovascular sensitisation and neurotransmission, Nauyn-Schmied Arch Pharmacol (2009) vol. 380, pp. 311-325.

R. Planells-Cases et al., Functional aspects and mechanisms of TRPV1 involvement in neurogenic inflammation that leads to thermal hyperalgesia, Pflugers Arch—Eur J. Physiol (2005) vol. 451, pp. 151-159.

V. Micale et al., Altered responses of dopamine D3 receptor null mice to excitotoxic or anxiogenic stimuli: Possible involvement of the endocannabinoid and endovanilloid systems, Neurobiology of Disease 36 (2009), pp. 70-80.

M. Fu et al., TRPV1: A potential target for antiepileptogenesis, Medical Hypotheses 73 (2009), pp. 100-102.

F. Leung, Capsaicin-sensitive intestinal mucosal afferent mechanism and body fat distribution, Life Sciences 83 (2008), pp. 1-5.

A. Suri et al., The emerging role of TRPV1 in diabetes and obesity, Trends in Pharmacological Sciences, vol. 29, No. 1, pp. 29-36 (2007).

J. Li et al., Increased GFR and renal excretory function by activation of TRPV in the isolated prefused kidney, Pharmacological Research vol. 57, Issue 3 (2008), pp. 239-246.

M. Ghasemi et al., Effect of anandamide on nonadrenergic noncholinergic-mediated relaxation of rat corpus cavernosum, European Journal of Pharmacology vol. 544, Issues 1-3 (2006), pp. 138-145.

S. Mandadi et al., Locomotor Networks Are Targets of Modulation by Sensory Transient Receptor Potential Vanilloid 1 and Transient Receptor Potential Melastatin 8 Channels, Neuroscience 162 (2009) pp. 1377-1397.

R. Marsch et al., Reduced Anxiety, Conditioned Fear, and Hippocampal Long-Term Potentiation in Transient Receptor Potential Vanilloid Type 1 Receptor-Deficient Mice, The Journal of Neuroscience, Jan. 24, 2007, vol. 27, No. 4, pp. 832-839.

H. Eilers, Anesthetic Activation of Nociceptors: Adding Insult to Injury?, Molecular Interventions, Oct. 2008, vol. 8, Issue 5, pp. 226-229.

Won-Sik Shim et al., TRPV1 Mediates Histamine-Induced Itching via the Activation of Phospolipase $A_2$ and 12-Lipoxygenase, The Journal of Neuroscience, Feb. 28, 2007, vol. 27, No. 9, pp. 2331-2337.

W. Huang, Enhanced postmycocardial infarction fibrosis via stimulation of the transforming growth factor-B-Smad2 signaling pathway: role of transient receptor potential vanilloid type 1 channels, Journal of Hypertension vol. 27 (2009).

I. J. You et al., Society for Neuroscience, Abstract, Vo. 912.22 (2007).

J. Donnerer et al., Pharmacology, Feb. 2005; vol. 73, Issue 2, pp. 97-101 (2005) E. pub Oct. 18, 2004.

John J. Adcock, TRPV1 receptors in sensitization of cough and pain reflexes, Pulmonary Pharmacology & Therapeutics 22 (2009) 65-70.

Teshamae S. Monteith et al., Acute Migraine Therapy: New Drugs and New Approaches, Current Treatment in Neurology (2011) 13: 1-14.

Magdalene M. Moran et al., Transient receptor potential channels as therapeutic targets, Nature Review, Drug Discovery, vol. 10, Aug. 2011, pp. 601-620.

Celia D. Cruz et al., Intrathecal delivery of resiniferatoxin (RTX) reduces detrusor overactivity and spinal expression of TRPV1 in spinal cord injured animals, Experimental Neurology 214 (2008) 301-308.

Naoki Yoshimura et al., Therapeutic receptor targets for lower urinary tract dysfunction, Nauyn-Schmiedeberg's Arch Pharmacol (2008) 377:437-448.

Carols Silva et al., Bladder sensory densitization decreases urinary urgency, BMC Urology 2007, 7-9.

Klaus Urbahns et al., Naphthol derivatives as TRPV1 inhibitors for the treatment of urinary incontinence, Bioorganic & Medicinal Chemistry Letters 21 (2011) 3354-3357.

Smith et al., "March's Advanced Organic Chemistry: Reactions, Mechanisms, and Structure," $6^{th}$ Edition—Table of Content, 2007 (four (4) pages) Date Added.

Carey et al., "Advanced Organic Chemistry—Part A: Structure and Mechanisms," $5^{th}$ Edition, 2007 (twenty-two (22) pages) Date Added.

Carey et al., "Advanced Organic Chemistry—Part B: Reactions and Synthesis," $5^{th}$ Edition, 2007 (twenty-two (22) pages) Date Added.

Remington's Pharmaceutical Sciences, A.R. Gennaro (Editor), $17^{th}$ edition, 1985, Chapters 77-86 (one hundred twenty-nine (129) pages) Title Corrected and Editor, Edition, and Date Added.

Remington's Pharmaceutical Sciences, A.R. Gennaro (Editor), $17^{th}$ edition, 1985, Chapter 76 (fifteen (15) pages).

Remington's Pharmaceutical Sciences, A.R. Gennaro (Editor), $17^{th}$ edition, 1985, Chapters 87-93 (one hundred twenty-five (125) pages).

* cited by examiner

AMINE SUBSTITUTED METHANESULFONAMIDE DERIVATIVES AS VANILLOID RECEPTOR LIGANDS

This application claims priority from U.S. provisional patent application No. 61/539,170, filed Sep. 26, 2011, the entire disclosure of which is incorporated herein by reference. Priority is also claimed based on European patent application no. EP 11 007 805.2, filed Sep. 26, 2011, the entire disclosure of which is likewise incorporated herein by reference.

The invention relates to amine substituted methanesulfonamide derivatives as vanilloid receptor ligands, to pharmaceutical compositions containing these compounds and also to these compounds for use in the treatment and/or prophylaxis of pain and further diseases and/or disorders.

The treatment of pain, in particular of neuropathic pain, is very important in medicine. There is a worldwide demand for effective pain therapies. The urgent need for action for a patient-focused and target-oriented treatment of chronic and non-chronic states of pain, this being understood to mean the successful and satisfactory treatment of pain for the patient, is also documented in the large number of scientific studies which have recently appeared in the field of applied analgesics or basic research on nociception.

The subtype 1 vanilloid receptor (VR1/TRPV1), which is often also referred to as the capsaicin receptor, is a suitable starting point for the treatment of pain, in particular of pain selected from the group consisting of acute pain, chronic pain, neuropathic pain and visceral pain. This receptor is stimulated inter alia by vanilloids such as capsaicin, heat and protons and plays a central role in the formation of pain. In addition, it is important for a large number of further physiological and pathophysiological processes and is a suitable target for the therapy of a large number of further disorders such as, for example, migraine, depression, neurodegenerative diseases, cognitive disorders, states of anxiety, epilepsy, coughs, diarrhoea, pruritus, inflammations, disorders of the cardiovascular system, eating disorders, medication dependency, misuse of medication and urinary incontinence.

There is a demand for further compounds having comparable or better properties, not only with regard to affinity to vanilloid receptors 1 (VR1/TRPV1 receptors) per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by vanilloid receptors 1 (VR1/TRPV1 receptors).

This object is achieved by the subject matter described herein.

It has surprisingly been found that the substituted compounds of general formula (I), as given below, display outstanding affinity to the subtype 1 vanilloid receptor (VR1/TRPV1 receptor) and are therefore particularly suitable for the prophylaxis and/or treatment of disorders or diseases which are at least partially mediated by vanilloid receptors 1 (VR1/TRPV1).

The present invention therefore relates to a substituted compound of general formula (I)

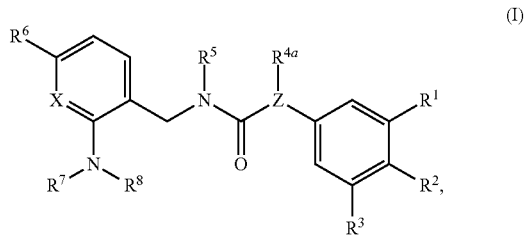

wherein one of residues $R^1$ and $R^2$ denotes $CH_2$—$N(R^9)$—$S(=O)_2$—$R^{10}$, wherein $R^9$ represents H, $CH_3$ or $C_2H_5$, and wherein $R^{10}$ represents $NH_2$, $CH_3$ or $C_2H_5$, and the respective remaining residue of $R^1$ and $R^2$ is selected from the group consisting of H, F, Cl, Br, I, $CH_3$, $CH_2$—OH, $CH_2$—$CH_2$—OH, $CH_2$—O—$CH_3$, $CH_2$—$CH_2$—O—$CH_3$, $CF_3$, OH, O—$CH_3$, O—$CH_2$—OH, O—$CH_2$—O—$CH_3$, O—$C_2H_5$, O—$CH_2$—$CH_2$—OH, O—$CH_2$—$CH_2$—O—$CH_3$ and $NH_2$, $R^3$ is selected from the group consisting of H, F, Cl, Br, I, $CH_3$, $CF_3$, OH, O—$CH_3$, O—$CF_3$, and $NH_2$, Z represents N or C—$R^{4b}$, wherein $R^{4b}$ represents H or $CH_3$, $R^{4a}$ represents H or $CH_3$, $R^5$ represents H or $CH_3$, X represents N or CH;

$R^6$ represents $CF_3$, an unsubstituted, saturated $C_{1-4}$ aliphatic residue or an unsubstituted, saturated $C_{3-6}$ cycloaliphatic residue, $R^7$ represents H, or an unsubstituted $C_{1-4}$ aliphatic residue, $R^8$ represents a $C_{1-4}$ aliphatic residue, unsubstituted or mono-, di- or trisubstituted with 1, 2 or 3 substituents selected independently of one another from the group consisting of F, Cl, Br, I, OH, O—$CH_3$, O—$CH_2$—OH, O—$CH_2$—O—$CH_3$, O—$C_2H_5$, O—$CH_2$—$CH_2$—OH, O—$CH_2$—$CH_2$—O—$CH_3$, $NH_2$, $NH(CH_3)$, and $N(CH_3)_2$, preferably an unsubstituted $C_{1-4}$ aliphatic residue;

a $C_{3-6}$ cycloaliphatic residue, optionally bridged via an unsubstituted, saturated $C_{1-4}$ aliphatic group, unsubstituted or mono-, or di-, or trisubstituted with 1, 2 or 3 substituents selected independently of one another from the group consisting of F, Cl, Br, I, $CH_3$, $C_2H_5$, $CH_2$—OH, $CH_2$—$CH_2$—OH, $CH_2$—O—$CH_3$, $CH_2$—$CH_2$—O—$CH_3$, $CH_2$—$NH(CH_3)$, $CH_2$—$N(CH_3)_2$, $CF_3$, OH, O—$CH_3$, O—$CH_2$—OH, O—$CH_2$—O—$CH_3$, O—$C_2H_5$, O—$CH_2$—$CH_2$—OH, O—$CH_2$—$CH_2$—O—$CH_3$, $NH_2$, $NH(CH_3)$, and $N(CH_3)_2$;

aryl or heteroaryl, preferably phenyl, in each case optionally bridged via an unsubstituted, saturated $C_{1-4}$ aliphatic group, and in each case unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—$CH_2$—OH, $CH_2$—O—$CH_3$, $CH_2$—$CH_2$—O—$CH_3$, $CF_3$, OH, O—$CH_3$, O—$CH_2$—OH, O—$CH_2$—O—$CH_3$, O—$C_2H_5$, O—$CH_2$—$CH_2$—OH, O—$CH_2$—$CH_2$—O—$CH_3$, O—$CF_3$, S—$CF_3$, $NH_2$, $NH(CH_3)$, and $N(CH_3)_2$;

or $R^7$ and $R^8$ together with the nitrogen atom connecting them form a 3 to 6 membered heterocycloaliphatic residue, unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—$CH_2$—OH, $CH_2$—O—$CH_3$, $CH_2$—$CH_2$—O—$CH_3$, $CH_2$—$NH(CH_3)$, $CH_2$—$N(CH_3)_2$, $CF_3$, OH, O—$CH_3$, O—$CH_2$—OH, O—$CH_2$—O—$CH_3$, O—$C_2H_5$, O—$CH_2$—$CH_2$—OH, O—$CH_2$—$CH_2$—O—$CH_3$, O—$CF_3$, SH, S—$CH_3$, S—$CF_3$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$, wherein said 3 to 6 membered heterocycloaliphatic residue can optionally be condensed with a further ring selected from the group consisting of phenyl, pyridyl, a $C_{3-6}$ cycloaliphatic residue and a 3 to 6 membered heterocycloaliphatic residue, wherein said furthr ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl, in which an "aliphatic group" and an "aliphatic residue" can in each case, independently of one another, be branched or unbranched, saturated or unsaturated, if not indicated otherwise;

in which a "cycloaliphatic residue" and a "heterocycloaliphatic residue" can in each case, independently of one another, be saturated or unsaturated, if not indicated otherwise;

optionally in the form of a single stereoisomer or a mixture of stereoisomers, in the form of the free compound and/or a physiologically acceptable salt thereof or in the form of a solvate, in particular a hydrate.

The term "single stereoisomer" comprises in the sense of this invention an individual enantiomer or diastereomer. The term "mixture of stereoisomers" comprises in the sense of this invention the racemate and mixtures of enantiomers and/or diastereomers in any mixing ratio.

The term "physiologically acceptable salt" comprises in the sense of this invention a salt of at least one compound according to the present invention and at least one physiologically acceptable acid or base.

The term "$C_{1-4}$ aliphatic residue" comprises in the sense of this invention acyclic saturated or unsaturated aliphatic hydrocarbon residues, which can be branched or unbranched and also unsubstituted or mono- or polysubstituted if not indicated otherwise, which contain 1 to 4 carbon atoms (i.e. 1, 2, 3 or 4 carbon atoms) respectively, i.e. $C_{1-4}$ alkanyls ($C_{1-4}$ alkyls), $C_{2-4}$ alkenyls and $C_{2-4}$ alkynyls, respectively. Alkenyls comprise at least one C—C double bond (a C=C-bond) and alkynyls comprise at least one C—C triple bond (a C≡C-bond). Preferably, aliphatic residues are selected from the group consisting of alkanyl (alkyl) and alkenyl residues, more preferably are alkanyl (alkyl) residues. Preferred $C_{1-4}$ alkanyl residues are selected from the group consisting of methyl, ethyl, n-propyl, 2-propyl, n-butyl, isobutyl, sec.-butyl, and tert.-butyl. Preferred $C_{2-4}$ alkenyl residues are selected from the group consisting of ethenyl (vinyl), propenyl (—$CH_2CH$=$CH_2$, —CH=CH—$CH_3$, —C(=$CH_2$)—$CH_3$) and butenyl. Preferred $C_{2-4}$ alkynyl residues are selected from the group consisting of ethynyl, propynyl (—$CH_2$—C≡CH, —C≡C—$CH_3$) and butynyl.

The term "$C_{3-6}$ cycloaliphatic residue" means for the purposes of this invention cyclic aliphatic hydrocarbons containing 3, 4, 5 or 6 carbon atoms, wherein the hydrocarbons in each case can be saturated or unsaturated (but not aromatic), unsubstituted or mono- or polysubstituted, if not indicated otherwise. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. Examples for cycloaliphatic residues which are condensed with a further ring system are e.g. tetrahydronaphthyl and dihydroindenyl. Preferred $C_{3-6}$ cycloaliphatic residues are selected from the group consisting of cyclopropyl, cyclobutyl, cyclopentyl, cyclohexyl, cyclopentenyl, and cyclohexenyl. Particularly preferred $C_{3-6}$ cycloaliphatic residues are $C_{5-6}$ cycloaliphatic residues such as cyclopentyl, cyclohexyl, cyclopentenyl and cyclohexenyl.

The term "3-6-membered heterocycloaliphatic residue" means for the purposes of this invention heterocycloaliphatic saturated or unsaturated (but not aromatic) residues having 3-6, i.e. 3, 4, 5 or 6 ring members, in which in each case at least one, if appropriate also two or three carbon atoms are replaced by a heteroatom or a heteroatom group each selected independently of one another from the group consisting of O, S, S(=O)$_2$, N, NH and N($C_{1-8}$ alkyl) such as N($CH_3$), preferably are replaced by a heteroatom or a heteroatom group each selected independently of one another from the group consisting of O, S, N, NH and N($C_{1-8}$ alkyl) such as N($CH_3$), wherein the ring members can be unsubstituted or mono- or polysubstituted, if not indicated otherwise. The heterocycloaliphatic residue can be bound to the superordinate general structure via any desired and possible ring member of the heterocycloaliphatic residue if not indicated otherwise. The heterocycloaliphatic residues can also be condensed with further saturated, (partially) unsaturated (hetero)cycloaliphatic or aromatic or heteroaromatic ring systems, i.e. with cycloaliphatic, heterocycloaliphatic, aryl or heteroaryl residues, which can in turn be unsubstituted or mono- or polysubstituted, if not indicated otherwise. Examples for heterocycloaliphatic residues which are condensed with a further ring system are e.g. indolinyl and isoindolinyl. The term "condensed" also refers to and includes spirocycles, i.e. an at least bicyclic ring system, wherein the 3-6-membered heterocycloaliphatic residue is connected through just one (spiro) atom with a further saturated, (partially) unsaturated (hetero) cycloaliphatic or aromatic or heteroaromatic ring system. An example of such a spirocycle is 1-oxa-2,8-diazaspiro[4.5]dec-2-en-8-yl. Preferred heterocycloaliphatic residues are selected from the group consisting of azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, morpholinyl, oxiranyl, oxetanyl, pyrrolidinyl, piperazinyl, 4-methylpiperazinyl, piperidinyl, pyrazolidinyl, pyranyl, tetrahydropyrrolyl, tetrahydropyranyl, in particular tetrahydro-2H-pyran-4-yl, tetrahydrofuranyl, tetrahydropyridinyl, tetrahydrothiophenyl, tetrahydroisoxazolyl, thiazolidinyl and thiomorpholinyl. Preferred condensed heterocycloaliphatic residues are e.g. 1-oxa-2,8-diazaspiro[4.5]dec-2-en-8-yl, dihydroquinolinyl, dihydroindenyl, dihydroisoquinolinyl, dihydroindolinyl, dihydroisoindolyl, tetrahydroquinolinyl, tetrahydroisoquinolinyl, tetrahydroindolinyl, tetrahydropyridoindolyl, tetrahydronaphthyl, and tetrahydrocarbolinyl.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted if not indicated otherwise, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted, if not indicated otherwise. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted, if not indicated otherwise. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl(furanyl), imidazolyl, imidazothiazolyl, indazolyl, indolizinyl, indolyl, isoquinolinyl, isoxazolyl, isothiazolyl, naphthyridinyl, oxazolyl, oxadiazolyl, phenazinyl, phenothiazinyl, phthalazinyl, pyrazolyl, pyridyl(2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

The term "bridged via a $C_{1-4}$ aliphatic group" with respect to residues as aryl, heteroaryl, a heterocycloaliphatic residue and a cycloaliphatic residue mean for the purpose of the invention that these residues have the above-defined meanings and that each of these residues is bound to the respective superordinate general structure via a $C_{1-4}$ aliphatic group. The $C_{1-4}$ aliphatic group can in all cases be branched or unbranched, unsubstituted or mono- or polysubstituted, if not indicated otherwise. The $C_{1-4}$ aliphatic group can in all cases be furthermore saturated or unsaturated, i.e. can be a $C_{1-4}$ alkylene group, a $C_{2-4}$ alkenylene group or a $C_{2-4}$ alkynylene group. Preferably, the $C_{1-4}$-aliphatic group is a $C_{1-4}$ alkylene group or a $C_{2-4}$ alkenylene group, more preferably a $C_{1-4}$ alkylene group. Preferred $C_{1-4}$ alkylene groups are selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)— and —C(CH$_3$)(CH$_2$CH$_3$)—. Preferred $C_{2-4}$ alkenylene groups are selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)— and —C(CH$_2$CH$_3$)=CH—. Preferred $C_{2-4}$ alkynylene groups are selected from the group consisting of —C≡C—, —C≡C—CH$_2$—, —C≡C—CH$_2$—CH$_2$—, —C≡C—CH(CH$_3$)—, —CH$_2$—C≡C—CH$_2$— and —C≡C—C≡C—.

In relation to the terms "aliphatic residue", "aliphatic group", "cycloaliphatic residue" and "heterocycloaliphatic residue", the term "substituted" refers in the sense of this invention, with respect to the corresponding residues or groups, to the single substitution or multiple substitution (polysubstitution), e.g. disubstitution or trisubstitution, of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of CF$_3$, CH$_2$CF$_3$ or disubstituted as in the case of 1,1-difluorocyclohexyl, or at various points, as in the case of CH(OH)—CH=CH—CHCl$_2$ or 1-chloro-3-fluorocyclohexyl. The multiple substitution can be carried out using the same or using different substituents.

In relation to the terms "aryl" and "heteroaryl", the term "substituted" refers in the sense of this invention, with respect to the corresponding residues or groups, to the single substitution or multiple substitution (polysubstitution), e.g. disubstitution or trisubstitution, of one or more hydrogen atoms each independently of one another by at least one substituent. The multiple substitution can be carried out using the same or using different substituents.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^7$ and $R^8$ denote a $C_{1-4}$ aliphatic residue, then the $C_{1-4}$ aliphatic residue can e.g. represent methyl for $R^7$ and can represent ethyl for $R^8$.

The terms "salt formed with a physiologically compatible acid" or "salt of physiologically acceptable acids" refers in the sense of this invention to salts of the respective active ingredient with inorganic or organic acids which are physiologically compatible—in particular when used in human beings and/or other mammals. Examples of physiologically acceptable acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

The terms "salt formed with a physiologically compatible base" or "salt of physiologically acceptable bases" refers in the sense of this invention to salts of the respective compound according to the invention—as an anion, e.g. upon deprotonation of a suitable functional group—with at least one cation or base—preferably with at least one inorganic cation—which are physiologically acceptable—in particular when used in human beings and/or other mammals. Particularly preferred are the salts of the alkali and alkaline earth metals, in particular (mono-) or (di)sodium, (mono-) or (di)potassium, magnesium or calcium salts, but also ammonium salts $[NH_xR_{4-x}]^+$, in which x=0, 1, 2, 3 or 4 and R represents a branched or unbranched $C_{1-4}$ aliphatic residue.

Further preferred embodiments of the compound according to the invention of general formula (I) have general formulae (I-a) and/or (I-b)

(I-a)

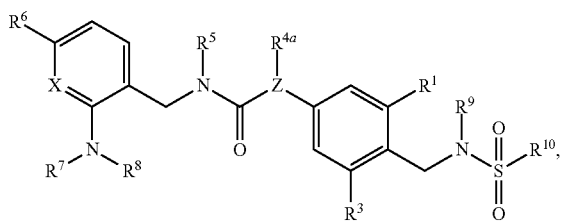

(I-b)

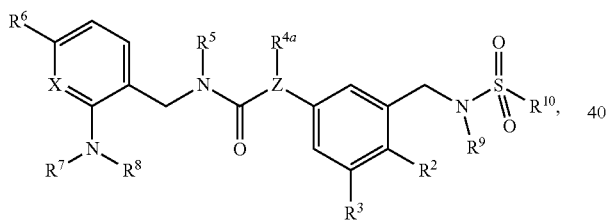

wherein the particular radicals and variables have the meanings described herein in connection with the compounds according to the invention and preferred embodiments thereof. More preferred is an inventive compound according to formula (I-a).

Particularly preferred embodiments of the compound of general formulae (I-a) and (I-b), respectively, have general formulae (I-a-1) and/or (I-b-1), respectively (I-a-1)

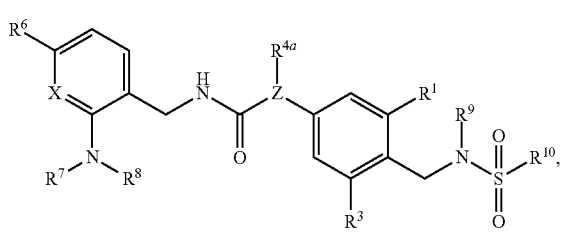

(I-b-1)

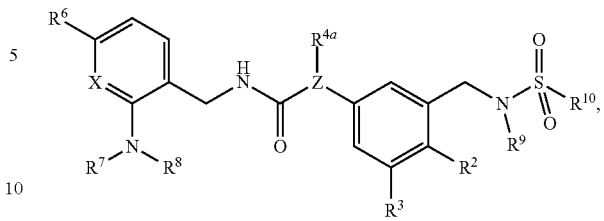

wherein the particular radicals and variables have the meanings described herein in connection with the compounds according to the invention and preferred embodiments thereof. Even more preferred is an inventive compound according to formula (I-a-1).

Most preferred embodiments of the compound of general formulae (I-a-1) and (I-b-1), respectively, have general formulae (I-a-1-a), (I-a-1-b), (I-b-1-a) and/or (I-b-1-b), respectively (I-a-1-a)

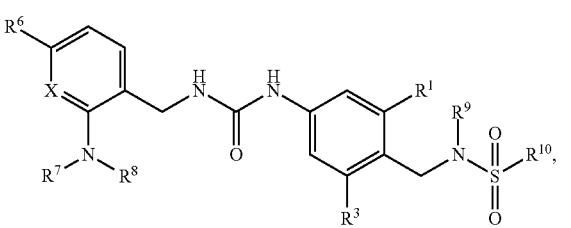

(I-b-1-a)

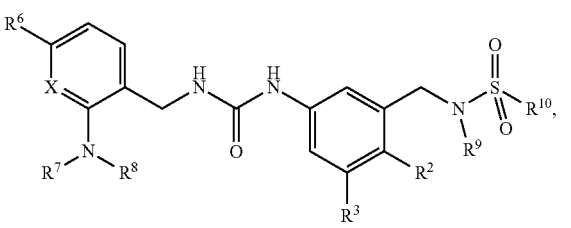

(I-a-1-b)

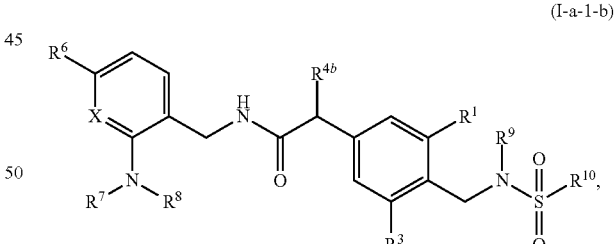

(I-b-1-b)

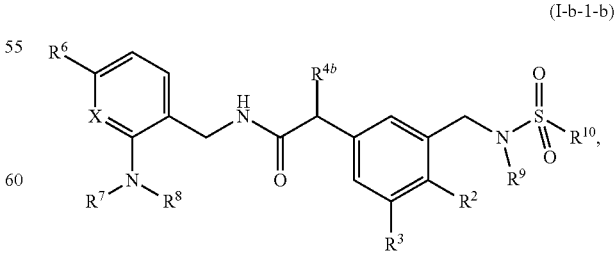

wherein the particular radicals and variables have the meanings described herein in connection with the compounds according to the invention and preferred embodiments thereof. Particularly preferred is an inventive compound according to formula (I-a-1-a) and/or (I-a-1-b).

Further preferred embodiments of the compound of general formula (I) have the following general formulae:

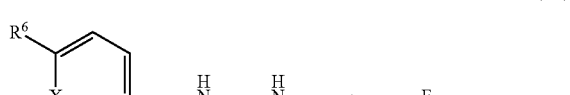
(I-c)

(I-d)

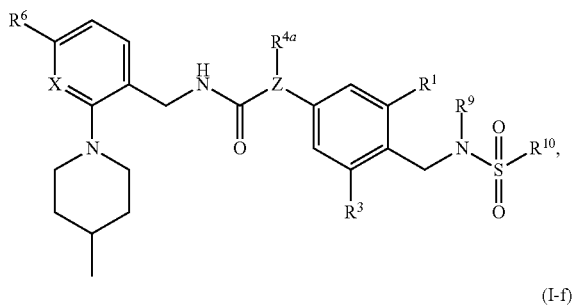
(I-e)

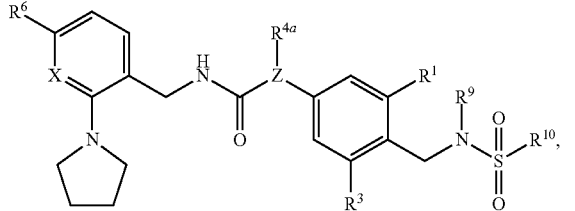
(I-f)

wherein the particular radicals and variables have the meanings described herein in connection with the compounds according to the invention and preferred embodiments thereof.

In a further preferred embodiment of the compound of general formula (I) according to the present invention
one of residues $R^1$ and $R^2$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$.
  Preferably,
one of residues $R^1$ and $R^2$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and the respective remaining residue of $R^1$ and $R^2$ is selected from the group consisting of H, F, Cl, Br, I, $CH_3$, $CF_3$, OH, and O—$CH_3$.
  More preferably,
one of residues $R^1$ and $R^2$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and the respective remaining residue of $R^1$ and $R^2$ is selected from the group consisting of H, F, Cl, $CH_3$, OH, and O—$CH_3$.

In another preferred embodiment of the compound of general formula (I) according to the present invention
$R^2$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and $R^1$ is selected from the group consisting of H, F, Cl, Br, I, $CH_3$, $CH_2$—OH, $CH_2$—O—$CH_3$, $CF_3$, OH, and O—$CH_3$.
  Preferably,
$R^2$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and $R^1$ is selected from the group consisting of H, F, Cl, Br, I, $CH_3$, $CF_3$, OH, and O—$CH_3$.
  More preferably,
$R^2$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
  and $R^1$ is selected from the group consisting of H, F, Cl, $CH_3$, OH, and O—$CH_3$.

In yet another preferred embodiment of the compound of general formula (I) according to the present invention
$R^1$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and $R^2$ is selected from the group consisting of H, F, Cl, Br, I, $CH_3$, $CH_2$—OH, $CH_2$—O—$CH_3$, $CF_3$, OH, and O—$CH_3$.
  Preferably,
$R^1$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and $R^2$ is selected from the group consisting of H, F, Cl, Br, I, $CH_3$, $CF_3$, OH, and O—$CH_3$.
  More preferably,
$R^1$ denotes $CH_2$—$N(R^9)$—$S(=O)_2$—$R^{10}$,
  wherein $R^9$ represents H, $CH_3$, or $C_2H_5$, and
  wherein $R^{10}$ represents $NH_2$, $CH_3$, or $C_2H_5$,
and $R^2$ is selected from the group consisting of H, F, Cl, $CH_3$, OH, and O—$CH_3$.

In a further preferred embodiment of the compound of general formula (I) according to the present invention
$R^3$ is selected from the group consisting of H, F, Cl, $CH_3$, $CF_3$, OH and O—$CH_3$.
  Preferably,
$R^3$ is selected from the group consisting of H, F, Cl, $CH_3$, and O—$CH_3$.
  More preferably,
$R^3$ is selected from the group consisting of H, F, and Cl, even more preferably denotes H or F, in particular H.

In another preferred embodiment of the compound of general formula (I) according to the present invention
Z represents N and
$R^{4a}$ represents H,
or
Z represents C—$R^{4b}$,
  wherein $R^{4b}$ represents H or $CH_3$, and
$R^{4a}$ represents H.

In yet another preferred embodiment of the compound of general formula (I) according to the present invention
Z represents N and
$R^{4a}$ represents H,
or
Z represents C—$R^{4b}$,
wherein $R^{4b}$ represents H, and
$R^{4a}$ represents H or $CH_3$.

In a further preferred embodiment of the compound of general formula (I) according to the present invention,
Z represents N and $R^{4a}$ represents H; or
Z represents $CR^{4b}$ and $R^{4a}$ and $R^{4b}$ each represent H; or
Z represents $CR^{4b}$ and $R^{4a}$ represents methyl and $R^{4b}$ represents H; or
Z represents $CR^{4b}$ and $R^{4a}$ represents H and $R^{4b}$ represents methyl.

In another preferred embodiment of the compound of general formula (I) according to the present invention
$R^5$ represents H.

In a further preferred embodiment of the compound of general formula (I) according to the present invention
X represents N.

In another preferred embodiment of the compound of general formula (I) according to the present invention
X represents CH.

In a further preferred embodiment of the compound of general formula (I) according to the present invention
$R^6$ represents $CF_3$, methyl, ethyl, 2-propyl, isobutyl, sec.-butyl, tert.-butyl, cyclopropyl, cyclobutyl or cyclopentyl.

Preferably,
$R^6$ represents $CF_3$, methyl, ethyl, 2-propyl, tert.-butyl, cyclopropyl, or cyclobutyl.

More preferably,
$R^6$ represents $CF_3$, tert.-Butyl or cyclopropyl.

In another preferred embodiment of the compound of general formula (I) according to the present invention
$R^7$ represents H or an unsubstituted, saturated, $C_{1-4}$ aliphatic residue,
$R^8$ represents a $C_{1-4}$ aliphatic residue, unsubstituted or mono- or disubstituted with 1, 2 or 3 substituents selected independently of one another from the group consisting of F, Cl, OH, and O—$CH_3$;
  a $C_{3-6}$ cycloaliphatic residue, unsubstituted or mono-, or di-, or trisubstituted with 1, 2 or 3 substituents selected independently of one another from the group consisting of F, Cl, Br, I, $CH_3$, $C_2H_5$, $CF_3$, OH, O—$CH_3$, $NH_2$, $NH(CH_3)$, and $N(CH_3)_2$;
  phenyl or pyridyl, in each case unsubstituted or mono-, or di- or trisubstituted with 1, 2 or 3 substituents selected independently of one another from the group consisting of F, Cl, Br, I, $CH_3$, $C_2H_5$, $CF_3$, OH, O—$CH_3$, O—$CF_3$, S—$CF_3$, $NH_2$, $NH(CH_3)$, and $N(CH_3)_2$;
or
$R^7$ and $R^8$ together with the nitrogen atom connecting them form a 3 to 6 membered heterocycloaliphatic residue, unsubstituted or mono-, or di- or trisubstituted with 1, 2 or 3 substituents selected independently of one another from the group consisting of F, Cl, Br, I, $CH_3$, $C_2H_5$, $CH_2$—OH, $C_2H_4$—OH, $CH_2$—O—$CH_3$, $CH_2$—$CH_2$—O—$CH_3$, $CH_2$—$NH(CH_3)$, $CH_2$—$N(CH_3)_2$, $CF_3$, OH, O—$CH_3$, O—$CH_2$—OH, O—$CH_2$—O—$CH_3$, O—$C_2H_5$, O—$CH_2$—$CH_2$—OH, O—$CH_2$—$CH_2$—O—$CH_3$, O—$CF_3$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$,
wherein said 3 to 6 membered heterocycloaliphatic residue can optionally be condensed with a further ring selected from the group consisting of phenyl, heteroaryl, a $C_{3-6}$ cycloaliphatic residue and a 3 to 6 membered heterocycloaliphatic residue, wherein said ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl.

Preferably,
$R^7$ represents H, $CH_3$, $C_2H_5$, n-propyl, iso-propyl, n-butyl or tert.-butyl,
$R^8$ represents $CH_3$, $C_2H_5$, n-propyl, iso-propyl, n-butyl, tert.-butyl, cyclopropyl, cyclobutyl, cyclopentyl, cyclohexyl, or phenyl, wherein phenyl can be unsubstituted or mono-, or di- or trisubstituted with 1, 2 or 3 substituents selected independently of one another from the group consisting of F, Cl, Br, I, $CH_3$, $CF_3$, OH, O—$CH_3$, and O—$CF_3$;
or
$R^7$ and $R^8$ together with the nitrogen atom connecting them form a 3 to 6 membered heterocycloaliphatic residue selected from the group consisting of azetidinyl, pyrrolidinyl, piperidinyl, piperazinyl and morpholinyl, in each case independently of one another unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—O—$CH_3$, $CH_2$—$NH(CH_3)$, $CH_2$—$N(CH_3)_2$, $CF_3$, OH, O—$CH_3$, O—$CH_2$—O—$CH_3$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$,
wherein said 3 to 6 membered heterocycloaliphatic residue can optionally be condensed with a further ring selected from the group consisting of a $C_{3-6}$ cycloaliphatic residue and a 3 to 6 membered heterocycloaliphatic residue, wherein said ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl.

More preferably,
$R^7$ represents H, $CH_3$, $C_2H_5$, n-propyl, iso-propyl, n-butyl or tert.-butyl,
$R^8$ represents $CH_3$, $C_2H_5$, n-propyl, iso-propyl, n-butyl, tert.-butyl, cyclopentyl, cyclohexyl, or phenyl, wherein phenyl can be unsubstituted or mono-, or di- or trisubstituted with 1, 2 or 3 substituents selected independently of one another from the group consisting of F, Cl, Br, I, $CH_3$, $CF_3$, OH, O—$CH_3$, and O—$CF_3$;
or
$R^7$ and $R^8$ together with the nitrogen atom connecting them form a 3 to 6 membered heterocycloaliphatic residue selected from the group consisting of azetidinyl, pyrrolidinyl, piperidinyl, piperazinyl and morpholinyl, in each case independently of one another unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—O—$CH_3$, $CH_2$—NH($CH_3$), $CH_2$—N($CH_3$)$_2$, $CF_3$, OH, O—$CH_3$, $NH_2$, NH($CH_3$), N($CH_3$)$_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, $CH_3$, $CF_3$ and $OCH_3$, wherein said 3 to 6 membered heterocycloaliphatic residue can optionally be condensed with a further 3 to 6 membered heterocycloaliphatic residue, wherein said further 3 to 6 membered heterocycloaliphatic residue can be unsubstituted or mono-, or di- or trisubstituted with 1, 2 or 3 substituents selected independently of one another from the group consisting of F, Cl, $CH_3$, tert.-butyl, $CF_3$, $OCH_3$ and an unsubstituted phenyl.

Even more preferably, $R^7$ represents H, $CH_3$, $C_2H_5$, n-propyl, or n-butyl, $R^8$ represents $CH_3$, $C_2H_5$, n-propyl, iso-propyl, n-butyl, tert.-butyl, cyclohexyl, or phenyl, wherein phenyl can be unsubstituted or mono-, or di- or trisubstituted, preferably monoubstituted, with 1, 2 or 3 substituents selected independently of one another from the group consisting of F, Cl, $CH_3$, $CF_3$, OH, and O—$CH_3$;

or $R^7$ and $R^8$ together with the nitrogen atom connecting them form a 3 to 6 membered heterocycloaliphatic residue selected from the group consisting of azetidinyl, pyrrolidinyl, piperidinyl, piperazinyl and morpholinyl, in each case independently of one another unsubstituted or mono-, or di- or trisubstituted with 1, 2 or 3 substituents selected independently of one another from the group consisting of F, Cl, $CH_3$, $CH_2$—O—$CH_3$, $CH_2$—N($CH_3$)$_2$, O—$CH_3$, N($CH_3$)$_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, $CH_3$, $CF_3$ and $OCH_3$, wherein said 3 to 6 membered heterocycloaliphatic residue can optionally be condensed with a further preferably unsaturated 3 to 6 membered heterocycloaliphatic residue, wherein said further 3 to 6 membered heterocycloaliphatic residue can be unsubstituted or mono-, or di- or trisubstituted with 1, 2 or 3 substituents selected independently of one another from the group consisting of F, Cl, $CH_3$, tert.-butyl, $CF_3$, $OCH_3$ and an unsubstituted phenyl.

In another preferred embodiment of the compound of general formula (I) according to the present invention $R^7$ represents H, $CH_3$, $C_2H_5$, n-propyl, iso-propyl, n-butyl or tert.-butyl, $R^8$ represents $CH_3$, $C_2H_5$, n-propyl, iso-propyl, n-butyl, tert.-butyl, cyclopentyl, cyclohexyl, or phenyl, wherein phenyl can be unsubstituted or mono-, or di- or trisubstituted, preferably monosubstituted, with 1, 2 or 3 substituents selected independently of one another from the group consisting of F, Cl, Br, I, $CH_3$, $CF_3$, OH, O—$CH_3$, and O—$CF_3$;

or $R^7$ and $R^8$ together with the nitrogen atom connecting them form the part structure (T1)

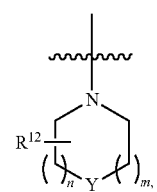

(T1)

wherein m denotes 0 or 1, n denotes 0 or 1,

Y represents O, $NR^{13}$ or $C(R^{14})(R^{15})$, $R^{12}$, $R^{14}$ and $R^{15}$ independently of one another are selected from the group consisting of H, F, Cl, Br, I, $CH_3$, $C_2H_5$, $CH_2$—OH, $C_2H_4$—OH, $CH_2$—O—$CH_3$, $C_2H_4$—O—$CH_3$, $CH_2$—NH($CH_3$), $CH_2$—N($CH_3$)$_2$, $CF_3$, OH, O—$CH_3$, O—$CH_2$—OH, O—$CH_2$—O—$CH_3$, O—$C_2H_5$, O—$C_2H_4$—OH, O—$C_2H_4$—O—$CH_3$, O—$CF_3$, $NH_2$, NH($CH_3$), N($CH_3$)$_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$, or $R^{14}$ and $R^{15}$ together with the carbon atom connecting them form a $C_{3-6}$ cycloaliphatic residue or a 3 to 6 membered heterocycloaliphatic residue, preferably a 3 to 6 membered heterocycloaliphatic residue, wherein said $C_{3-6}$ cycloaliphatic residue or 3 to 6 membered heterocycloaliphatic residue can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl, $R^{13}$ denotes H, $CH_3$, $C_2H_5$, $CH_2$—OH, $C_2H_4$—OH, $CH_2$—O—$CH_3$, $C_2H_4$—O—$CH_3$, $CH_2$—NH($CH_3$), $CH_2$—N($CH_3$)$_2$, $CF_3$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$.

Preferably, $R^7$ represents H, $CH_3$, $C_2H_5$, n-propyl, iso-propyl, n-butyl or tert.-butyl, $R^8$ represents $CH_3$, $C_2H_5$, n-propyl, iso-propyl, n-butyl, tert.-butyl, cyclopentyl, cyclohexyl, or phenyl, wherein phenyl can be unsubstituted or mono-, or di- or trisubstituted with 1, 2 or 3 substituents selected independently of one another from the group consisting of F, Cl, Br, I, $CH_3$, $CF_3$, OH, O—$CH_3$, and O—$CF_3$;

or $R^7$ and $R^8$ together with the nitrogen atom connecting them form the part structure (T1)

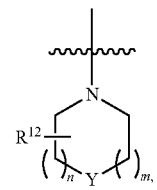

(T1)

wherein m denotes 0 or 1, n denotes 0 or 1,

Y represents O, $NR^{13}$ or $C(R^{14})(R^{15})$, $R^{12}$, $R^{14}$ and $R^{15}$ independently of one another are selected from the group consisting of H, F, Cl, Br, I, $CH_3$, $C_2H_5$, $CH_2$—OH, $C_2H_4$—OH, $CH_2$—O—$CH_3$, $C_2H_4$—O—$CH_3$, $CH_2$—$NH(CH_3)$, $CH_2$—$N(CH_3)_2$, $CF_3$, OH, O—$CH_3$, O—$CH_2$—O—$CH_3$, O—$C_2H_5$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$, or $R^{14}$ and $R^{15}$ together with the carbon atom connecting them form a 3 to 6 membered heterocycloaliphatic residue, wherein said 3 to 6 membered heterocycloaliphatic residue can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl, $R^{13}$ denotes H, $CH_3$, $C_2H_5$, $CH_2$—OH, $C_2H_4$—OH, $CH_2$—O—$CH_3$, $C_2H_4$—O—$CH_3$, $CH_2$—$NH(CH_3)$, $CH_2$—$N(CH_3)_2$, $CF_3$, phenyl, C(=O)-phenyl, benzyl or pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$.

More preferably, $R^7$ represents H, $CH_3$, $C_2H_5$, n-propyl, or n-butyl, $R^8$ represents $CH_3$, $C_2H_5$, n-propyl, iso-propyl, n-butyl, tert.-butyl, cyclohexyl, or phenyl, wherein phenyl can be unsubstituted or mono-, or di- or trisubstituted with 1, 2 or 3 substituents selected independently of one another from the group consisting of F, Cl, $CH_3$, $CF_3$, OH, O—$CH_3$, and O—$CF_3$;

or $R^7$ and $R^8$ together with the nitrogen atom connecting them form the part structure (T1)

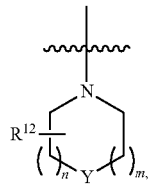

(T1)

wherein m denotes 0 or 1, n denotes 0 or 1,

Y represents O, $NR^{13}$ or $C(R^{14})(R^{15})$, $R^{12}$, $R^{14}$ and $R^{15}$ independently of one another are selected from the group consisting of H, F, Cl, $CH_3$, $CH_2$—O—$CH_3$, $C_2H_4$—O—$CH_3$, $CH_2$—$N(CH_3)_2$, $CF_3$, O—$CH_3$, O—$CH_2$—O—$CH_3$, O—$C_2H_5$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$, or $R^{14}$ and $R^{15}$ together with the carbon atom connecting them form a 3 to 6 membered heterocycloaliphatic residue, wherein said 3 to 6 membered heterocycloaliphatic residue can be unsubstituted or mono-, or di- or trisubstituted with 1, 2 or 3 substituents selected independently of one another from the group consisting of F, Cl, $CH_3$, tert.-butyl, $CF_3$, $OCH_3$ and an unsubstituted phenyl, $R^{13}$ denotes H, $CH_3$, $C_2H_5$, phenyl, C(=O)-phenyl, benzyl or pyridyl, wherein phenyl, benzyl and pyridyl can in each case independently of one another be unsubstituted or mono-, or di- or trisubstituted with 1, 2 or 3 substituents selected independently of one another from the group consisting of F, Cl, $CH_3$, $CF_3$ and $OCH_3$.

Even more preferably, $R^7$ represents H, $CH_3$, $C_2H_5$, or n-butyl, $R^8$ represents $CH_3$, $C_2H_5$, n-propyl, iso-propyl, n-butyl, tert.-butyl, cyclohexyl, or phenyl, wherein phenyl can be unsubstituted or monosubstituted with F or Cl, or $R^7$ and $R^8$ together with the nitrogen atom connecting them form the part structure (T1)

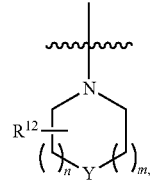

(T1)

wherein m denotes 0 or 1, and n denotes 0 or 1, and and

Y represents $C(R^{14})(R^{15})$, $R^{12}$, $R^{14}$ and $R^{15}$ independently of one another are selected from the group consisting of H, F, Cl, $CH_3$, $CH_2$—O—$CH_3$, $CH_2$—$N(CH_3)_2$, O—$CH_3$, $N(CH_3)_2$, phenyl, C(=O)-phenyl, benzyl and pyridyl, wherein phenyl, benzyl and pyridyl can in each case independently of one another be unsubstituted or monosubstituted with F, Cl, $CH_3$, $CF_3$ or $OCH_3$, or $R^{14}$ and $R^{15}$ together with the carbon atom connecting them form a 3 to 6 membered heterocycloaliphatic residue, preferably a dihydroisoxazolyl, wherein said 3 to 6 membered heterocycloaliphatic residue can be unsubstituted or monosubstituted with F, Cl, $CH_3$, tert.-butyl, $CF_3$, $OCH_3$ or an unsubstituted phenyl, or m denotes 1, and n denotes 1, and and Y represents O or $NR^{13}$, $R^{12}$ denotes H, or $CH_3$, and $R^{13}$ denotes H, $CH_3$, phenyl, or pyridyl, in each case unsubstituted.

A further particularly preferred embodiment of the compound of general formula (I) is an inventive compound corresponding to general formula (I-g),

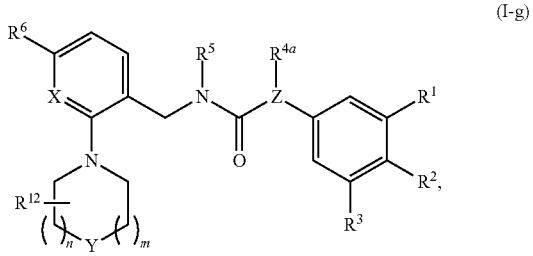

(I-g)

wherein $R^1$—$R^3$, $R^{4a}$, $R^5$, $R^6$, $R^{12}$, X, Y and Z as well as m and n have the meanings described herein in connection with the compounds according to the invention and preferred embodiments thereof.

Particularly preferred is a compound according to general formula (I), wherein
one of residues $R^1$ and $R^2$ denotes $CH_2$—$N(R^9)$—$S(=O)_2$—$R^{10}$,
  wherein $R^8$ represents H, $CH_3$, or $C_2H_5$,
  wherein $R^{10}$ represents $NH_2$, $CH_3$, or $C_2H_5$,
and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$,
$R^3$ is selected from the group consisting of H, F, Cl, $CH_3$, and O—$CH_3$,
Z represents N and
$R^{4a}$ represents H,
or
Z represents C—$R^{4b}$,
  wherein $R^{4b}$ represents H or $CH_3$, and
$R^{4a}$ represents H,
$R^5$ represents H,
X represents N or CH,
$R^6$ represents $CF_3$, tert.-Butyl or cyclopropyl,
$R^7$ represents H, $CH_3$, $C_2H_5$, n-propyl, iso-propyl, n-butyl or tert.-butyl,
$R^8$ represents $CH_3$, $C_2H_5$, n-propyl, iso-propyl, n-butyl, tert.-butyl, cyclopropyl, cyclobutyl, cyclopentyl, cyclohexyl, or phenyl, wherein phenyl can be unsubstituted or mono-, or di- or trisubstituted with 1, 2 or 3 substituents selected independently of one another from the group consisting of F, Cl, Br, I, $CH_3$, $CF_3$, OH, O—$CH_3$, and O—$CF_3$;
or
$R^7$ and $R^8$ together with the nitrogen atom connecting them form a 3 to 6 membered heterocycloaliphatic residue selected from the group consisting of azetidinyl, pyrrolidinyl, piperidinyl, piperazinyl and morpholinyl, in each case independently of one another unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—O—$CH_3$, $CH_2$—$NH(CH_3)$, $CH_2$—$N(CH_3)_2$, $CF_3$, OH, O—$CH_3$, O—$CH_2$—O—$CH_3$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$,
  wherein said 3 to 6 membered heterocycloaliphatic residue can optionally be condensed with a further ring selected from the group consisting of a $C_{3-6}$ cycloaliphatic residue and a 3 to 6 membered heterocycloaliphatic residue, wherein said ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl.

Even more particularly preferred is a compound according to general formula (I), wherein
one of residues $R^1$ and $R^2$ denotes $CH_2$—$N(R^9)$—$S(=O)_2$—$R^{10}$,
  wherein $R^8$ represents H, $CH_3$, or $C_2H_5$,
  wherein $R^{10}$ represents $NH_2$, $CH_3$, or $C_2H_5$,
and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$,
$R^3$ is selected from the group consisting of H, F, Cl, $CH_3$, and O—$CH_3$,
Z represents N and
$R^{4a}$ represents H,
or
Z represents C—$R^{4b}$,
  wherein $R^{4b}$ represents H or $CH_3$, and
$R^{4a}$ represents H,
$R^5$ represents H,
X represents N or CH,
$R^6$ represents $CF_3$, tert.-Butyl or cyclopropyl,
$R^7$ represents H, $CH_3$, $C_2H_5$, or n-butyl,
$R^8$ represents $CH_3$, $C_2H_5$, n-propyl, iso-propyl, n-butyl, tert.-butyl, cyclohexyl, or phenyl, wherein phenyl can be unsubstituted or monosubstituted with F or Cl,
or
$R^7$ and $R^8$ together with the nitrogen atom connecting them form the part structure (T1)

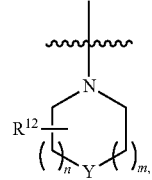

(T1)

wherein
m denotes 0 or 1, and
n denotes 0 or 1, and
and
Y represents $C(R^{14})(R^{15})$,
$R^{12}$, $R^{14}$ and $R^{15}$ independently of one another are selected from the group consisting of H, F, Cl, $CH_3$, $CH_2$—O—$CH_3$, $CH_2$—$N(CH_3)_2$, O—$CH_3$, $N(CH_3)_2$, phenyl, C(=O)-phenyl, benzyl and pyridyl, wherein phenyl, benzyl and pyridyl can in each case independently of one another be unsubstituted or monosubstituted with F, Cl, $CH_3$, $CF_3$ or $OCH_3$,
or $R^{14}$ and $R^{15}$ together with the carbon atom connecting them form a 3 to 6 membered heterocycloaliphatic residue, preferably a dihydroisoxazolyl, wherein said 3 to 6 membered heterocycloaliphatic residue can be unsubstituted or monosubstituted with F, Cl, $CH_3$, tert.-butyl, $CF_3$, $OCH_3$ or an unsubstituted phenyl,
or
m denotes 1, and
n denotes 1, and
and Y represents O or $NR^{13}$,
$R^{12}$ denotes H, or $CH_3$, and R$^{13}$ denotes H, CH$_3$, phenyl, or pyridyl, in each case unsubstituted.

Still more particularly preferred is a compound according to general formula (I), wherein
one of residues R$^1$ and R$^2$ denotes CH$_2$—N(R$^9$)—S(=O)$_2$—R$^{10}$,
wherein R$^8$ represents H, CH$_3$, or C$_2$H$_5$,
wherein R$^{10}$ represents NH$_2$, CH$_3$, or C$_2$H$_5$,
and the respective remaining residue of R$^1$ and R$^2$ is selected from the group consisting of H, F, Cl, Br, I, CH$_3$, CH$_2$—OH, CH$_2$—O—CH$_3$, CF$_3$, OH, and O—CH$_3$,
R$^3$ is selected from the group consisting of H, F, Cl, CH$_3$, and O—CH$_3$,
Z represents N and
R$^{4a}$ represents H,
or
Z represents C—R$^{4b}$,
wherein R$^{4b}$ represents H or CH$_3$, and
R$^{4a}$ represents H,
R$^5$ represents H,
X represents N or CH,
R$^6$ represents CF$_3$, tert.-Butyl or cyclopropyl,
R$^7$ represents H, CH$_3$, C$_2$H$_5$ or C$_4$H$_9$, and
R$^8$ represents a saturated C$_{1-4}$ aliphatic residue, unsubstituted cyclohexyl, unsubstituted phenyl or phenyl monosubstituted with F or Cl,
or
R$^7$ and R$^8$ together represent —(CH$_2$)$_{3-5}$—, —(CH$_2$)$_o$—C(R$^{100}$)$_2$—(CH$_2$)$_p$—, —(CH$_2$)$_2$-Q-(CH$_2$)$_2$—, or —CH$_2$—CH(CH$_3$)—O—CH(CH$_3$)—CH$_2$—;
wherein p represents 0, 1 or 2;
o represents 1, 2 or 3; and
the total of o +p equals from 2 to 4;
each R$^{100}$ independently represents H, CH$_3$, F, OCH$_3$, N(CH$_3$)$_2$, CH$_2$—OCH$_3$, CH$_2$—N(CH$_3$)$_2$, benzyl, phenyl, C(=O)-phenyl, wherein phenyl is unsubstituted or monosubstituted with F or Cl,
or two groups R$^{100}$ together represent —O—N=CHR$^{101}$—CH$_2$—;
wherein R$^{101}$ represents t-butyl or phenyl; and
Q represents O or NR$^{102}$;
wherein R$^{102}$ represents H, CH$_3$, phenyl or pyridyl.

Particularly preferred are compounds according to the invention from the group
1  N-((2-(4-methylpiperidin-1-yl)-6-(trifluoromethyl)pyridin-3-yl)methyl)-2-(3-(methylsulfonamidomethyl)phenyl)propanamide;
2  2-(3-(methylsulfonamidomethyl)phenyl)-N-((2-(pyrrolidin-1-yl)-6-(trifluoromethyl)pyridin-3-yl)methyl)propanamide;
3  2-(4-(methylsulfonamidomethyl)phenyl)-N-((2-(pyrrolidin-1-yl)-6-(trifluoromethyl)pyridin-3-yl)methyl)propanamide;
4  N-(4-(3-((2-(pyrrolidin-1-yl)-6-(trifluoromethyl)pyridin-3-yl)methyl)ureido)benzyl)methanesulfonamide;
5  N-(4-(3-((2-(4-methylpiperidin-1-yl)-6-(trifluoromethyl)pyridin-3-yl)methyl)ureido)benzyl)methanesulfonamide;
6  N-((2-(4-methylpiperidin-1-yl)-6-(trifluoromethyl)pyridin-3-yl)methyl)-2-(4-(methylsulfonamidomethyl)phenyl)propanamide;
7  N-((2-(dimethylamino)-6-(trifluoromethyl)pyridin-3-yl)methyl)-2-(3-fluoro-4-(methylsulfonamidomethyl)phenyl)propanamide;
8  N-((2-(ethylamino)-6-(trifluoromethyl)pyridin-3-yl)methyl)-2-(3-fluoro-4-(methylsulfonamidomethyl)phenyl)propanamide;
9  N-((2-(butylamino)-6-(trifluoromethyl)pyridin-3-yl)methyl)-2-(3-fluoro-4-(methylsulfonamidomethyl)phenyl)propanamide;
10  N-((2-(cyclohexylamino)-6-(trifluoromethyl)pyridin-3-yl)methyl)-2-(3-fluoro-4-(methylsulfonamidomethyl)phenyl)propanamide;
11  2-(3-fluoro-4-(methylsulfonamidomethyl)phenyl)-N-((2-(4-fluorophenylamino)-6-(trifluoromethyl)pyridin-3-yl)methyl)propanamide;
12  N-((2-(butyl(methypamino)-6-(trifluoromethyl)pyridin-3-yl)methyl)-2-(3-fluoro-4-(methylsulfonamidomethyl)phenyl)propanamide;
13  N-((2-(3,3-difluoroazetidin-1-yl)-6-(trifluoromethyl)pyridin-3-yl)methyl)-2-(3-fluoro-4-(methylsulfonamidomethyl)phenyl)propanamide;
14  2-(3-fluoro-4-(methylsulfonamidomethyl)phenyl)-N-((2-(3-methoxyazetidin-1-yl)-6-(trifluoromethyl)pyridin-3-yl)methyl)propanamide;
15  N-(2-fluoro-4-(3-((2-(pyrrolidin-1-yl)-6-(trifluoromethyl)pyridin-3-yl)methyl)ureido)benzyl)methanesulfonamide;
16  2-(3-fluoro-4-(methylsulfonamidomethyl)phenyl)-N-((2-(pyrrolidin-1-yl)-6-(trifluoromethyl)pyridin-3-yl)methypacetamide;
17  2-(3-fluoro-4-(methylsulfonamidomethyl)phenyl)-N-((2-(pyrrolidin-1-yl)-6-(trifluoromethyl)pyridin-3-yl)methyl)propanamide;
18  2-(3-fluoro-4-(methylsulfonamidomethyl)phenyl)-N-((2-(2-methylpyrrolidin-1-yl)-6-(trifluoromethyl)pyridin-3-yl)methyl)propanamide;
19  N-((2-((S)-3-(dimethylamino)pyrrolidin-1-yl)-6-(trifluoromethyl)pyridin-3-yl)methyl)-2-(3-fluoro-4-(methylsulfonamidomethyl)phenyl)propanamide;
20  N-((2-((R)-3-(dimethylamino)pyrrolidin-1-yl)-6-(trifluoromethyl)pyridin-3-yl)methyl)-2-(3-fluoro-4-(methylsulfonamidomethyl)phenyl)propanamide;
21  2-(3-fluoro-4-(methylsulfonamidomethyl)phenyl)-N-((2-(piperidin-1-yl)-6-(trifluoromethyl)pyridin-3-yl)methyl)propanamide;
22  2-(3-fluoro-4-(methylsulfonamidomethyl)phenyl)-N-((2-(4-fluoropiperidin-1-yl)-6-(trifluoromethyl)pyridin-3-yl)methyl)propanamide;
23  2-(3-fluoro-4-(methylsulfonamidomethyl)phenyl)-N-((2-(4-methoxypiperidin-1-yl)-6-(trifluoromethyl)pyridin-3-yl)methyl)propanamide;
24  N-(2-fluoro-4-(3-((2-(4-methyl piperidin-1-yl)-6-(trifluoromethyl)pyridin-3-yl)methyl)ureido)benzyl)methanesulfonamide;
25  2-(3-fluoro-4-(methylsulfonamidomethyl)phenyl)-N-((2-(4-methylpiperidin-1-yl)-6-(trifluoromethyl)pyridin-3-yl)methypacetamide;
26  N-((6-cyclopropyl-2-(4-methylpiperidin-1-yl)pyridin-3-yl)methyl)-2-(3-fluoro-4-(methylsulfonamidomethyl)phenyl)propanamide;
27  N-(4-tert-butyl-2-(4-methylpiperidin-1-yl)benzyl)-2-(3-fluoro-4-(methylsulfonamidomethyl)phenyl)propanamide;
28  N-((6-tert-butyl-2-(4-methylpiperidin-1-yl)pyridin-3-yl)methyl)-2-(3-fluoro-4-(methylsulfonamidomethyl)phenyl)propanamide;
29  2-(3-fluoro-4-(methylsulfonamidomethyl)phenyl)-N-(2-(4-methylpiperidin-1-yl)-4-(trifluoromethyl)benzyl)propanamide;
30  2-(3-fluoro-4-(methylsulfonamidomethyl)phenyl)-N-((2-(4-methylpiperidin-1-yl)-6-(trifluoromethyl)pyridin-3-yl)methyl)propanamide;

31 2-(3-fluoro-4-(methylsulfonamidomethyl)phenyl)-N-((2-(4-(methoxymethyl)piperidin-1-yl)-6-(trifluoromethyl)pyridin-3-yl)methyl)propanamide;

32 2-(3-fluoro-4-(methylsulfonamidomethyl)phenyl)-N-((2-(4-phenylpiperidin-1-yl)-6-(trifluoromethyl)pyridin-3-yl)methyl)propanamide;

33 N-((2-(4-benzylpiperidin-1-yl)-6-(trifluoromethyl)pyridin-3-yl)methyl)-2-(3-fluoro-4-(methylsulfonamidomethyl)phenyl)propanamide;

34 N-((2-(4-(dimethylamino)-4-phenylpiperidin-1-yl)-6-(trifluoromethyl)pyridin-3-yl)methyl)-2-(3-fluoro-4-(methylsulfonamidomethyl)phenyl)propanamide;

35 2-(3-fluoro-4-(methylsulfonamidomethyl)phenyl)-N-((2-morpholino-6-(trifluoromethyl)pyridin-3-yl)methyl)propanamide;

36 N-((2-((2S,6R)-2,6-dimethylmorpholino)-6-(trifluoromethyl)pyridin-3-yl)methyl)-2-(3-fluoro-4-(methylsulfonamidomethyl)phenyl)propanamide;

37 2-(3-fluoro-4-(methylsulfonamidomethyl)phenyl)-N-((2-(4-methylpiperazin-1-yl)-6-(trifluoromethyl)pyridin-3-yl)methyl)propanamide;

38 2-(3-fluoro-4-(methylsulfonamidomethyl)phenyl)-N-((2-(4-phenylpiperazin-1-yl)-6-(trifluoromethyl)pyridin-3-yl)methyl)propanamide;

39 2-(3-fluoro-4-(methylsulfonamidomethyl)phenyl)-N-((2-(4-(pyridin-2-yl)piperazin-1-yl)-6-(trifluoromethyl)pyridin-3-yl)methyl)propanamide;

40 N-((2-(4-((dimethylamino)methyl)piperidin-1-yl)-6-(trifluoromethyl)pyridin-3-yl)methyl)-2-(3-fluoro-4-(methylsulfonamidomethyl)phenyl)propanamide;

41 2-(3-fluoro-4-(methylsulfonamidomethyl)phenyl)-N-((2-(4-(4-fluorobenzoyl)piperidin-1-yl)-6-(trifluoromethyl)pyridin-3-yl)methyl)propanamide;

42 N-((2-(3-tert-butyl-1-oxa-2,8-diazaspiro[4.5]dec-2-en-8-yl)-6-(trifluoromethyl)pyridin-3-yl)methyl)-2-(3-fluoro-4-(methylsulfonamidomethyl)phenyl)propanamide;

43 2-(3-fluoro-4-(methylsulfonamidomethyl)phenyl)-N-((2-(3-phenyl-1-oxa-2,8-diazaspiro[4.5]dec-2-en-8-yl)-6-(trifluoromethyl)pyridin-3-yl)methyl)propanamide;

44 N-(2,6-difluoro-4-(3-((2-(4-methylpiperidin-1-yl)-6-(trifluoromethyl)pyridin-3-yl)methyl)ureido)benzyl)methanesulfonamide;

45 2-(3-chloro-4-(methylsulfonamidomethyl)phenyl)-N-((2-(pyrrolidin-1-yl)-6-(trifluoromethyl)pyridin-3-yl)methyl)propanamide;

46 2-(3-chloro-4-(methylsulfonamidomethyl)phenyl)-N-((2-(4-methylpiperidin-1-yl)-6-(trifluoromethyl)pyridin-3-yl)methyl)propanamide;

47 N-(2-hydroxy-4-(3-((2-(4-methylpiperidin-1-yl)-6-(trifluoromethyl)pyridin-3-yl)methyl)ureido)benzyl)methanesulfonamide;

48 2-(3-methoxy-4-(methylsulfonamidomethyl)phenyl)-N-((2-(pyrrolidin-1-yl)-6-(trifluoromethyl)pyridin-3-yl)methyl)propanamide;

49 N-(2-methoxy-4-(3-((2-(4-methylpiperidin-1-yl)-6-(trifluoromethyl)pyridin-3-yl)methyl)ureido)benzyl)methanesulfonamide;

50 2-(3-methoxy-4-(methylsulfonamidomethyl)phenyl)-N-((2-(4-methylpiperidin-1-yl)-6-(trifluoromethyl)pyridin-3-yl)methyl)propanamide;

51 2-(3-methyl-4-(methylsulfonamidomethyl)phenyl)-N-((2-(pyrrolidin-1-yl)-6-(trifluoromethyl)pyridin-3-yl)methyl)propanamide;

52 N-(2-methyl-4-(3-((2-(pyrrolidin-1-yl)-6-(trifluoromethyl)pyridin-3-yl)methyl)ureido)benzyl)methanesulfonamide;

53 N-(2-methyl-4-(3-((2-(4-methylpiperidin-1-yl)-6-(trifluoromethyl)pyridin-3-yl)methyl)ureido)benzyl)methanesulfonamide;

54 2-(4-(ethylsulfonamidomethyl)-3-fluorophenyl)-N-((2-(pyrrolidin-1-yl)-6-(trifluoromethyl)pyridin-3-yl)methyl)propanamide;

55 2-(4-(ethylsulfonamidomethyl)-3-fluorophenyl)-N-((2-(4-methylpiperidin-1-yl)-6-(trifluoromethyl)pyridin-3-yl)methyl)propanamide;

56 1-{[2-pyrrolidin-1-yl-6-(trifluoromethyl)pyridin-3-yl]methyl}-3-{4-[(sulfamoylamino)methyl]phenyl}propanamide;

57 1-{[2-pyrrolidin-1-yl-6-(trifluoromethyl)pyridin-3-yl]methyl}-3-{4-[(sulfamoylamino)methyl]phenyl}urea;

58 N-((2-(4-methylpiperidin-1-yl)-6-(trifluoromethyl)pyridin-3-yl)methyl)-2-(4-((sulfamoylamino)methyl)phenyl)propanamide;

59 1-{[2-(4-methylpiperidin-1-yl)-6-(trifluoromethyl)pyridin-3-yl]methyl}-3-{4-[(sulfamoylamino)methyl]phenyl}urea;

60 1-{3-fluoro-4-[(sulfamoylamino)methyl]phenyl}-3-{[2-pyrrolidin-1-yl-6-(trifluoromethyl)pyridin-3-yl]methyl}urea;

61 1-{3-fluoro-4-[(sulfamoylamino)methyl]phenyl}-3-{[2-(4-methylpiperidin-1-yl)/-6-(trifluoromethyl)pyridin-3-yl]methyl}urea;

62 2-(3-fluoro-4-((N-methylmethylsulfonamido)methyl)phenyl)-N-((2-(pyrrolidin-1-yl)-6-(trifluoromethyl)pyridin-3-yl)methyl)propanamide;

63 2-(3-fluoro-4-((N-methylmethylsulfonamido)methyl)phenyl)-N-((2-(4-methylpiperidin-1-yl)-6-(trifluoromethyl)pyridin-3-yl)methyl)propanamide;

64 2-(3-fluoro-4-((sulfamoylamino)methyl)phenyl)-N-((2-(4-methylpiperidin-1-yl)-6-(trifluoromethyl)pyridin-3-yl)methyl)propanamide;

65 N-(2-fluoro-5-(3-((2-(4-methylpiperidin-1-yl)-6-(trifluoromethyl)pyridin-3-yl)methyl)ureido)benzyl)methanesulfonamide;

66 2-(4-fluoro-3-(methylsulfonamidomethyl)phenyl)-N-((2-(4-methylpiperidin-1-yl)-6-(trifluoromethyl)pyridin-3-yl)methyl)propanamide;

67 N-((2-(piperidin-1-yl)-6-(trifluoromethyl)pyridin-3-yl)methyl)-2-(4-((sulfamoylamino)methyl)phenyl)propanamide;

68 2-(3-fluoro-4-((sulfamoylamino)methyl)phenyl)-N-((2-(piperidin-1-yl)-6-(trifluoromethyl)pyridin-3-yl)methyl)propanamide;

69 (S)—N-((2-(piperidin-1-yl)-6-(trifluoromethyl)pyridin-3-yl)methyl)-2-(4-((sulfamoylamino)methyl)phenyl)propanamide;

70 (R)—N-((2-(piperidin-1-yl)-6-(trifluoromethyl)pyridin-3-yl)methyl)-2-(4-((sulfamoylamino)methyl)phenyl)propanamide;

71 (S)-2-(3-fluoro-4-((sulfamoylamino)methyl)phenyl)-N-((2-(piperidin-1-yl)-6-(trifluoromethyl)pyridin-3-yl)methyl)propanamide; and 72 (R)-2-(3-fluoro-4-((sulfamoylamino)methyl)phenyl)-N-((2-(piperidin-1-yl)-6-(trifluoromethyl)pyridin-3-yl)methyl)propanamide;

optionally in the form of a single stereoisomer or a mixture of stereoisomers, in the form of the free compound and/or a physiologically acceptable salt thereof.

Furthermore, preference may be given to compounds according to the invention that cause a 50 percent displacement of capsaicin, which is present at a concentration of 100 nM, in a FLIPR assay with CHO K1 cells which were transfected with the human VR1 gene at a concentration of less than 2,000 nM, preferably less than 1,000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA), as described hereinafter.

The substituted compounds according to the invention of the aforementioned general formula (I) and corresponding stereoisomers and also the respective corresponding acids, bases, salts and solvates are toxicologically safe and are therefore suitable as pharmaceutical active ingredients in pharmaceutical compositions.

The present invention therefore further relates to a pharmaceutical composition containing at least one compound according to the invention of the above-indicated formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a corresponding salt, or respectively in the form of a corresponding solvate, and also if appropriate optionally one or more pharmaceutically compatible auxiliaries.

These pharmaceutical compositions according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation, i.e. they exert an agonistic or antagonistic effect.

Likewise, the pharmaceutical compositions according to the invention are preferably suitable for the prophylaxis and/or treatment of disorders or diseases which are mediated, at least in part, by vanilloid receptors 1.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of the above-indicated formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragees, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

The pharmaceutical composition according to the invention is preferably suitable for the treatment and/or prophylaxis of one or more disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the pharmaceutical composition according to the invention is suitable for the treatment and/or prophylaxis of one or more disorders and/or diseases selected from the group consisting of pain, preferably of pain selected from the group consisting of acute pain, chronic pain, neuropathic pain, visceral pain and joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, the pharmaceutical composition according to the invention is suitable for the treatment and/or prophylaxis of pain, preferably of pain selected from the group consisting of acute pain, chronic pain, neuropathic pain and visceral pain.

The present invention further relates to a substituted compound according to general formula (I) and also if appropriate to a substituted compound according to general formula (I) and one or more pharmaceutically acceptable auxiliaries for use in vanilloid receptor 1-(VR1/TRPV1) regulation, preferably for use in vanilloid receptor 1-(VR1/TRPV1) inhibition and/or vanilloid receptor 1-(VR1/TRPV1) stimulation.

The present invention therefore further relates to a substituted compound according to general formula (I) and also if appropriate to a substituted compound according to general formula (I) and one or more pharmaceutically acceptable auxiliaries for use in the prophylaxis and/or treatment of disorders and/or diseases which are mediated, at least in part, by vanilloid receptors 1.

In particular, the present invention therefore further relates to a substituted compound according to general formula (I) and also if appropriate to a substituted compound according to general formula (I) and one or more pharmaceutically acceptable auxiliaries for use in the prophylaxis and/or treatment of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particularly preferred is a substituted compound according to general formula (I) and also if appropriate to a substituted compound according to general formula (I) and one or more pharmaceutically acceptable auxiliaries for use in the prophylaxis and/or treatment of pain, preferably of pain selected from the group consisting of acute pain, chronic pain, neuropathic pain and visceral pain.

The present invention further relates to the use of at least one compound according to general formula (I) and also if appropriate of one or more pharmaceutically acceptable auxiliaries for the preparation of a pharmaceutical composition for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further for the prophylaxis and/or treatment of disorders and/or diseases which are mediated, at least in part, by vanilloid receptors 1, such as e.g. disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system;

for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Another aspect of the present invention is a method for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further, a method of treatment and/or prophylaxis of disorders and/or diseases, which are mediated, at least in part, by vanilloid receptors 1, in a mammal, preferably of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour und Smith (J. Pharm. Exp. Ther. 72, 74 79 (1941)) or by the formalin test (e.g. according to D. Dubuisson et al., Pain 1977, 4, 161-174).

The present invention further relates to processes for preparing inventive compounds of the above-indicated general formula (I).

All reactions which can be applied for synthesizing the compounds according to the present invention can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps of the reaction sequences which can be applied for synthesizing the compounds according to the present invention as well as the respective purification and/or isolation of intermediate or end products, can be carried out partly or completely under an inert gas atmosphere, preferably under a nitrogen atmosphere.

The substituted compounds according to the invention can be isolated both in the form of their free bases, their free acids and also in the form of corresponding salts, in particular physiologically compatible salts, i.e. physiologically acceptable salts.

The free bases of the respective substituted compounds according to the invention can be converted into the corresponding salts, preferably physiologically compatible salts, for example by reaction with an inorganic or organic acid, preferably with hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective substituted compounds of the aforementioned general formula (I) and of corresponding stereoisomers can likewise be converted into the corresponding physiologically compatible salts using the free acid or a salt of a sugar additive, such as for example saccharin, cyclamate or acesulphame.

Accordingly, the free acids of the substituted compounds according to the invention can be converted into the corresponding physiologically compatible salts by reaction with a suitable base. Examples include the alkali metal salts, alkaline earth metals salts or ammonium salts $[NH_xR_{4-x}]^+$, in which $x=0$, 1, 2, 3 or 4 and R represents a branched or unbranched $C_{1-4}$ aliphatic residue.

The substituted compounds according to the invention and of corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds according to the invention are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

The chemicals and reaction components used in the reactions and schemes described below are available commercially or in each case can be prepared by conventional methods known to the person skilled in the art.

The methods with which the person skilled in the art is familiar for carrying out the reaction steps for preparing the compounds according to the invention may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

The invention will be described hereinafter with the aid of a number of examples. This description is intended merely by way of example and does not limit the general idea of the invention.

EXAMPLES

The indication "equivalents" ("eq." or "eq") means molar equivalents, "RT" or "rt" means room temperature (23±7° C.), "M" are indications of concentration in mol/l, "aq." means aqueous, "sat." means saturated, "sol." means solution, "conc." means concentrated.

| Further abbreviations: | |
|---|---|
| ACN | acetonitrile |
| BH$_3$•SMe$_2$ | borane-methyl sulfide complex |
| bipy | 2,2'-bipyridine/2,2'-bipyridyl |
| Boc | tert-butyloxycarbonyl |
| Boc$_2$O | di-tert-butyl dicarbonate |
| brine | saturated aqueous sodium chloride solution |
| n-BuLi | n-butyllithium |
| t-BuOH | t-butanol |
| CC | column chromatography on silica gel |
| d | days |
| DCM | dichloromethane |
| DETA | diethylentriamine |
| DMAP | 4-dimethylaminopyridine |
| DMF | N,N-dimethylformamide |
| EDC | N-(3-dimethylaminopropyl)-N'-ethylcarbodiimide |
| ether | diethyl ether |
| EtOAc | ethyl acetate |
| EtOH | ethanol |
| h | hour(s) |
| GC | gas chromatography |
| H$_2$O | water |
| H$_2$SO$_4$ | sulfuric acid |
| HOBt | 1-hydroxybenzotriazole |
| m/z | mass-to-charge ratio |
| MeOH | methanol |
| min | minutes |
| MS | mass spectrometry |
| NaH | sodium hydride |

| Further abbreviations: | |
|---|---|
| NBS | N-bromosuccinimide |
| TEA | triethylamine |
| NiBr$_2$ bipy | complex of nickel(II) bromide and 2,2'-bipyridine |
| NiCl$_2$•6H$_2$O | nickel(II) chloride hexahydride |
| Pd/C | palladium on charcoal |
| Pd(PPh$_3$)$_4$ | tetrakis(triphenylphosphine)palladium(0) |
| TBTU | O-(1H-benzotriazol-1-yl)-N,N,N',N'-tetramethyluronium tetrafluoroborate |
| TEA | triethylamine |
| TFA | trifluoroacetic acid |
| Tf2O | triflic anhydride |
| TLC | thin layer chromatography |
| THF | tetrahydrofuran |
| v/v | volume to volume |
| w/w | weight in weight |

The yields of the compounds prepared were not optimized. All temperatures are uncorrected.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington DC, US, respectively, for example) or the synthesis thereof has already been described precisely in the specialist literature (experimental guidelines can be found in the Reaxys® Database of Elsevier, Amsterdam, NL or the SciFinder® Database of the ACS, Washington DC, US, repspectively, for example) or can be prepared using the conventional methods known to the person skilled in the art.

The stationary phase used for the column chromatography was silica gel 60 (0.04-0.063 mm) from E. Merck, Darmstadt.

The mixing ratios of solvents or eluents for chromatography are specified in v/v.

All the intermediate products and exemplary compounds were analytically characterized by means of $^1$H—NMR spectroscopy. In addition, mass spectrometry tests (MS, m/z for [M+H]$^+$) were carried out for all the exemplary compounds and selected intermediate products.

Synthesis of the Exemplary Compounds:

The exemplary compounds 1-6, 8-9, 14, 17, 21, 24-25, 28-30, 34-35, 45-61 and 63-66 were obtained by one of the methods disclosed before or thereafter. The exemplary compounds 7, 10-13, 15-16, 18-20, 22-23, 26-27, 31-33, 36-44, 62 as well as 67-72 can be obtained by one of the methods disclosed before or thereafter. The person skilled in the art is aware which method has to be employed to obtain a particular exemplary compound.

Detailed Synthesis of Selected Exemplary Compounds

Synthesis of Example 1

—N-((2-(4-methylpiperidin-1-yl)-6-(trifluoromethyl)pyridin-3-yl)methyl)-2-(3-(methylsulfonamidomethyl)phenyl)propanamide

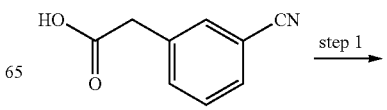

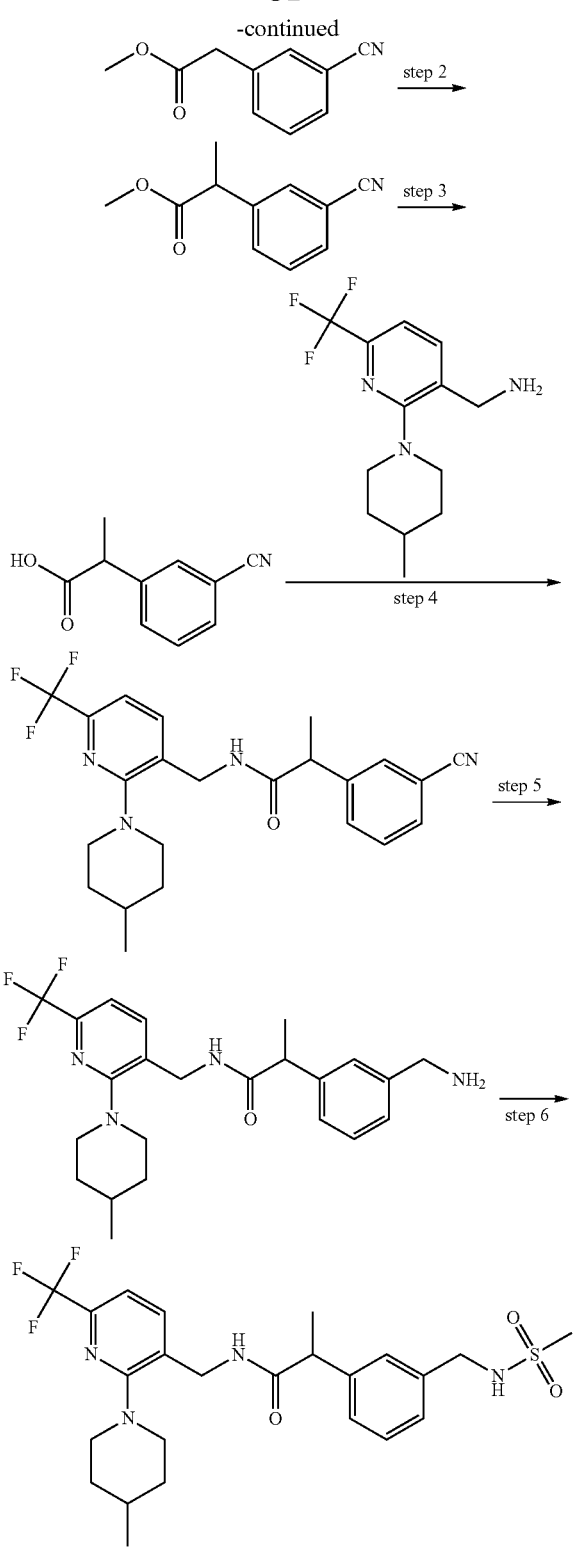

Step 1: To the solution of 2-(3-cyanophenyl)acetic acid (700 mg, 43.4 mmol) in methanol was slowly added sulfuric acid (0.42 mL, 4.34 mmol) at room temperature. The reaction mixture was refluxed for 3 h at 70° C. under nitrogen atmosphere. TLC showed complete consumption of starting material. The reaction mixture was cooled to room temperature. Solvent was removed in vacuo and extracted with ethyl acetate. The organic part was washed with brine. The organic layer was dried over magnesium sulfate and concentrated under reduced pressure to afford crude product which was purified by column chromatography to afford methyl 2-(3-cyanophenyl)acetate (660 mg, 84%).

Step 2: To the cooled solution of sodium hydride (91 mg, 2.285 mmol, 60% suspension in oil) in anhydrous tetrahydrofuran was added a solution of methyl 2-(3-cyanophenyl)acetate (400 mg, 2.285 mmol) drop wise at 0° C. Reaction mixture was stirred at room temperature for 1 h. TLC showed complete consumption of starting material. The reaction mixture was quenched with brine and extracted with ethyl acetate. The organic part was washed with brine. The organic layer was dried over magnesium sulfate and concentrated under reduced pressure to afford crude product which was purified by column chromatography to afford methyl 2-(3-cyanophenyl)propanoate (180 mg, 48%).

Step 3: A solution of methyl 2-(3-cyanophenyl)propanoate (180 mg, 9 mmol) in water and tetrahydrofuran (1:2, 30 mL) was treated with lithium hydroxide (27 mmol) at 0° C. and stirred for 2 h at room temperature. The mixture was diluted with water and dichloromethane, acidified with 1 N HCl solution and extracted with dichloromethane several times. The combined organic layers were washed with water and brine, dried over magnesium sulfate and concentrated in vacuo which offered 2-(3-cyanophenyl)propanoic acid (147 mg, 88%).

Step 4: A solution of 2-(3-cyanophenyl)propanoic acid (7 4mg, 42.2 mmol) in 1,4-dioxane was cooled in an ice bath and N-(3-dimethylaminopropyl)-N'-ethylcarbodiimide (120 mg, 63.2 mmol), 1-hydroxybenzotriazole (85 mg, 63.2 mmol), triethylamine (127 μL, 126 mmol) and (2-(4-methylpiperidin-1-yl)-6-(trifluoromethyl)pyridin-3-yl)methanamine (115 mg, 42.2 mmol) were added consecutively. The reaction mixture was stirred overnight at room temperature. Water was added to the reaction mixture and extracted with dichloromethane. The combined organic extracts were washed successively with saturated NaHCO₃ solution, 0.5 N HCl and water and dried over magnesium sulfate. Evaporation of the solvent followed by column chromatographic purification afforded the desired 2-(3-cyanophenyl)-N-((2-(4-methylpiperidin-1-yl)-6-(trifluoromethyl)pyridin-3-yl)methyl)propanamide (100 mg, 52%).

Step 5: To a stirred solution of 2-(3-cyanophenyl)-N-((2-(4-methylpiperidin-1-yl)-6-(trifluoromethyl)pyridin-3-yl)methyl)propanamide (100 mg, 23.2 mmol) in dry ethanol (15 mL), cooled to 0° C. were added nickel(II) chloride hexahydride (55 mg, 23.2 mmol). Sodium borohydride (52 mg, 139 mmol) was added in small portions over 10 min. The reaction mixture was allowed to warm to room temperature and stirred for a further 1 h. The purple residue was dissolved in ethyl acetate (50 mL) and extracted with saturated NaHCO₃. The organic layer was dried over magnesium sulfate and the solvent removed in vacuo to yield 2-(3-(aminomethyl)phenyl)-N-((2-(4-methyl piperidin-1-yl)-6-(trifluoromethyl)pyrid in-3-yl)methyl)propanamide (100 mg, 58%).

Step 6: To a cooled solution of 2-(3-(aminomethyl)phenyl)-N-((2-(4-methylpiperidin-1-yl)-6-(trifluoromethyl)pyridin-3-yl)methyl)propanamide (100 mg, 23 mmol) in dichloromethane was added triethylamine (51 μL, 46 mmol) at 0° C. The resulting solution was treated dropwise with methanesulfonyl chloride (26.4 μL, 34.6 mmol) over 10 min and stirred for 1 h at room temperature. After aqueous workup, the residue was purified by flash column chromatography to obtain N-((2-(4-methylpiperidin-1-yl)-

6-(trifluoromethyl)pyridin-3-yl)methyl)-2-(3-(methylsulfonamidomethyl)phenyl)propanamide (example 1) (61 mg, 57%).

$^1$H NMR (300 MHz, CD$_3$OD) δ 7.46 (d, 1H, J=6 Hz, Ar—H), 7.39-7.26 (m, 4H, Ar—H), 7.21 (d, 1H, J=9 Hz, Ar—H), 4.45 (q, 2H, Ar—CH$_2$), 4.23 (s, 2H, CH$_2$NHMs) 3.77 (q, 1H, CH$_3$_CH—), 3.39-3.35 (m, 2H, Piperidine), 2.82 (s, 3H, NHSO$_2$CH$_3$), 2.84-2.74 (m, 2H, Piperidine), 1.72-1.68 (m, 2H, Piperidine), 1.58-1.53 (m, 1H, Piperidine), 1.49 (d, 3H, —CH—CH$_3$), 1.38-1.25 (m, 2H, Piperidine), 0.99 (d, 3H, —CH—CH$_3$)

Synthesis of Example 2

-2-(3-(methylsulfonamidomethyl)phenyl)-N-((2-(pyrrolidin-1-yl)-6-(trifluoromethyl)pyridin-3-yl)methyl)propanamide

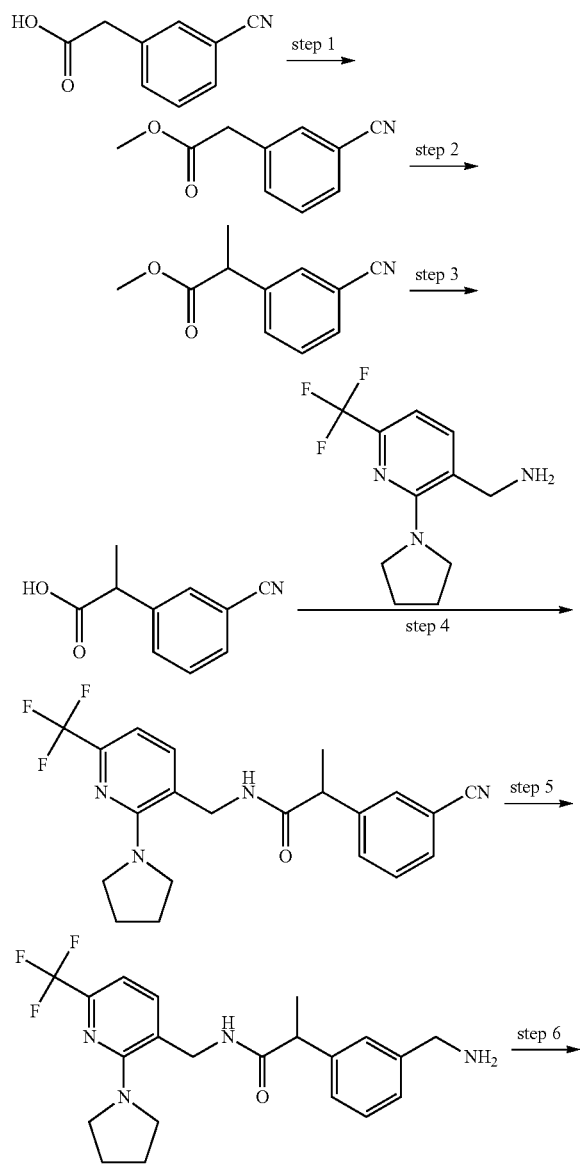

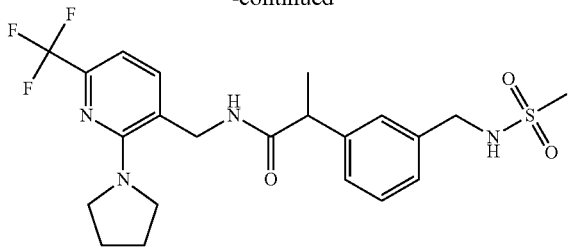

Step 1: To the solution 2-(3-cyanophenyl)acetic acid (700 mg, 43.4 mmol) in methanol was slowly added sulfuric acid (0.42 mL, 4.34 mmol, 0.1 eq) at room temperature. The reaction mixture was refluxed for 3 h at 70° C. under N$_2$. TLC showed complete consumption of starting material. The reaction mixture was cooled to room temperature. Solvent was removed in vacuo and extracted with ethylacetate. The organic part was washed with brine. The organic layer was dried over magnesium sulfate and concentrated under reduced pressure to afford crude product which was purified by column chromatography to afford methyl 2-(3-cyanophenyl)acetate (660 mg, 84%)

Step 2: To the cooled solution of sodium hydride (91 mg, 2.285 mmol, 60% suspension in oil) in anhydrous tetrahydrofuran was added solution of methyl 2-(3-cyanophenyl)acetate (400 mg, 2.285 mmol) dropwise at 0° C. Reaction mixture was stirred at room temperature for 1 h. TLC showed complete consumption of starting material. The reaction mixture was quenched with brine and extracted with ethylacetate. The organic part was washed with brine. The organic layer was dried over magnesium sulfate and concentrated under reduced pressure to afford crude product which was purified by column chromatography to afford methyl 2-(3-cyanophenyl)propanoate (180 mg, 48%)

Step 3: A solution of methyl 2-(3-cyanophenyl)propanoate (180 mg, 9 mmol) in water and tetrahydrofuran (1:2, 30 mL) was treated with lithium hydroxide (27 mmol) at 0° C. and stirred for 2 h at room temperature. The mixture was diluted with water and dichloromethane, acidified with 1 N HCl solution, and extracted with dichloromethane several times. The combined organic layers were washed with water and brine, dried over magnesium sulfate, and concentrated in vacuo which offered 2-(3-cyanophenyl)propanoic acid (147 mg, 88%)

Step 4: A solution of the 2-(3-cyanophenyl)propanoic acid (99 mg, 0.52 mmol) in dioxane was cooled in an ice bath and N-(3-dimethylaminopropyl)-N'-ethylcarbodiimide (148 mg, 0.78 mmol), 1-hydroxybenzotriazole (108 mg, 0.78 mmol), triethylamine (167 μl, 1.57 mmol) and the (2-(pyrrolidin-1-yl)-6-(trifluoromethyl)pyridin-3-yl) methanamine (137 mg, 0.52 mmol), were added consecutively. The reaction mixture was stirred overnight at room temperature. Water was added to the reaction mixture and extracted with dichloromethane. The combined organic extracts were washed successively with saturated NaHCO$_3$ solution, 0.5 N HCl and then water and dried over magnesium sulfate. Evaporation of the solvent followed by column chromatographic purification afforded the desired 2-(3-cyanophenyl)-N-((2-(pyrrolidin-1-yl)-6-(trifluoromethyl)pyridin-3-yl)methyl)propanamide (108 mg, 53%)

Step 5: To a stirred solution of 2-(3-cyanophenyl)-N-((2-(pyrrolidin-1-yl)-6-(trifluoromethyl)pyridin-3-yl)methyl)propanamide (95 mg, 0.236 mmol) in dry ethanol (15 mL), cooled to 0° C., were added NiCl$_2$.6 H$_2$O (56 mg, 0.236 mmol). Sodium borohydride (62 mg, 1.65 mmol) was then added in small portions over 10 min. The reaction was exothermic and effervescent. The reaction mixture was allowed to warm to room temperature and left to stir for a further 1 h, the purple residue was dissolved in ethyl acetate (50 mL) and extracted with saturated NaHCO₃. The organic layer was dried over magnesium sulfate and the solvent removed in vacuo to yield 2-(3-(aminomethyl)phenyl)-N-((2-(pyrrolidin-1-yl)-6-(trifluoromethyl)pyridin-3-yl)methyl)propanamide (108 mg, 60%).

Step 6: A cooled solution of 2-(3-(aminomethyl)phenyl)-N-((2-(pyrrolidin-1-yl)-6-(trifluoromethyl)pyridin-3-yl)methyl)propanamide (75 mg, 0.18 mmol) in dichloromethane was added triethylamine (22 μL, 0.22 mmol) at 0° C. resulting solution was treated dropwise with methanesulfonyl chloride (25.4 μl, 0.221 mmol) over 10 min and stirred for 1 h at room temperature. After aqueous workup, the residue was purified by flash column chromatography to obtain 2-(3-(methylsulfonamidomethyl)phenyl)-N-((2-(pyrrolidin-1-yl)-6-(trifluoromethyl)pyridin-3-yl)methyl)propanamide (example 2) (61 mg, 60%)

¹H NMR (300 MHz, CD₃OD) δ 8.30 (bs, 1H, NH), 7.39-7.25 (m, 5H, Ar—H), 6.91-6.89 (d, 1H, J=6.0), 4.51-4.30 (dd, 2H, Ar—CH₂), 4.23 (s, 2H, CH₂NHMs) 3.75-3.68 (q, 1H, CH—CH₃), 3.49-3.41 (m, 4H), 2.82 (s, 3H, NHSO₂CH₃), 1.88-1.82 (m, 4H), 1.47-1.45 (d, 3H, J=6.0).

Synthesis of Example 3

-2-(4-(methylsulfonamidomethyl)phenyl)-N-((2-(pyrrolidin-1-yl)-6-(trifluoromethyl)pyridin-3-yl)methyl)propanamide

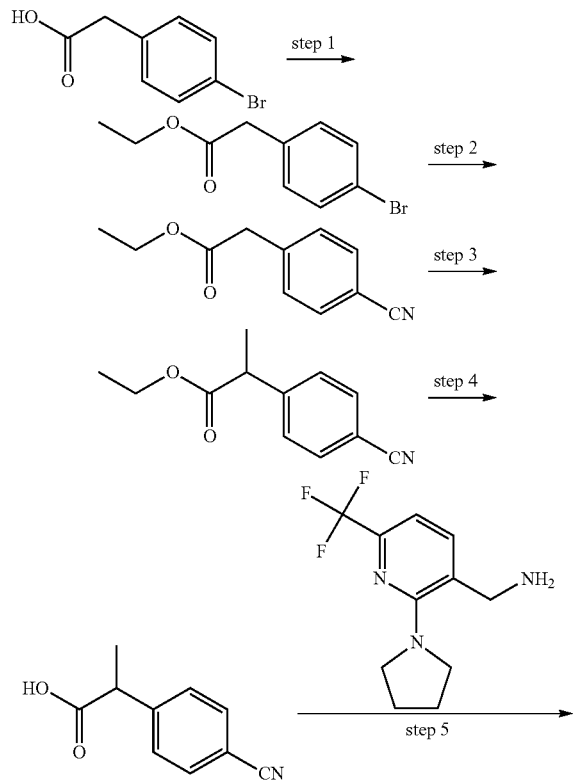

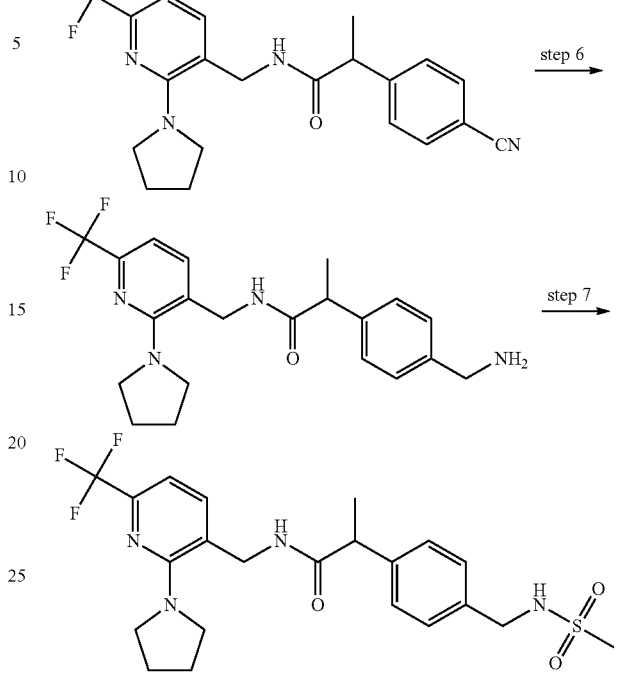

Step 1: To a solution of 2-(4-bromophenyl)acetic acid (3 g, 13.95 mmol) in ethanol was slowly added sulfuric acid (0.3 mL, cat.) at room temperature. The reaction mixture was heated to 100° C. for overnight. TLC showed complete consumption of starting material. The reaction mixture was cooled to room temperature and neutralized with NaHCO₃. The mixture was extracted with ethyl acetate and washed with water and brine. The extract was dried over magnesium sulfate and concentrated under reduced pressure to give ethyl 2-(4-bromophenyl)acetate (3.24 g, 96%).

Step 2: To a solution of ethyl 2-(4-bromophenyl)acetate (3.24 g, 13.32 mmol) in anhydrous dimethylformamide was added zinc cyanide (939 mg, 7.99 mmol), tetrakis(triphenylphosphine)palladium(0) (770 mg, 0.67 mmol). The reaction mixture was refluxed for overnight under N₂. TLC showed complete consumption of starting material. The mixture was filtered through celite bed and the filterate was concentrated under reduced pressure. The mixture was extracted with ethyl acetate and washed with water and brine. The extract was dried over magnesium sulfate and concentrated under reduced pressure to afford crude which was purified by column chromatography to afford ethyl 2-(4-(iminomethyl)phenyl)acetate. (962 mg, 38%)

Step 3: To a solution of ethyl 2-(4-(iminomethyl)phenyl)acetate (962 mg, 5.08 mmol) in anhydrous dimethylformamide was slowly added sodium hydride (224 g, 5.59 mmol) and iodomethane (0.33 mL, 5.34 mmol) at 0° C. The reaction mixture was heated to room temperature for 45 min under N₂. TLC showed complete consumption of starting material. The reaction mixture was added water for quenching. The mixture was extracted with ethyl acetate and washed with water and brine. The extract was dried over magnesium sulfate and concentrated under reduced pressure to afford crude which was purified by column chromatography to afford ethyl 2-(4-cyanophenyl)propanoate (832 mg, 81%)

Step 4: To a stirred solution of ethyl 2-(4-cyanophenyl)propanoate (832 mg, 4.09 mmol) in co-solvent with tetrahydrofuran and water (1:1) were added sodium hydroxide (409 mg, 10.23 mmol). The reaction mixture was stirred for overnight at room temperature, then acidified to pH 3~4 with acetic acid. The residue was diluted with ethyl acetate and washed with water and brine. The organic layer was dried over magnesium sulfate and filtered. The filtrate removed in vacuo. The crude 2-(4-cyanophenyl)propanoic acid (805 g) was obtained as 95% yield.

Step 5: To a stirred solution of 2-(4-cyanophenyl)propanoic acid (50 mg, 0.29 mmol) in acetonitrile were added N-(3-dimethylaminopropyl)-N'-ethylcarbodiimide (82 mg, 0.43 mmol), 1-hydroxybenzotriazole (58 mg, 0.43 mmol), (2-(pyrrolidin-1-yl)-6-(trifluoromethyl)pyridin-3-yl)methanamine (77 mg, 0.31 mmol) and triethylamine (0.10 mL, 0.71 mmol). The reaction mixture was stirred for overnight at room temperature. The mixture was diluted with ethyl acetate and washed with water and brine. The organic layer was dried over magnesium sulfate and filtered. The filtrate removed in vacuo. The crude was purified by column chromatography. 2-(4-cyanophenyl)-N-((2-(pyrrolidin-1-yl)-6-(trifluoromethyl)pyridin-3-yl)methyl)propanamide (56 mg) was obtained as 49% yield.

Step 6: To a stirred solution of 2-(4-cyanophenyl)-N-((2-(pyrrolidin-1-yl)-6-(trifluoromethyl)pyridin-3-yl)methyl)propanamide (56 mg, 0.14 mmol) in ethanol was cooled to 0° C. and added $NiCl_2.6 H_2O$ (33 mg, 0.14 mmol) and stirred more than 15 min. Sodium borohydride (37 mg, 0.97 mmol) was then added in small portions. The reaction was exothermic and effervescent. The resulting reaction mixture was allowed to warm to room temperature and left to stir for 2 h. The mixture was filtered using celite pad. The filtrate was concentrated was evaporated. The residue was dissolved in ethyl acetate and washed with water and brine, but when it does not separate easily, small amount of 1N HCl and saturated $NaHCO_3$ was used. The organic layer was dried over magnesium sulfate and filtered. The filtrate removed in vacuo. The crude was purified by column chromatography. 2-(4-(Aminomethyl)phenyl)-N-((2-(pyrrolidin-1-yl)-6-(trifluoromethyl)pyridin-3-yl)methyl)propanamide (58 mg) was obtained as 99% yield.

Step 7: To a stirred solution of 2-(4-(aminomethyl)phenyl)-N-((2-(pyrrolidin-1-yl)-6-(trifluoromethyl)pyridin-3-yl)methyl)propanamide (58 mg, 0.14 mmol) in pyridine was added methanesulfonylchloride (0.014 mL, 0.19 mmol) The reaction mixture was stirred for overnight at room temperature. The mixture was diluted with ethyl acetate and washed with 1N HCl and brine. The organic layer was dried over magnesium sulfate and filtered. The filtrate removed in vacuo. The crude was purified by column chromatography. 2-(4-(Methylsulfonamidomethyl)phenyl)-N-((2-(pyrrolidin-1-yl)-6-(trifluoromethyl)pyridin-3-yl)methyl)propanamide (example 3) (35 mg) was obtained as 51% yield.

$^1$H NMR (300 MHz, $CDCl_3$) δ 7.29-7.36 (m, 5H, Ar), 6.92 (d, 1H, J=7.5 Hz, Ar), 5.76 (bs, 1H, NH), 4.49 (bs, 1H, NH), 4.44 (t, 2H, J=4.95 Hz, $CH_2$), 4.29 (s, 2H, $CH_2$), 3.58 (m, 1H, CH), 3.41 (m, 4H, pyrrolidine), 2.91 (s, 3H, Ms), 1.84 (m, 4H, pyrrolidine), 1.52 (d, 3H, J=7.14 Hz, $CH_3$)

Synthesis of Example 4

—N-(4-(3-((2-(pyrrolidin-1-yl)-6-(trifluoromethyl)pyridin-3-yl)methyl)ureido)benzyl)methanesulfonamide

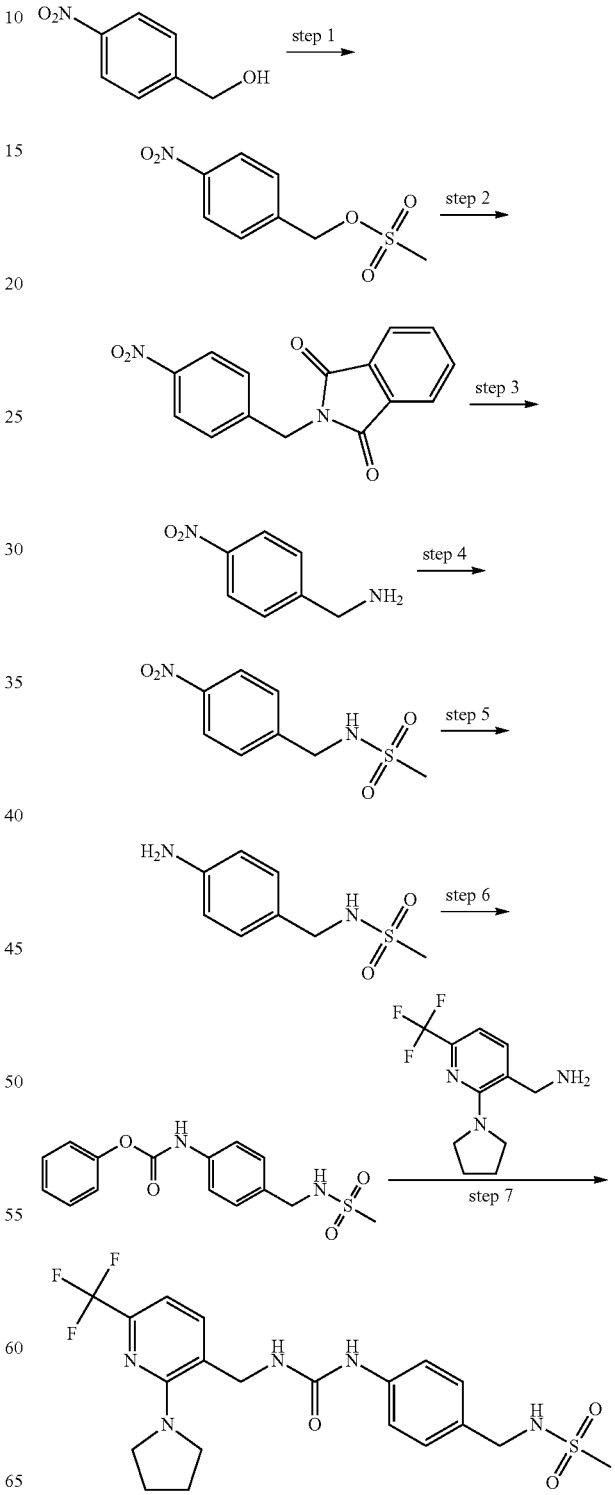

Step 1: To a solution of (4-nitrophenyl)methanol (2 g, 13.06 mmol) in toluene (10 mL) was slowly added methane sulfonylchloride (1.21 mL, 15.67 mmol) at room temperature. The reaction mixture was heated to 80° C. for 4 h. TLC showed complete consumption of starting material. The reaction mixture was cooled to room temperature. The mixture was extracted with ethyl acetate and washed with water and brine. The extract was dried over magnesium sulfate and concentrated under reduced pressure. The crude was purified by column chromatography to give 4-nitrobenzyl methanesulfonate (2.2 g, 72%).

Step 2: A solution of 4-nitrobenzyl methanesulfonate (2.2 g, 9.51 mmol) in dimethylformamide (10 mL) was added potassium phthalimide (1.9 g, 10.5 mmol) and stirred at room temperature for overnight. TLC showed complete consumption of starting material. The mixture was extracted with ethyl acetate and washed with water and brine. The extract was dried over magnesium sulfate and concentrated under reduced pressure. The crude was purified by crystallization to give 2-(4-nitrobenzyl)isoindoline-1,3-dione (1.6 g, 60%).

Step 3: 2-(4-Nitrobenzyl)isoindoline-1,3-dione (1.4 g, 4.96 mmol) was dissolved in tetrahydrofuran (8 mL). To the solution hydrazine monohydrate (1.48 mL, 19.84 mmol) and p-toluenesulfonic acid monohydrate (94 mg, 0.5 mmol) was added. It was refluxed for 6 h. TLC showed complete consumption of starting material. The mixture was extracted with ethyl acetate and washed with water and brine. The extract was dried over magnesium sulfate and concentrated under reduced pressure. The crude was purified by column chromatography to give (4-nitrophenyl)methanamine (651 mg, 86%).

Step 4: (4-Nitrophenyl)methanamine (651 mg, 4.28 mmol) was dissolved in pyridine (4 mL). The reaction mixture was added methane sulfonyl chloride (0.43 mL, 5.56 mmol) and stirred for 1 h at room temperature. TLC showed complete consumption of starting material. The mixture was diluted with 1N HCl and extracted with ethyl acetate. The extract was dried over magnesium sulfate and concentrated under reduced pressure. The crude was purified by column chromatography to give N-(4-nitrobenzyl)methanesulfonamide (881 mg, 89%).

Step 5: N-(4-Nitrobenzyl)methanesulfonamide (881 mg, 3.83 mmol) was dissolved in methanol/tetrahydrofuran (1:1, 35 mL). 10% Pd/C (264 mg, 3 eq) was added to it. The resulting mixture was stirred at room temperature for overnight under $H_2$. TLC showed complete consumption of starting material. The mixture was filtered through celite bed and the filerate was concentrated under reduced pressure. The crude was purified by column chromatography to give N-(4-aminobenzyl)methanesulfonamide (352 mg, 46%).

Step 6: N-(4-Aminobenzyl)methanesulfonamide (352 mg, 1.76 mmol) was dissolved in acetonitrile (3 mL) and tetrahydrofuran (4 mL). The reaction mixture was added pyridine (0.17 mL, 2.11 mmol) and phenyl chloroformate (0.23 mL, 1.85 mmol) and stirred at room temperature for 3 h under nitrogen atmosphere. TLC showed complete consumption of starting material. The reaction mixture was diluted with water and extracted with ethyl acetate. The organic part was washed with water and brine. The organic layer was dried over magnesium sulfate and concentrated under reduced pressure. The crude was purified by column chromatography to give phenyl 4-(methylsulfonamidomethyl)phenylcarbamate (438 mg, 78%).

Step 7: To a solution of phenyl 4-(methylsulfonamidomethyl) phenylcarbamate (57 mg, 0.18 mmol) in acetonitrile (3 mL) was added 4-dimethylaminopyridine (22 mg, 0.18 mmol) and (2-(pyrrolidin-1-yl)-6-(trifluoromethyl)pyridin-3-yl)methanamine (44 mg, 0.18 mmol) at room temperature. The reaction mixture was stirred at 50° C. for overnight. TLC showed complete consumption of starting material. The reaction mixture was diluted with water and extracted with ethyl acetate. The organic part was washed with water and brine. The organic layer was dried over magnesium sulfate and concentrated under reduced pressure. The crude was purified by column chromatography to give N-(4-(3-((2-(pyrrolidin-1-yl)-6-(trifluoromethyl)pyridin-3-yl)methyl)ureido)benzyl)methanesulfonamide (example 4) (59 mg, 70%).

$^1$H NMR (300 MHz, CD$_3$OD) δ 7.65 (d, 1 H, J=7.32 Hz, Ar—H), 7.32 (m, 4 H, Ar—H), 7.01 (d, 1H, J=7.5 Hz, Ar—H), 4.48 (s, 2 H, Ar—CH$_2$), 4.17 (s, 2 H, CH$_3$), 3.58 (m, 4 H, pyrrolidine-H), 2.81 (s, 3 H, Ms—CH$_3$), 1.96 (m, 4H, pyrrolidine-H)

Exemplary compound 15 can be prepared in a similar manner.

Synthesis of Example 5

—N-(4-(3-((2-(4-methylpiperidin-1-yl)-6-(trifluoromethyl)pyridin-3-yl)methyl)ureido)benzyl)methanesulfonamide

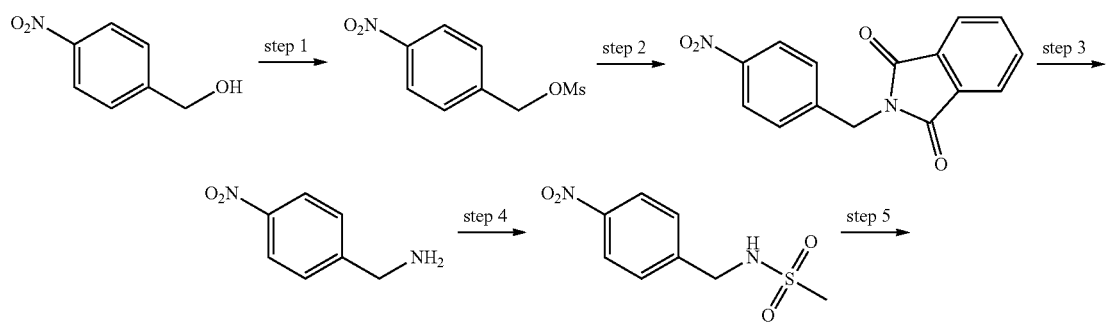

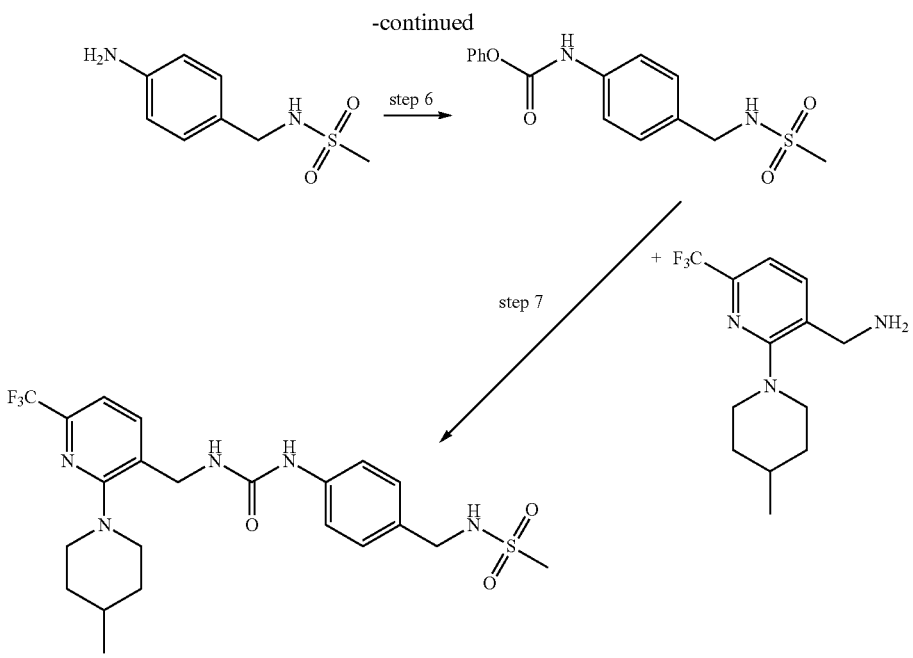

Step 1: To a stirred solution of (4-nitrophenyl)methanol (299 mg, 1.952 mmol) in dichloromethane were added triethylamine (0.3 mL, 2.147 mmol). Methanesulfonyl chloride (0.18 mL, 2.343 mmol) is added dropwise at 0° C. The reaction mixture was heated to 80° C. and stirred for 4 h, then cooled to room temperature and diluted with dichloromethane. The mixture was washed with water. The organic layer was dried over magnesium sulfate and filtered. The filtrate removed in vacuo. The crude was purified by column chromatography. 4-Nitrobenzyl methanesulfonate (333 mg, 74%) was obtained.

Step 2: To a stirred solution of 4-nitrobenzyl methanesulfonate (333 mg, 1.440 mmol) in dimethylformamide were added potassium phthalimide (293 mg, 1.584 mmol). The reaction mixture was stirred for 16 h. The mixture was dissolved in ethyl acetate, washed with water and brine. The organic layer was dried over magnesium sulfate and filtered. The filtrate removed in vacuo. The crude was purified by column chromatography. 2-(4-Nitrobenzyl)isoindoline-1,3-dione (535 mg) was obtained as crude.

Step 3: To a stirred solution of 2-(4-nitrobenzyl)isoindoline-1,3-dione (218 mg, 0.772 mmol) in tetrahydrofuran were added hydrazine monohydrate (246 mg, 3.089 mmol) and p-toluenesulfonic acid monohydrate (15 mg, 0.0772 mmol). The reaction mixture was stirred for 4 h at 80° C., then cooled to room temperature and diluted with ethyl acetate. The mixture was washed with water and brine. The organic layer was dried over magnesium sulfate and filtered. The filtrate removed in vacuo. The crude was purified by column chromatography. (4-Nitrophenyl)methanamine (46 mg, 39%) was obtained.

Step 4: To a stirred solution of (4-nitrophenyl)methanamine (46 mg, 0.302 mmol) in pyridine, cooled to 0° C., were added methanesulfonyl chloride (46 mg). The resulting reaction mixture was stirred for 1 h at room temperature. The mixture dissolved in dichloromethane and washed with 1N HCl. The organic layer was dried over magnesium sulfate and filtered. The filtrate removed in vacuo. The crude was purified by column chromatography. N-(4-Nitrobenzyl)methanesulfonamide (43 mg, 62%) was obtained.

Step 5: To a stirred solution of N-(4-nitrobenzyl)methanesulfonamide (43 mg, 0.188 mmol) in ethyl acetate were added 10% Pd/C (5 mg). The mixture was charged with hydrogen gas balloon. The resulting mixture was stirred for 3 h, then filtered using celite. The filtrate removed in vacuo. The crude was purified by column chromatography. N-(4-Aminobenzyl)methanesulfonamide (41 mg, 99%) was obtained.

Step 6: To a stirred solution of N-(4-aminobenzyl)methanesulfonamide (41 mg, 0.204 mmol) in tetrahydrofuran and acetonitrile as co-solvent were added phenylchloroformate (34 mg, 0.2142 mmol) and pyridine (0.02 mL, 0.2448 mmol). The reaction mixture was stirred for 3 h at room temperature. The mixture dissolved in ethyl acetate and washed with water and brine. The organic layer was dried over magnesium sulfate and filtered. The filtrate removed in vacuo. The crude was purified by column chromatography. Phenyl 4-(methylsulfonamidomethyl)phenylcarbamate (54 mg, 83%) was obtained.

Step 7: To a stirred solution of phenyl 4-(methylsulfonamidomethyl)phenylcarbamate (26 mg, 0.081 mmol) and (2-(4-methylpiperidin-1-yl)-6-(trifluoromethyl)pyridin-3-yl)methanamine (22 mg, 0.081 mmol) in acetonitrile were added 4-dimethylaminopyridine (10 mg, 0.081 mmol). The reaction mixture was stirred for 15 h at 50° C. The mixture dissolved in ethyl acetate and washed with water and brine. The organic layer was dried over magnesium sulfate and filtered. The filtrate removed in vacuo. The crude was purified by column chromatography. N-(4-(3-((2-(4-Methylpiperidin-1-yl)-6-(trifluoromethyl)pyridin-3-yl)methyl)ureido)benzyl)methanesulfonamide (example compound 5) (39 mg, 96%) was obtained.

$^1$H NMR (300 MHz, DMSO) δ 11.03 (s, 1H, NH), 8.77 (s, 1H, NH), 7.78 (d, 1H, J=7.86 Hz, Ar), 7.46 (d, 2H, J=4.77 Hz, Ar), 7.37 (d, 2H, J=8.61 Hz, Ar), 7.19 (d, 2H, J=8.61 Hz,

Ar), 6.74 (t, 1H, NH), 4.31 (d, 2H, J=5.31 Hz, CH2), 4.05 (d, 2H, J=6.24 Hz, CH2), 3.38 (m, 2H), 2.80 (s, 3H, Mesyl), 2.78 (m, 2H), 1.73 (d, 2H, J=12.18 Hz), 1.55 (br, 1H), 1.28 (m, 6H), 0.97 (d, 3H, J=6.42 Hz)

Synthesis of Example 6

—N-((2-(4-methylpiperidin-1-yl)-6-(trifluoromethyl)pyridin-3-yl)methyl)-2-(4-(methylsulfonamidomethyl)phenyl)propanamide

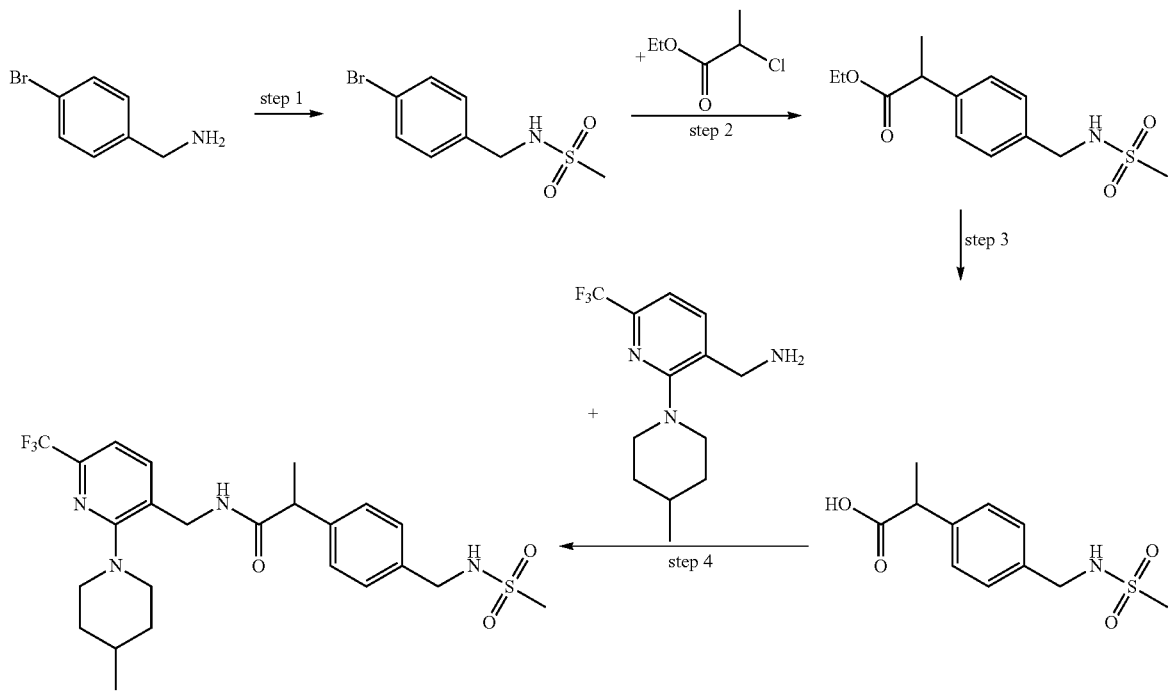

Step 1: (4-Bromophenyl)methanamine (500 mg, 2.687 mmol) was dissolved in pyridine (5 mL) and methanesulfonyl chloride (0.4 mL, 5.106 mmol) was added to the solution at 0° C. The mixture was stirred for 1 h at 0° C. Then, the mixture was quenched with 1N HCl solution and extracted with ethyl acetate. Drying over magnesium sulfate, evaporation of the ethyl acetate and purification by column chromatography (silica gel: 100-200 mesh, eluent: n-hexane/etyl acetate 1:1) gave N-(4-bromobenzyl)methanesulfonamide in pure form (663 mg, 93%).

Step 2: To a solution of N-(4-bromobenzyl)methanesulfonamide (663 mg, 2.51 mmol) in dimethylformamide, Manganese (276 mg, 5.02 mmol), NiBr$_2$(bipy) (66 mg, 0.176 mmol), ethyl 2-chloropropanoate (0.42 mL, 3.263 mmol) and trifluoroacetic acid (0.005 mL, 0.065 mmol) were added. The reaction mixture was stirred for 60 h at 65° C., quenched by concentrated HCl solution, extracted with diethyl ether, dried over magnesium sulfate and concentrated under reduced pressure. The resulting residue was purified by column chromatography (silica gel: 100-200 mesh, eluent: n-hexane/etyl acetate 1:1) to afford ethyl 2-(4-(methylsulfonamidomethyl)phenyl)propanoate (413 mg).

Step 3: To a solution of ethyl 2-(4-(methylsulfonamidomethyl)phenyl)propanoate (413 mg) in tetrahydrofuran—water mixture, sodium hydroxide (145 mg) was added at room temperature. The mixture was stirred for overnight, extracted with ethyl acetate, dried over magnesium sulfate. The solvent was evaporated by vacuo, the residue purified by column chromatography (silica gel: 100-200 mesh, eluent: methanol/dichloromethane 1:1) to obtain 2-(4-(methylsulfonamidomethyl)phenyl)propanoic acid (55 mg).

Step 4: 2-(4-(Methylsulfonamidomethyl)phenyl)propanoic acid (55 mg, 0.214 mmol) and (2-(4-methylpiperidin-1-yl)-6-(trifluoromethyl)pyridin-3-yl)methanamine (64 mg, 0.235 mmol) were dissolved in 1,4-dioxane. Followed by addition of 1-hydroxybenzotriazole (43 mg, 0.321 mmol), 1-ethyl-3-(3-dimethylaminopropyl) carbodiimide (62 mg, 0.321 mmol) and triethylamine (0.075 mL, 0.535 mmol) the reaction mixture was stirred for overnight and then quenched by water. After extraction with ethyl acetate, drying over magnesium sulfate and evaporation of the ethyl acetate the purification by column chromatography (silica gel: 100-200 mesh, eluent: methanol/dichloromethane 1:1) gave N-((2-(4-methylpiperidin-1-yl)-6-(trifluoromethyl)pyridin-3-yl)methyl)-2-(4-(methylsulfonamidomethyl)phenyl)propanamide (example 6) (94 mg, 78%) in pure form.

$^1$H—NMR (CDCl$_3$) δ 7.45 (d, 2H, Ar, J=7.50 Hz), 7.32 (m, 5H, Ar) 7.18 (d, 1H, Ar, J=7.68 Hz), 6.13 (m, 1H), 4.59 (m, 1H), 4.44 (d, 2H, J=5.85 Hz), 4.30 (d, 2H, J=6.21 Hz), 3.63 (q, 1H, J=7.14 Hz), 3.33 (m, 2H), 2.92 (s, 3H), 2.79 (m, 2H), 1.70 (m, 2H), 1.50 (m, 4H), 1.21 (m, 2H), 0.87 (d, 2H, J=7.35 Hz)

Synthesis of Example 8

—N-((2-(ethylamino)-6-(trifluoromethyl)pyridin-3-yl)methyl)-2-(3-fluoro-4-(methylsulfonamidomethyl)phenyl)propanamide

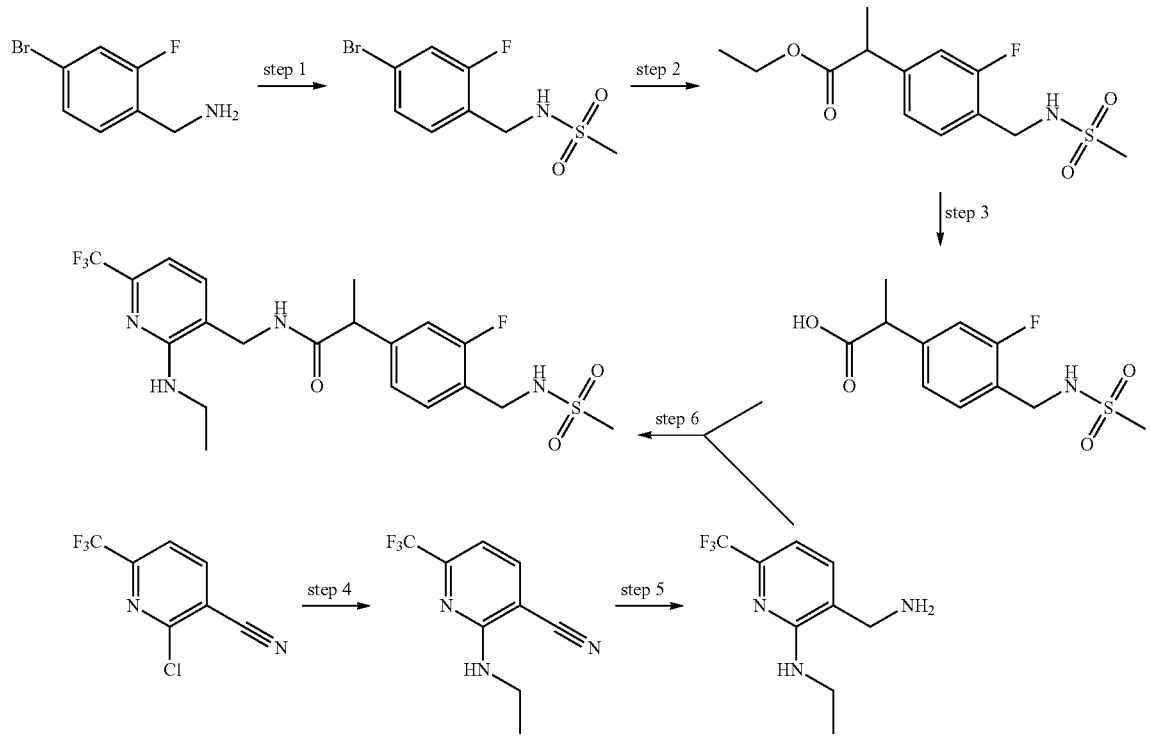

Step 1: To a stirred solution of (4-bromo-2-fluorophenyl)methanamine (2.5 g, 12.25 mmol) in pyridine (10 mL) at 0° C. in a protective gas atmosphere was added methanesulfonyl chloride (1.422 mL, 18.38 mmol) slowly in portions. After addition, the suspension was stirred at 0° C. for 1 h. The reaction mixture was diluted with ice cold water (20 mL) and pH was adjusted to ~1 using 16% aqueous HCl solution. The resulting precipitation was filtered off, washed with ethyl acetate (3×20 mL) and dried overnight. The crude N-(4-bromo-2-fluorobenzyl)-methanesulfonamide (3.14 g, 91%) was used as such without further purification.

Step 2: N-(4-bromo-2-fluorobenzyl)methanesulfonamide (2 g, 7.09 mmol) and ethyl-2-chloropropionate (1.174 mL, 9.21 mmol) were dissolved in dimethylformamide (11 mL) in a protective gas atmosphere at room temperature. Subsequently, manganese (779 mg, 14.178 mmol), (2,2'-bipyridine)nickel(II) dibromide (186 mg, 0.496 mmol) and trifluoroacetic acid (0.014 mL) were added and the mixture was stirred at 65° C. for 36 h. The reaction mixture was cooled to room temperature, hydrolysed using 1N HCl (25 mL) and extracted with diethyl ether (4×25 mL). The combined organic layer were washed with water (25 mL) and brine (25 mL) and dried over magnesium sulfate. The solvent was evaporated under reduced pressure and the obtained residue was purified by column chromatography (silica gel: 100-200 mesh, eluent: diethyl ether/n-hexane 10:1) to afford ethyl 2-(3-fluoro-4-(methylsulfonamidomethyl)phenyl)propanoate (342 mg, 16%).

Step 3: The ethyl 2-(3-fluoro-4-(methylsulfonamidomethyl)phenyl)propanoate (100 mg, 0.329 mmol) was dissolved in tetrahydrofuran-water mixture (1.4 mL, 2:1), lithium hydroxide (2 mg, 0.987 mmol) was added and refluxing carried out for 16 h. After evaporation of the organic solvent under reduced pressure, the reaction mixture was extracted with diethyl ether (1×15 mL). The aqueous layer was acidified using 1N HCl to pH=2 and extracted with dichloromethane (3×15 mL). The combined organic layer was dried over magnesium sulfate and concentrated under reduced pressure to afford 2-(3-fluoro-4-(methylsulfonamidomethyl)phenyl)propanoic acid (72 mg, 80%).

Step 4: To a stirred solution of 2-chloro-6-(trifluoromethyl)nicotinonitrile (1 g, 4.85 mmol) in tetrahydrofuran (10 mL) was added ethanamine (0.78 g, 12.12 mmol) and stirred for 12 h at room temperature. The reaction mixture was diluted with 1N HCl (10 mL) and extracted with ethyl acetate (2×25 mL). The combined organic layer was washed with 1N HCl (15 mL) and brine, dried over magnesium sulfate and concentrated under reduced pressure to afford 2-(ethylamino)-6-(trifluoromethyl)nicotinonitrile (1.01 g, 97%).

Step 5: 2-(Ethylamino)-6-(trifluoromethyl)nicotinonitrile (1 g, 4.647 mmol) was dissolved in 2M methanolic ammonia solution (182 mL, 0.025 mmol/mL) and hydrogenated in a H-cube apparatus (flow rate 1 mL/min, 80° C., 10 bar). The solvent was evaporated under reduced pressure to afford 3-(aminomethyl)-N-ethyl-6-(trifluoromethyl)pyridin-2-amine (948 mg, 93%) as pure compound.

Step 6: To a stirred solution of 3-(aminomethyl)-N-ethyl-6-(trifluoromethyl)pyridin-2-amine (57 mg, 0.263 mmol) and 2-(3-fluoro-4-(methylsulfonamidomethyl)phenyl) propanoic acid (72 mg, 0.263 mmol) in tetrahydrofuran (2 mL) were added 1-hydroxybenzotriazol (0.036 mL, 0.263 mmol), O-(1H-benzotriazol-1-yl)-N,N,N',N'-tetramethyluronium tetrafluoroborate (85 mg, 0.263 mmol) and N-ethyldiisopropylamine (0.134 mL, 0.789 mmol). The reaction mixture was stirred for 42 h at room temperature. The reaction mixture was concentrated under reduced pressure and the solid obtained was purified by column chromatography (silica gel: 100-200 mesh, eluent: ethyl acetate/cyclohexane 3:2) to afford N-((2-(ethylamino)-6-(trifluoromethyl)pyridin-3-yl)methyl)-2-(3-fluoro-4-(methylsulfonamido-methyl)phenyl)propanamide (example 8) (69 mg, 55%).

The following example compounds were synthesized or may be synthesized in the same manner: examples 7, 9-14, 17-23 and 30-43.

Step 1: To a stirred solution of 2-fluoro-1-methyl-4-nitrobenzene (1.993 g, 12.85 mmol) in carbon tetrachloride were added benzoyl peroxide (497 mg, 1.2847 mmol) and N-bromosuccinimide (2.972 g, 16.701 mmol). The reaction mixture was refluxed for 18 h, then cooled to room temperature. The mixture was dissolved in ethyl acetate, then washed with water and brine. The organic layer was dried over magnesium sulfate and filtered. The filtrate removed in vacuo. The crude was purified by column chromatography to gave 1-(bromomethyl)-2-fluoro-4-nitrobenzene (780 mg, 26%).

Step 2: To a stirred solution of 1-(bromomethyl)-2-fluoro-4-nitrobenzene (780 mg, 3.3 mmol) in dimethylformamide were added potassium phthalimide (1.235 g, 6.67 mmol). The reaction mixture was stirred for 18 h at room temperature. The mixture was dissolved in ethyl acetate, washed with water and brine. The organic layer was dried over magnesium sulfate and filtered. The filtrate removed in vacuo. The crude was purified by column chromatography. 2-(2-Fluoro-4-nitrobenzyl)isoindoline-1,3-dione (1.034 g) was obtained as crude.

Synthesis of Example 24

—N-(2-fluoro-4-(3-((2-(4-methylpiperidin-1-yl)-6-(trifluoromethyl)pyridin-3-yl)methyl)ureido)benzyl)methanesulfonamide

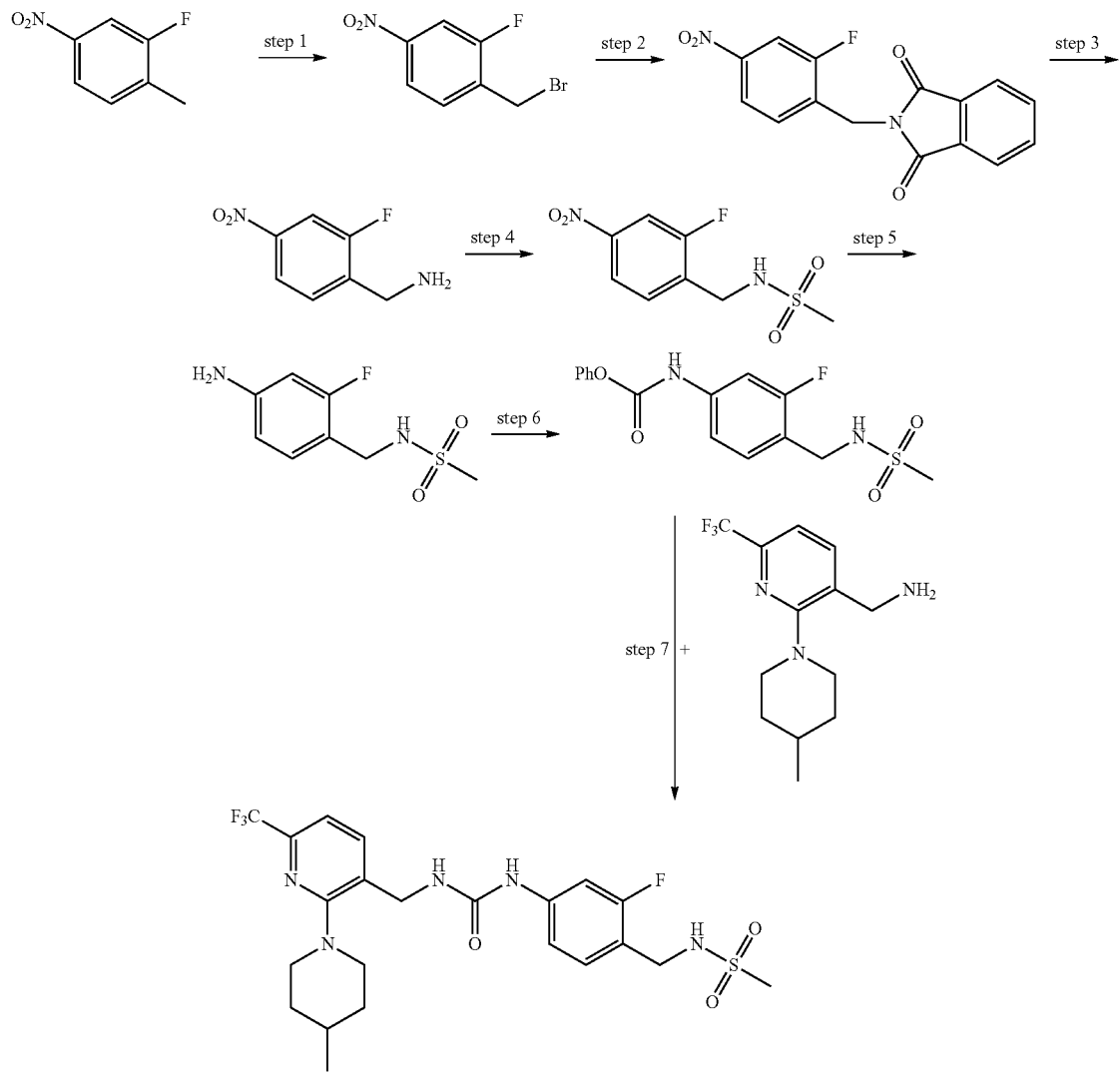

Step 3: To a stirred solution of 2-(2-fluoro-4-nitrobenzyl) isoindoline-1,3-dione (1.034 g, 3.44 mmol) in tetrahydrofuran were added hydrazine monohydrate (1.104 g, 13.77 mmol) and p-toluenesulfonic acid monohydrate (66 mg, 0.34 mmol). The reaction mixture was refluxed for 6 h, then cooled to room temperature and diluted ethyl acetate. The mixture was washed with water and brine. The organic layer was dried over magnesium sulfate and the solvent removed under reduced pressure. The crude was purified by column chromatography to afford (2-fluoro-4-nitrophenyl)methanamine (329 mg, 56%).

Step 4: To a stirred solution of (2-fluoro-4-nitrophenyl) methanamine (131 mg, 0.77 mmol) in pyridine, cooled to 0° C., were added methanesulfonyl chloride (131 mg). The resulting reaction mixture was stirred for 1 h at room temperature. The mixture dissolved in dichloromethane and washed with 1N HCl solution. The organic layer was dried over magnesium sulfate and the filtrate removed in vacuo. The crude was purified by column chromatography to afford N-(2-fluoro-4-nitrobenzyl)methanesulfonamide (173 mg, 91%).

Step 5: To a stirred solution of N-(2-fluoro-4-nitrobenzyl) methanesulfonamide (187 mg, 0.75 mmol) in tetrahydrofuran and ethanol as co-solvent were added 10% Pd/C (20 mg). The mixture was charged with hydrogen gas balloon. The resulting mixture was stirred for 15 h, then filtered using celite. The filtrate removed in vacuo. The crude was purified by column chromatography. N-(4-amino-2-fluorobenzyl)methanesulfonamide (135 mg, 82%) was obtained.

Step 6: To a stirred solution of N-(4-amino-2-fluorobenzyl) methanesulfonamide (135 mg, 0.618 mmol) in tetrahydrofuran and acetonitrile as co-solvent were added phenylchloroformate (0.08 mL, 0.6489 mmol) and pyridine (0.06 mL, 0.7416 mmol). The reaction mixture was stirred for 1 h at room temperature. The mixture dissolved in ethyl acetate and washed with water and brine. The organic layer was dried over magnesium sulfate and filtered. The filtrate removed in vacuo. The crude was purified by column chromatography. Phenyl 3-fluoro-4-(methylsulfonamidomethyl)phenylcarbamate (140 mg, 67%) was obtained.

Step 7: To a stirred solution of phenyl 3-fluoro-4-(methylsulfonamidomethyl)phenyl-carbamate (46 mg, 0.136 mmol) and (2-(4-methylpiperidin-1-yl)-6-(trifluoromethyl)pyridin-3-yl)methanamine (37 mg, 0.136 mmol) in acetonitrile were added 4-dimethylaminopyridine (17 mg, 0.136 mmol). The reaction mixture was stirred for 15 h at 50° C. The mixture dissolved in ethyl acetate and washed with water and brine. The organic layer was dried over magnesium sulfate and filtered. The filtrate removed in vacuo. The crude was purified by column chromatography. N-(2-Fluoro-4-(3-((2-(4-methylpiperidin-1-yl)-6-(trifluoromethyl)pyridin-3-yl)methyl)ureido)benzyl)methanesulfonamide (example 24) (65 mg, 92%) was obtained.

$^1$H NMR (300 MHz, DMSO) δ 9.01 (s, 1H, NH), 7.78 (d, 1H, J=7.71 Hz, Ar), 7.46 (m, 3H, Ar), 7.27 (t, 1H, J=8.49 Hz, Ar), 7.05 (dd, 1H, J=8.22, 1.83 Hz, Ar), 6.83 (t, 1H, NH), 4.32 (d, 2H, J=5.67 Hz, CH$_2$), 4.09 (d, 2H, 6.03 Hz, CH$_2$), 3.38 (m, 2H), 2.85 (s, 3H, Mesyl), 2.78 (t, 2H), 1.73 (d, 2H, J=11.16 Hz), 1.55 (br, 1H), 1.31 (t, 1H), 0.97 (d, 3H, J=6.6 Hz).

Exemplary compound 44 can be and exemplary compound 47 was prepared in a similar manner.

Synthesis of Example 45

-2-(3-chloro-4-(methylsulfonamidomethyl)phenyl)-N-((2-(pyrrolidin-1-yl)-6-(trifluoromethyl)pyridin-3-yl)methyl)propanamide

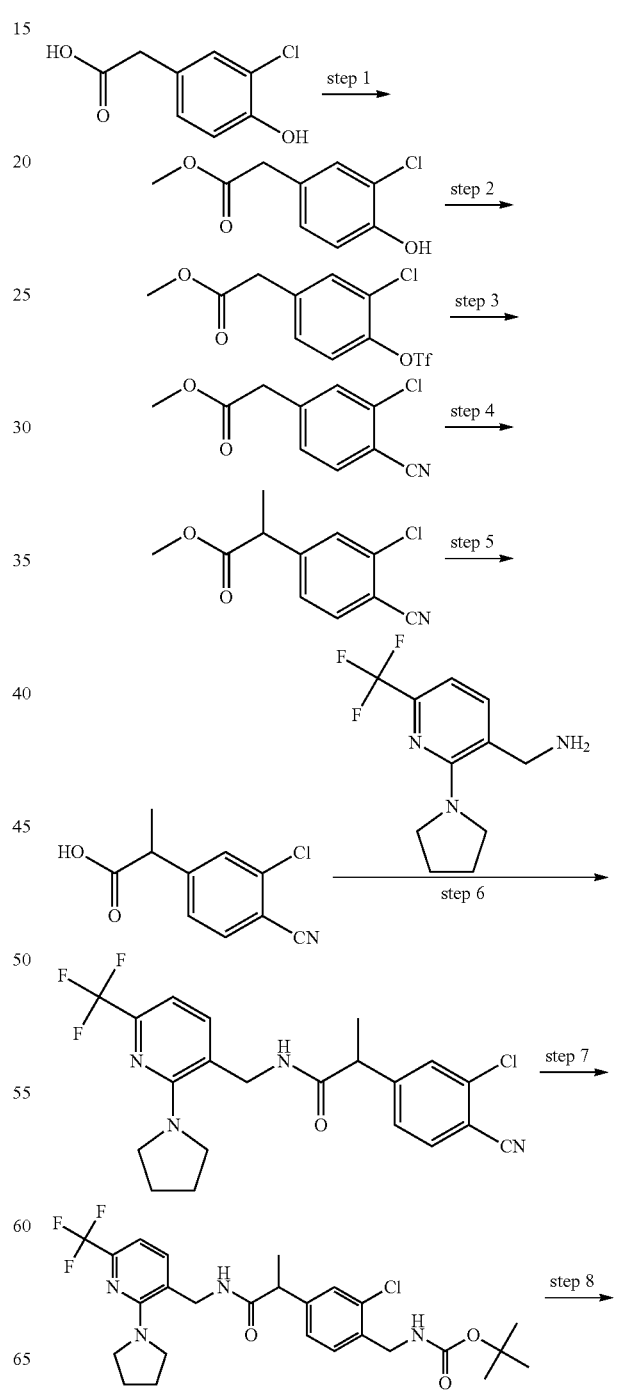

-continued

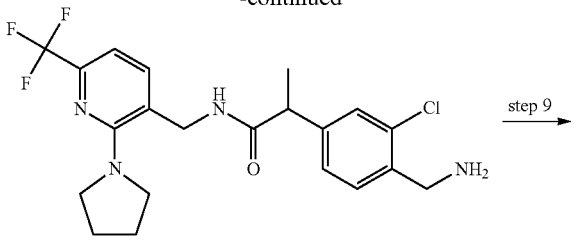

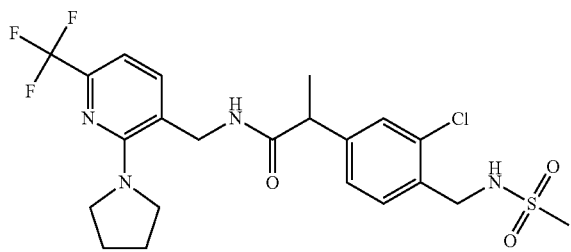 [SMILES: CC(C(=O)NCc1ccc(C(F)(F)F)nc1N1CCCC1)c1ccc(CNS(C)(=O)=O)c(Cl)c1]

Step 1: To a stirred solution of 2-(3-chloro-4-hydroxyphenyl) acetic acid (3 g, 16.078 mmol) in methanol (35 mL) were added sulfuric acid (0.3 mL). The reaction mixture was refluxed for 15 h and cooled to room temperature. The solvent was evaporated. The residue dissolved in ethyl acetate and extracted with NaHCO$_3$. The organic layer was dried over magnesium sulfate and filtered. The filtrate removed in vacuo. The crude was purified by column chromatography. Methyl 2-(3-chloro-4-hydroxyphenyl)acetate (3.557 g) was obtained as 99% yield.

Step 2: To a stirred solution of methyl 2-(3-chloro-4-hydroxyphenyl)acetate (3.557 g, 17.73 mmol) and trimethylamine (2.5 mL, 17.73 mmol) in dichloromethane. Triflic anhydride (3 mL, 17.73 mmol) is added dropwise at 0° C. The reaction mixture was stirred for 2 h. The residue extracted in dichloromethane and washed with water and brine. The organic layer was dried over magnesium sulfate and filtered. The filtrate removed in vacuo. The crude was purified by column chromatography to give methyl 2-(3-chloro-4-(trifluoromethylsulfonyloxy)-phenyl)acetate (5.15 g, 87%).

Step 3: To a stirred solution of methyl 2-(3-chloro-4-(trifluoromethylsulfonyloxy)-phenyl)acetate (4.419 g, 13.283 mmol) in dimethylformamide were added zinc cyanide (1.6 g, 13.681 mmol) and tetrakis(triphenylphosphine) palladium (1.5 g, 1.3283 mmol). The reaction mixture was stirred for 34 h at 80° C., then cooled to room temperature and diluted with ethyl acetate. The mixture was filtered using celite pad. The filtrate dissolved in ethyl acetate and extracted with NaHCO$_3$. The organic layer was dried over magnesium sulfate and filtered. The filtrate removed in vacuo. The crude was purified by column chromatography to give methyl 2-(3-chloro-4-cyanophenyl)acetate (1.044 g, 37%).

Step 4: To a stirred solution of methyl 2-(3-chloro-4-cyanophenyl)acetate (931 mg, 4.441 mmol) in dimethylformamide were added 60% sodium hydride (178 mg, 4.441 mmol) and iodomethane (0.3 mL, 4.441 mmol) at 0° C. The reaction mixture was stirred for 1 h at 0° C., then diluted with water. The residue dissolved in ethyl acetate and washed with water and brine. The organic layer was dried over magnesium sulfate and filtered. The filtrate removed in vacuo. The crude was purified by column chromatography to give methyl 2-(3-chloro-4-cyanophenyl)propanoate (642 mg, 65%).

Step 5: To a stirred solution of methyl 2-(3-chloro-4-cyanophenyl)propanoate (642 mg, 2.87 mmol) in co-solvent with tetrahydrofuran and water (1:1) were added sodium hydroxide (287 mg, 7.175 mmol). The reaction mixture was stirred for 15 h at room temperature, then acidified to pH 3~4 with acetic acid. The residue dissolved in ethyl acetate and washed with water and brine. The organic layer was dried over magnesium sulfate and filtered. The filtrate removed in vacuo. The crude was purified by column chromatography. 2-(3-Chloro-4-cyanophenyl)propanoic acid (665 mg) was obtained as 99% yield.

Step 6: To a stirred solution of 2-(3-Chloro-4-cyanophenyl) propanoic acid (100 mg, 0.477 mmol) and (2-(pyrrolidin-1-yl)-6-(trifluoromethyl)pyridin-3-yl)methanamine (117 mg, 0.477 mmol) in acetonitrile were added N-(3-dimethylaminopropyl)-N'-ethylcarbodiimide (137 mg, 0.7155 mmol), 1-hydroxybenzotriazole (97 mg, 0.7155 mmol) and triethylamine (0.17 mL, 1.1925 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. 2-(3-Chloro-4-cyanophenyl)-N-((2-(pyrrolidin-1-yl)-6-(trifluoromethyl)pyridin-3-yl)methyl)propanamide (158 mg) was obtained as 76% yield.

Step 7: To a stirred solution of 2-(3-chloro-4-cyanophenyl)-N-((2-(pyrrolidin-1-yl)-6-(trifluoromethyl)pyridin-3-yl) methyl)propanamide (158 mg, 0.361 mmol) in methanol, cooled to 0° C., were added di-tert-butyl dicarbonate (158 mg, 0.722 mmol) and nickel(II) chloride hexahydride (9 mg, 0.0361 mmol). Sodium borohydride (96 mg, 2.527 mmol) was added in small portions. The resulting reaction mixture was allowed to warm to room temperature and left to stir for 1 h. Diethylenetriamine (0.04 mL, 0.361 mmol) was added to the mixture. The mixture was stirred for 1 h. The solvent was evaporated. The residue dissolved in ethyl acetate and extracted with NaHCO$_3$ solution. The organic layer was dried over magnesium sulfate and filtered. The filtrate removed in vacuo. The crude was purified by column chromatography. Tert-butyl 2-chloro-4-(1-oxo-1-((2-(pyrrolidin-1-yl)-6-(trifluoromethyl)pyridin-3-yl)methylamino)propan-2-yl)benzylcarbamate (123 mg) was obtained as 47% yield.

Step 8: To a stirred solution of tert-butyl 2-chloro-4-(1-oxo-1-((2-(pyrrolidin-1-yl)-6-(trifluoromethyl)pyridin-3-yl) methylamino)propan-2-yl)benzylcarbamate (123 mg, 0.227 mmol) in dichloromethane (4 mL), cooled to 0° C., was added trifluoroacetic acid (2 mL). The resulting reaction mixture was stirred for 1 h at 0° C. and 1 h at room temperature, then basified to pH 8~9 with aqueous NaHCO$_3$. The mixture was filtered using celite pad. The filtrate dissolved in dichloromethane and extracted with NaHCO$_3$. The organic layer was dried over magnesium sulfate and filtered. The filtrate removed in vacuo. The crude was purified by column chromatography. 2-(4-(Ainomethyl)-3-chlorophenyl)-N-((2-(pyrrolidin-1-yl)-6-(trifluoromethyl)pyridin-3-yl)methyl)propanamide (81 mg) was obtained in 81% yield.

Step 9: To a stirred solution of 2-(4-(aminomethyl)-3-chlorophenyl)-N-((2-(pyrrolidin-1-yl)-6-(trifluoromethyl)pyridin-3-yl)methyl)propanamide (81 mg, 0.183 mmol) in pyridine, cooled to 0° C., was added methanesulfonyl chloride (81 mg). The resulting reaction mixture was stirred for 15 h at room temperature. The mixture dissolved in dichloromethane and washed with 1N HCl. The organic layer was dried over magnesium sulfate and filtered. The filtrate removed in vacuo. The crude was purified by column chromatography. 2-(3-Chloro-4-(methylsulfonamidomethyl)phenyl)-N-((2-(pyrrolidin-1-yl)-6-(trifluoromethyl)pyridin-3-yl)methyl)propanamide (example 45) (65 mg) was obtained in 68% yield.

$^1$H NMR (300 MHz, CDCl$_3$) 7.38 (m, 3H, Ar), 7.20 (d, 1H, J=7.86 Hz, Ar), 6.93 (d, 1H, J=7.53 Hz, Ar), 5.72 (br, 1H, NH), 4.84 (br, 1H, NH), 4.45 (d, 2H, CH$_2$), 4.38 (d, 2H, CH2), 3.52 (q, 1H, CH), 3.43 (4H, pyrrole), 2.88 (s, 3H, mesyl), 1.85 (quintet, 4H, pyrrole), 1.50 (d, 3H, methyl)

Exemplary compounds 16, 56 and 62 were prepared or can be prepared in a similar manner.

Synthesis of Example 46

-2-(3-chloro-4-(methylsulfonamidomethyl)phenyl)-N-((2-(4-methylpiperidin-1-yl)-6-(trifluoromethyl)pyridin-3-yl)methyl)propanamide

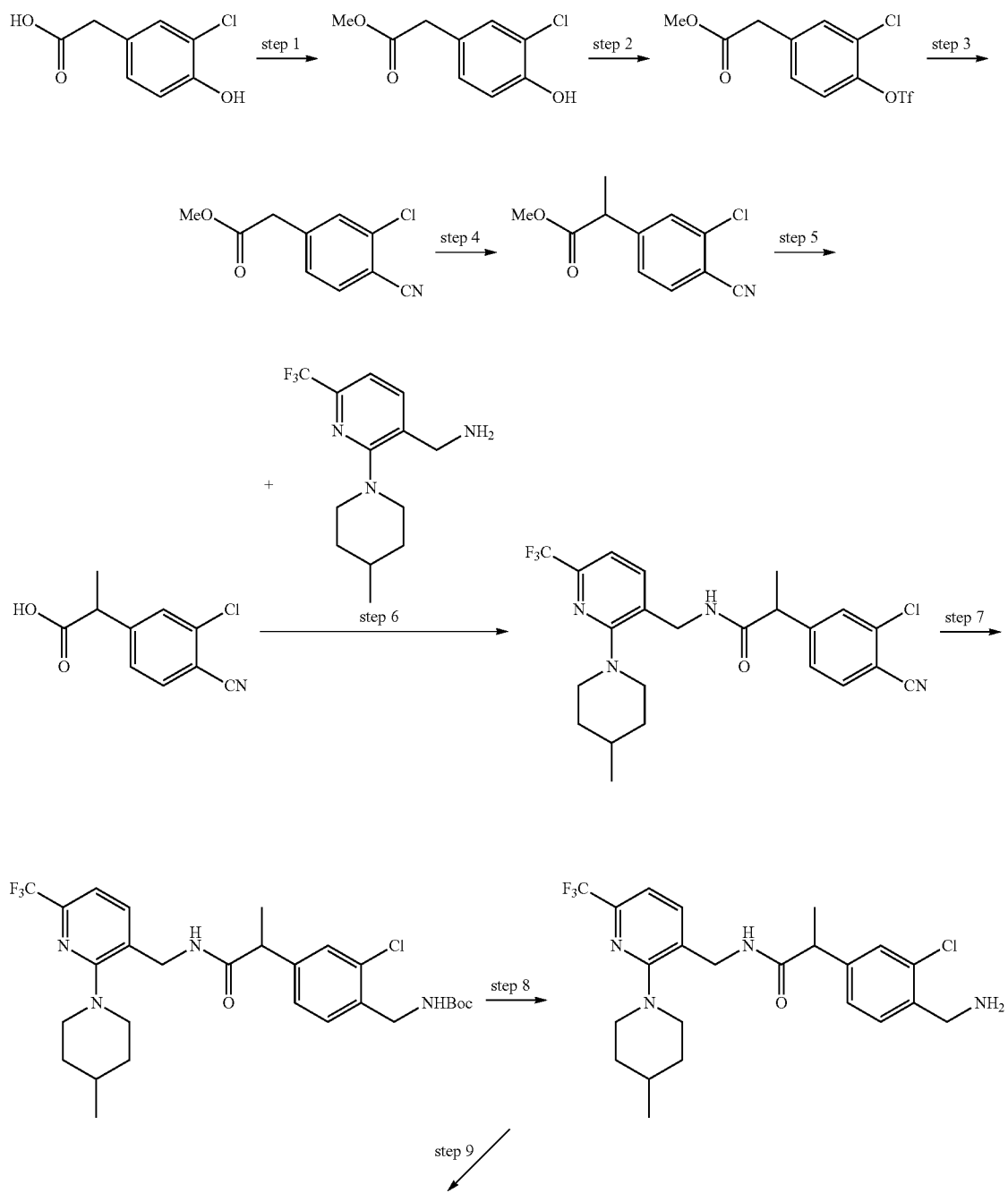

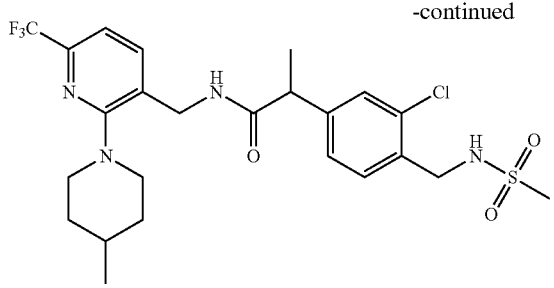

-continued

Step 1-5: according to example 45.

Step 6: To a stirred solution of 2-(3-chloro-4-cyanophenyl) propanoic acid (224 mg, 1.069 mmol) and (2-(4-methylpiperidin-1-yl)-6-(trifluoromethyl)pyridin-3-yl)methanamine (321 mg, 1.175 mmol) in acetonitrile were added 1-ethyl-3-(3-dimethylaminopropyl) carbodiimide (307 mg, 1.064 mmol), 1-hydroxybenzotriazole (217 mg, 1.064 mmol) and triethylamine (0.4 ml, 2.673 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. 2-(3-chloro-4-cyanophenyl)-N-((2-(4-methylpiperidin-1-yl)-6-(trifluoromethyl)pyridin-3-yl)methyl)propanamide (679 mg, 99%) was obtained.

Step 7: To a stirred solution of 2-(3-chloro-4-cyanophenyl)-N-((2-(4-methylpiperidin-1-yl)-6-(trifluoromethyl)pyridin-3-yl)methyl)propanamide (679 mg, 1.460 mmol) in methanol, cooled to 0° C., were added di-tert-butyl dicarbonate (638 mg, 2.921 mmol) and NiCl$_2$.6H$_2$O (35 mg, 0.147 mmol). Sodium borohydride (387 mg, 10.22 mmol) was then added in small portions. The reaction was exothermic and effervescent. The resulting reaction mixture was allowed to warm to room temperature and left to stir for 1 h. Diethylenetriamine (0.16 mL, 1.460 mmol) was added to the mixture. The mixture was stirred for 1 h. The solvent was evaporated. The residue dissolved in ethyl acetate and extracted with aqueous sodium hydrogen carbonate. The organic layer was dried over magnesium sulfate and filtered. The filtrate removed in vacuo. The crude was purified by column chromatography. tert-butyl 2-chloro-4-(1-((2-(4-methylpiperidin-1-yl)-6-(trifluoromethyl)pyridin-3-yl)methylamino)-1-oxopropan-2-yl)benzylcarbamate (390 mg, 47%) was obtained.

Step 8: To a stirred solution of tert-butyl 2-chloro-4-(1-((2-(4-methylpiperidin-1-yl)-6-(trifluoromethyl)pyridin-3-yl) methylamino)-1-oxopropan-2-yl)benzylcarbamate (390 mg, 0.685 mmol) in dichloromethane (4 mL), cooled to 0° C. were added trifluoroacetic acid (2 mL). The resulting reaction mixture was stirred for 1 h at 0° C. and 1 h at room temperature, then basified to pH 8~9 with aqueous sodium hydrogen carbonate. The mixture was filtered using celite pad. The filtrate dissolved in dichloromethane and extracted with aqueous sodium hydrogen carbonate. The organic layer was dried over magnesium sulfate and filtered. The filtrate removed in vacuo. The crude was purified by column chromatography. 2-(4-(Aminomethyl)-3-chlorophenyl)-N-((2-(4-methylpiperidin-1-yl)-6-(trifluoromethyl)pyridin-3-yl)methyl)propanamide (242 mg, 75%) was obtained.

Step 9: To a stirred solution of 2-(4-(aminomethyl)-3-chlorophenyl)-N-((2-(4-methylpiperidin-1-yl)-6-(trifluoromethyl)pyridin-3-yl)methyl)propanamide (242 mg, 0.516 mmol) in pyridine, cooled to 0° C., were added methanesulfonyl chloride (242 mg). The resulting reaction mixture was stirred for 15 h at room temperature. The mixture dissolved in dichloromethane and washed with 1N HCl. The organic layer was dried over magnesium sulfate and filtered. The filtrate removed in vacuo. The crude was purified by column chromatography. 2-(3-Chloro-4-(methylsulfonamidomethyl)phenyl)-N-((2-(4-methylpiperidin-1-yl)-6-(trifluoromethyl)pyridin-3-yl)methyl)propanamide (example 46) (211 mg, 75%) was obtained.

$^1$H NMR (300 MHz, CDCl$_3$) δ 7.43 (m, 2H, Ar), 7.35 (s, 1H, Ar), 7.19 (m, 2H, Ar), 6.38 (br, 1H, NH), 5.01 (br, 1H, NH), 4.45 (d, 2H, J=5.7 Hz, CH$_2$), 4.37 (d, 2H, J=6.39 Hz, CH2), 3.56 (q, 1H, J=7.14 Hz), 3.30 (t, 2H, J=14.01 Hz), 2.87 (s, 3H, Mesyl), 2.81 (t, 2H, J=12.27 Hz), 1.72 (br, 2H), 1.5 (d, 3H, J=7.14 Hz), 1.55 (br, 1H), 1.25 (m, 2H), 0.95 (d, 3H, J=6.6 Hz).

Exemplary compounds 25-29 and 58 were prepared or can be prepared in a similar manner.

Synthesis of Example 48

-2-(3-methoxy-4-(methylsulfonamidomethyl)phenyl)-N-((2-(pyrrolidin-1-yl)-6-(trifluoromethyl)pyridin-3-yl)methyl)propanamide

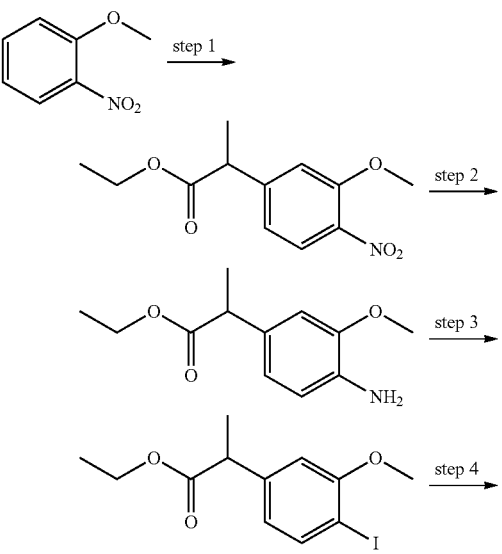

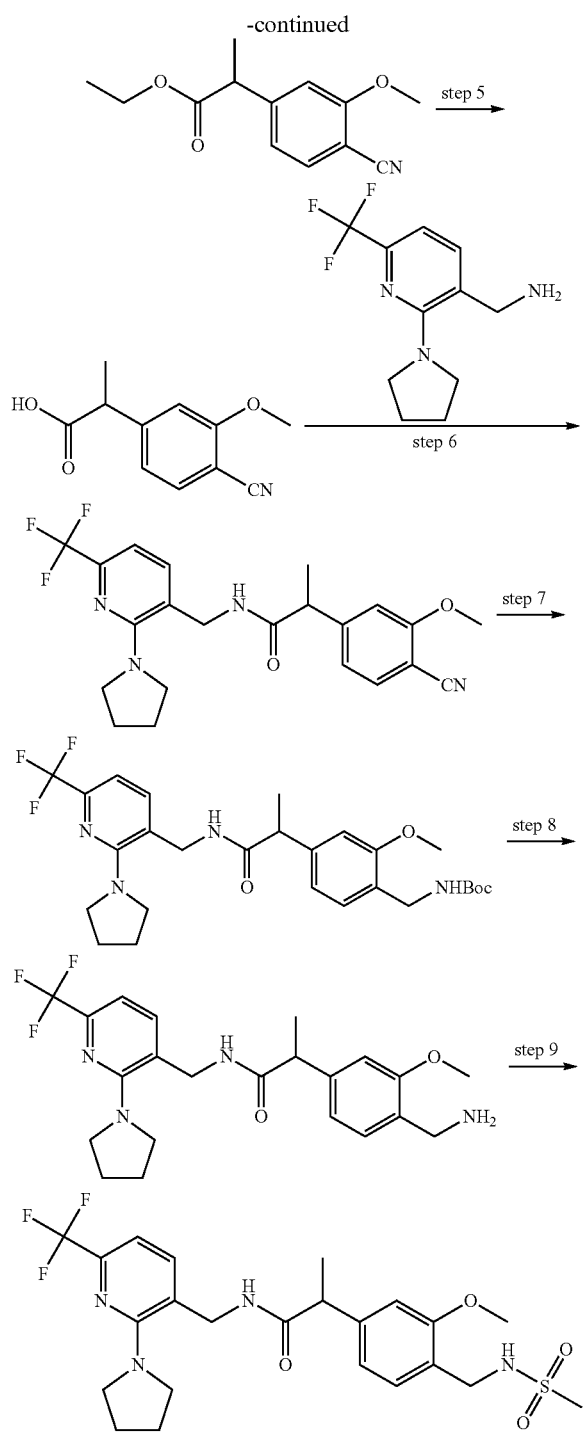

fied by column chromatography. Ethyl 2-(3-methoxy-4-nitrophenyl)propanoate (683 mg) was obtained as 14% yield.

Step 2: To a stirred solution of ethyl 2-(3-methoxy-4-nitrophenyl)propanoate (683 mg, 2.697 mmol) in tetrahydrofuran and ethanol as co-solvent were added 10% palladium on carbon (70 mg). The mixture was charged with $H_2$ (gas) balloon. The resulting mixture was stirred for 15 h, then filtered using celite. The filtrate removed in vacuo. The crude was purified by column chromatography. Ethyl 2-(4-amino-3-methoxyphenyl)propanoate (447 mg) was obtained as 74% yield.

Step 3: To a stirred solution of ethyl 2-(4-amino-3-methoxyphenyl)propanoate (447 mg, 2.002 mmol) in acetonitrile and water were added p-TsOH.$H_2$O (1.142 g, 6.006 mmol), sodium nitrite (276 mg, 4.004 mmol) and potassium iodide (831 mg, 5.005 mmol). The reaction mixture was stirred for 4 h at room temperature. The mixture dissolved in ethyl acetate and washed with water and brine. The organic layer was dried over magnesium sulfate and filtered. The filtrate removed in vacuo. The crude was purified by column chromatography. Ethyl 2-(4-iodo-3-methoxyphenyl)propanoate (468 mg) was obtained as 70% yield.

Step 4: To a stirred solution of ethyl 2-(4-iodo-3-methoxyphenyl)propanoate (626 mg, 1.873 mmol) in dimethylformamide were added zinc cyanide (227 mg, 1.929 mmol) and tetrakis(triphenylphosphine) palladium (216 mg, 0.1873 mmol). The reaction mixture was stirred for 36 h at 120° C., then cooled to room temperature, diluted with ethylacetate. The mixture was filtered using celite pad. The filtrate dissolved in ethyl acetate and extracted with $NaHCO_3$. The organic layer was dried over magnesium sulfate and filtered. The filtrate removed in vacuo. The crude was purified by column chromatography. Ethyl 2-(4-cyano-3-methoxyphenyl)propanoate (222 mg) was obtained as 51% yield.

Step 5: To a stirred solution of ethyl 2-(4-cyano-3-methoxyphenyl)propanoate (222 mg, 0.952 mmol) in co-solvent with tetrahydrofuran and water (1:1) were added sodium hydroxide (95 mg, 2.38 mmol). The reaction mixture was stirred for 15 h at room temperature, then acidified to pH 3~4 with acetic acid. The residue dissolved in ethyl acetate and washed with water and brine. The organic layer was dried over magnesium sulfate and filtered. The filtrate removed in vacuo. The crude was purified by column chromatography. 2-(4-Cyano-3-methoxyphenyl)propanoic acid (188 mg) was obtained as 96% yield.

Step 6: To a stirred solution of 2-(4-cyano-3-methoxyphenyl)propanoic acid (0.458 mmol) and (2-(pyrrolidin-1-yl)-6-(trifluoromethyl)pyridin-3-yl)methanamine (0.5038 mmol) in acetonitrile were added N-(3-dimethylaminopropyl)-N'-ethylcarbodiimide (0.687 mmol), 1-hydroxybenzotriazole (0.687 mmol) and triethylamine (1.145 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. 2-(4-Cyano-3-methoxyphenyl)-N-((2-(pyrrolidin-1-yl)-6-(trifluoromethyl)pyridin-3-yl)methyl)propanamide was obtained as 99% yield.

Step 7: To a stirred solution of 2-(4-cyano-3-methoxyphenyl)-N-((2-(pyrrolidin-1-yl)-6-(trifluoromethyl)pyridin-3-yl)methyl)propanamide (0.473 mmol) in methanol, cooled to 0° C., were added di-tert-butyl dicarbonate (0.946 mmol) and $NiCl_2$.6 $H_2$O (0.0473 mmol). Nsodium Step 1: To a stirred solution of 1-methoxy-2-nitrobenzene (3 g, 19.590 mmol) in dimethylformamide were added potassium tert-butoxide (8.792 g, 78.36 mmol) and ethyl 2-chloropropionate (2.5 mL, 19.59 mmol) while maintaining below −30° C. The reaction mixture was stirred for 5 min at −30° C., then ethyl 2-chloropropionate (0.25 mL, 1.959 mmol) was added to mixture. The reaction mixture was stirred for 10 min at room temperature. The residue was dissolved in ethyl acetate and washed with water and brine. The organic layer was dried over magnesium sulfate and filtered. The filtrate removed in vacuo. The crude was puriborohydride (3.311 mmol) was then added in small portions. The reaction was exothermic and effervescent. The resulting reaction mixture was allowed to warm to room temperature and left to stir for 1 h. Diethylenetriamine (0.473 mmol) was added to the mixture. The mixture was stirred for 1 h. The solvent was evaporated. The residue dissolved in ethyl acetate and extracted with NaHCO₃. The organic layer was dried over magnesium sulfate and filtered. The filtrate removed in vacuo. The crude was purified by column chromatography. Tert-butyl 2-methoxy-4-(1-oxo-1-((2-(pyrrolidin-1-yl)-6-(trifluoromethyl)pyridin-3-yl)methylamino)propan-2-yl)benzylcarbamate was obtained as 58% yield.

Step 8: To a stirred solution of tert-butyl 2-methoxy-4-(1-oxo-1-((2-(pyrrolidin-1-yl)-6-(trifluoromethyl)pyridin-3-yl)methylamino)propan-2-yl)benzylcarbamate (0.274 mmol) in dichloromethane (4 mL), cooled to 0° C., were added trifluoroacetic acid (1 mL). The resulting reaction mixture was stirred for 2 h at 0° C. and 2 h at room temperature, then basified to pH 8~9 with aq. NaHCO₃. The mixture was filtered using celite pad. The filtrate dissolved in dichloromethane and extracted with NaHCO₃. The organic layer was dried over magnesium sulfate and filtered. The filtrate removed in vacuo. The crude was purified by column chromatography. 2-(4-(Aminomethyl)-3-methoxyphenyl)-N-((2-(pyrrolidin-1-yl)-6-(trifluoromethyl)pyridin-3-yl)methyl)propanamide was obtained as 51% yield.

Step 9: To a stirred solution of 2-(4-(aminomethyl)-3-methoxyphenyl)-N-((2-(pyrrolidin-1-yl)-6-(trifluoromethyl)pyridin-3-yl)methyl)propanamide (147 mg, 0.337 mmol) in pyridine, cooled to 0° C., were added methanesulfonyl chloride (0.03 mL). The resulting reaction mixture was stirred for 20 min at room temperature. The mixture dissolved in dichloromethane and washed with 1N HCl. The organic layer was dried over magnesium sulfate and filtered. The filtrate removed in vacuo. The crude was purified by column chromatography. 2-(3-Methoxy-4-(methylsulfonamidomethyl)phenyl)-N-((2-(pyrrolidin-1-yl)-6-(trifluoromethyl)pyridin-3-yl)methyl)propanamide (example 48) (59 mg) was obtained as 34% yield.

¹H NMR (300 MHz, CD₃OD) 7.38 (d, J=7.68 Hz, 1H), 7.28 (d, J=7.68 Hz, 1H), 6.96-6.87 (m, 3H), 4.54-4.28 (dd, 2H), 4.22 (s, 2H), 3.84 (s, 3H), 3.69 (q, J=7.14 Hz, 1H), 3.44 (m, 4H), 2.81 (s, 3H), 1.83 (m, 4H), 1.45 (d, J=7.14 Hz, 3H).

Synthesis of Example 49

—N-(2-methoxy-4-(3-((2-(4-methylpiperidin-1-yl)-6-(trifluoromethyl)pyridin-3-yl)methyl)ureido)benzyl)methanesulfonamide

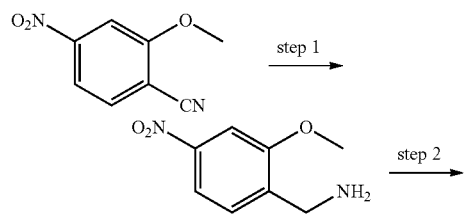

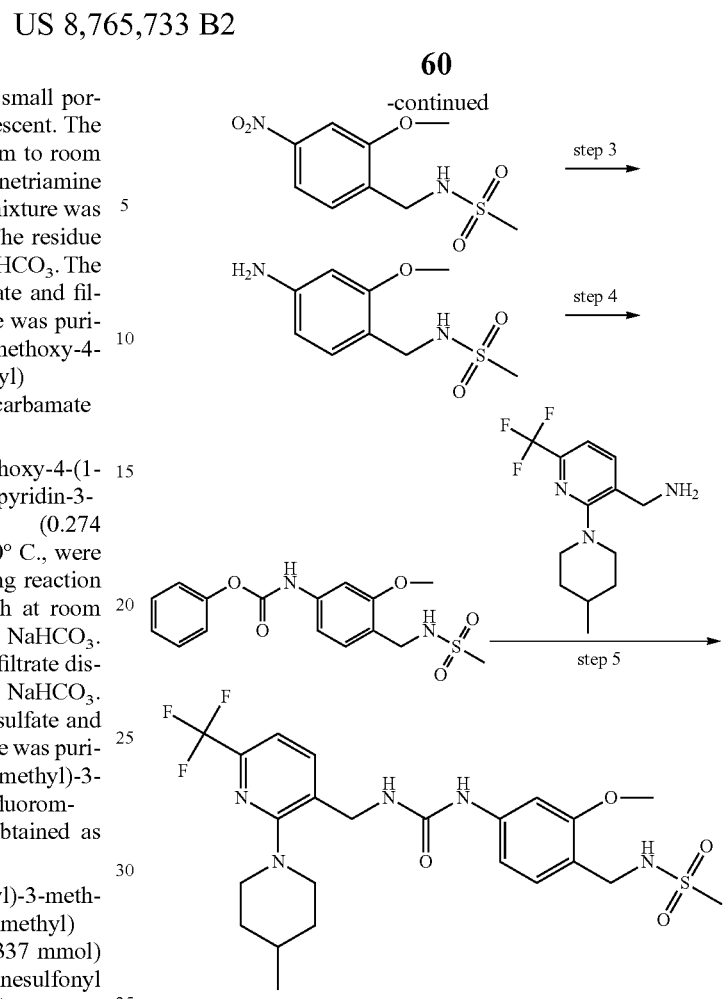

Step 1: 2-Methoxy-4-nitrobenzonitrile (1 equiv.) is dissolved in tetrahydrofuran and added 2 M borane-methyl sulfide complex in tetrahydrofuran (5 equiv.). The reaction is refluxed for 15 h and the reaction is cooled to 0° C. Water is drop wised carefully until remained borane is inactivated. Organic layer is extracted with dichloromethane, washed with brine, and concentrated. The mixture is purified by column chromatography (dichloromethane:methanol=10:1) and obtain (2-methoxy-4-nitrophenyl)methanamine as 45% yield.

Step 2: (2-Methoxy-4-nitrophenyl)methanamine is dissolved in pyridine and the reaction is cooled to 0° C. Methanesulfonyl chloride (2 equiv.) is drop wised and the reactant mixture is stirred at room temperature for 2 h. The reaction is quenched with 1N HCl and extracted with ethyl acetate three times. The combined organic layer is washed with brine, dried over magnesium sulfate and concentrated. A crude product is purified by column chromatography (dichloromethane:methanol=20:1) and N-(2-methoxy-4-nitrobenzyl)methanesulfonamide is obtained as 45% yield.

Step 3: 10% Palladium on carbon (one-tenth amount of the amide) is added to N-(2-methoxy-4-nitrobenzyl)methanesulfonamide in tetrahydrofuran and ethanol (1:1) solvent. Hydrogen gas is charged and the reaction is stirred at room temperature for 15 h. Palladium is removed by celite pad filtration. After evaporate solvent, it is purified by column chromatography (dichloromethane: methanol=10:1) and obtained N-(4-amino-2-methoxybenzyl)methanesulfonamide as 92% yield.

Step 4: Phenyl chloroformate (1.05 equiv.) is dropwised to N-(4-amino-2-methoxybenzyl)methanesulfonamide which is dissolved in tetrahydrofuran and acetonitril solution and pyridine (1.2 equiv.) is added. The reaction is stirred at room temperature for 3 h and water is added. Organic layer is extracted with ethylacetate, washed with water and dried over magnesium sulfate. The mixture is purified by column chromatography (dichloromethane:methanol=10:1) and obtain phenyl 3-methoxy-4-(methylsulfonamidomethyl)phenylcarbamate as 67% yield.

Step 5: Phenyl 3-methoxy-4-(methylsulfonamidomethyl) phenylcarbamate is dissolved in acetonitrile and (2-(4-methylpiperidin-1-yl)-6-(trifluoromethyl)pyridin-3-yl)methanamine (1 equiv.), dimethylaminopyridine (1 equiv.) is added to the solution. The reaction is processed at 50° C. for 15 h and water is added, extracted with ethylacetate, and purified by column chromatography (dichloromethane: methanol=10:1). N-(2-methoxy-4-(3-((2-(4-methylpiperidin-1-yl)-6-(trifluoromethyl)pyridin-3-yl)methyl)ureido)benzyl)-methanesulfonamide (example 49) is obtained as 79% yield.

$^1$H NMR (300 MHz, DMSO) δ 7.76 (d, 1H, J=9.0 Hz), 7.43 (d, 1H, J=6.0 Hz), 7.20 (d, 1H, J=6.0 Hz), 7.13 (s, 1H), 6.84 (d, 1H, J=9.0 Hz), 4.31 (d, 2H, J=6.0 Hz), 4.02 (d, 2H, J=6.0 Hz), 3.72 (s, 3H), 2.77 (s, 3H), 1.71 (d, 2H, J=9.0 Hz), 1.54 (q, 1H), 1.29 (d, 2H, J=9.0 Hz), 0.95 (d, 3H, J=9.0 Hz).

Synthesis of Example 50

-2-(3-methoxy-4-(methylsulfonamidomethyl)phenyl)-N-((2-(4-methylpiperidin-1-yl)-6-(trifluoromethyl)pyridin-3-yl)methyl)propanamide

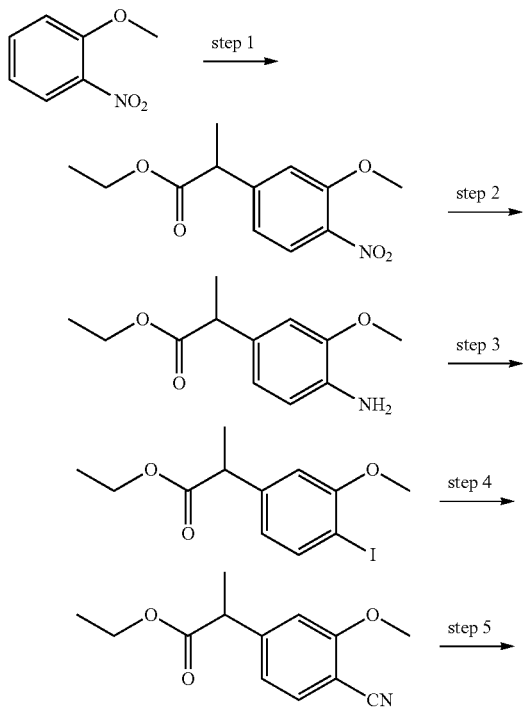

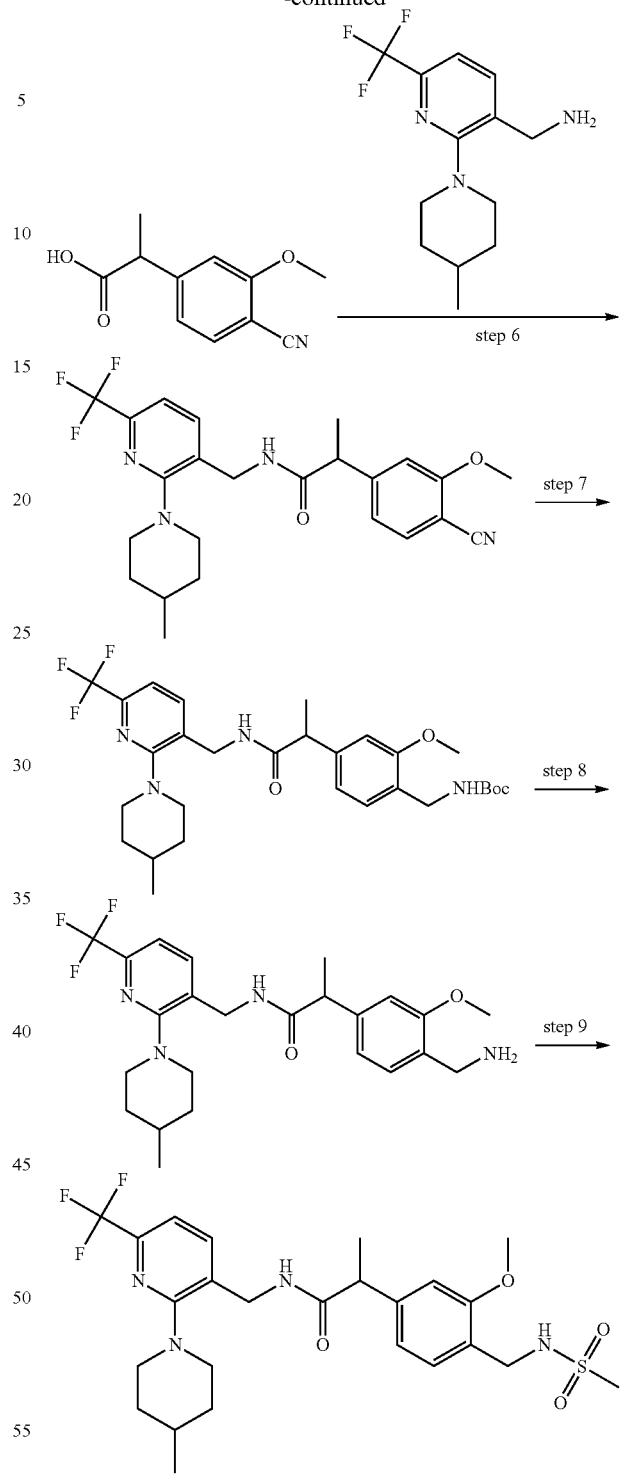

Step 1: To a stirred solution of 1-methoxy-2-nitrobenzene (3 g, 19.59 mmol) in dimethylformamide were added potassium tert-butoxide (8.792 g, 78.36 mmol) and ethyl 2-chloropropionate (2.5 ml, 19.59 mmol) while maintaining temperature below −30° C. The reaction mixture was stirred for 5 min at −30° C., then ethyl 2-chloropropionate (0.25 mL, 1.959 mmol) was added to mixture. The reaction mixture was stirred for 10 min at room temperature. The residue was dissolved in ethyl acetate and washed with water and brine. The organic layer was dried ogver magnesium sulfate and filtered. The filtrate removed in vacuo. The crude was purified by column chromatography. Ethyl 2-(3-methoxy-4-nitrophenyl)propanoate (683 mg) was obtained as 14% yield.

Step 2: To a stirred solution of ethyl 2-(3-methoxy-4-nitrophenyl)propanoate (683 mg, 2.697 mmol) in tetrahydrofuran and ethanol as co-solvent were added 10% Pd/C (70 mg). The mixture was charged with $H_2$ (gas) balloon. The resulting mixture was stirred for 15 h, then filtered using celite. The filtrate removed in vacuo. The crude was purified by column chromatography. Ethyl 2-(4-amino-3-methoxyphenyl)propanoate (447 mg) was obtained as 74% yield.

Step 3: To a stirred solution of ethyl 2-(4-amino-3-methoxyphenyl)propanoate (447 mg, 2.002 mmol) in acetonitrile and water were added p-toluenesulfonic acid monohydrate (1.142 g, 6.006 mmol), sodium nitrite (276 mg, 4.004 mmol) and potassium iodide (831 mg, 5.005 mmol). The reaction mixture was stirred for 4 h at room temperature. The mixture dissolved in ethyl acetate and washed with water and brine. The organic layer was dried over magnesium sulfate and filtered. The filtrate removed in vacuo. The crude was purified by column chromatography. Ethyl 2-(4-iodo-3-methoxyphenyl)propanoate (468 mg) was obtained as 70% yield.

Step 4: To a stirred solution of ethyl 2-(4-iodo-3-methoxyphenyl)propanoate (626 mg, 1.873 mmol) in dimethylformamide were added zinc cyanide (227 mg, 1.929 mmol) and tetrakis(triphenylphosphine) palladium (216 mg, 0.1873 mmol). The reaction mixture was stirred for 36 h at 120° C., then cooled to room temperature, diluted with ethyl acetate. The mixture was filtered using celite pad. The filtrate dissolved in ethyl acetate and extracted with $NaHCO_3$. The organic layer was dried over magnesium sulfate and filtered. The filtrate removed in vacuo. The crude was purified by column chromatography. Ethyl 2-(4-cyano-3-methoxyphenyl)propanoate (222 mg) was obtained as 51% yield.

Step 5: To a stirred solution of ethyl 2-(4-cyano-3-methoxyphenyl)propanoate (222 mg, 0.952 mmol) in co-solvent with tetrahydrofuran and water (1:1) were added sodium hydroxide (95 mg, 2.38 mmol). The reaction mixture was stirred for 15 h at room temperature, then acidified to pH 3~4 with acetic acid. The residue dissolved in ethyl acetate and washed with water and brine. The organic layer was dried over magnesium sulfate and filtered. The filtrate removed in vacuo. The crude was purified by column chromatography. 2-(4-Cyano-3-methoxyphenyl)propanoic acid (188 mg) was obtained as 96% yield.

Step 6: To a stirred solution of 2-(4-cyano-3-methoxyphenyl)propanoic acid (94 mg, 0.458 mmol) and (2-(4-methylpiperidin-1-yl)-6-(trifluoromethyl)pyridin-3-yl)methanamine (138 mg, 0.5038 mmol) in acetonitrile were added N-(3-dimethylaminopropyl)-N'-ethylcarbodiimide (132 mg, 0.687 mmol), N-hydroxybenzotriazole (93 mg, 0.687 mmol) and triethylamine (0.16 mL, 1.145 mmol). The reaction mixture was stirred for 15 h at room temperature. The residue dissolved in ethyl acetate and washed with water and brine. The organic layer was dried over magnesium sulfate and filtered. The filtrate removed in vacuo. The crude was purified by column chromatography. 2-(4-Cyano-3-methoxyphenyl)-N-((2-(4-methylpiperidin-1-yl)-6-(trifluoromethyl)pyridin-3-yl)methyl)propanamide (218 mg) was obtained as 99% yield.

Step 7: To a stirred solution of 2-(4-cyano-3-methoxyphenyl)-N-((2-(4-methylpiperidin-1-yl)-6-(trifluoromethyl)pyridin-3-yl)methyl)propanamide (218 mg, 0.473 mmol) in methanol, cooled to 0° C., were added di-tert-butyl dicarbonate (206 mg, 0.946 mmol) and nickel(II) chloride hexahydride (11 mg, 0.0473 mmol). Sodium borohydride (125 mg, 3.311 mmol) was added in small portions. The resulting reaction mixture was allowed to warm to room temperature and left to stir for 1 hour. Diethylenetriamine (0.05 mL, 0.473 mmol) was added to the mixture. The mixture was stirred for 1 h. The solvent was evaporated. The residue dissolved in ethyl acetate and extracted with $NaHCO_3$. The organic layer was dried over magnesium sulfate and filtered. The filtrate removed in vacuo. The crude was purified by column chromatography. Tert-butyl 2-methoxy-4-(1-((2-(4-methylpiperidin-1-yl)-6-(trifluoromethyl)pyridin-3-yl)methylamino)-1-oxopropan-2-yl)benzylcarbamate (155 mg) was obtained as 58% yield.

Step 8: To a stirred solution of tert-butyl 2-methoxy-4-(1-((2-(4-methylpiperidin-1-yl)-6-(trifluoromethyl)pyridin-3-yl)methylamino)-1-oxopropan-2-yl)benzylcarbamate (155 mg, 0.274 mmol) in dichloromethane (4 mL), cooled to 0° C., was added trifluoroacetic acid (1 mL). The resulting reaction mixture was stirred for 2 h at 0° C. and 2 h at room temperature, then basified to pH 8~9 with $NaHCO_3$. The mixture was filtered using celite pad. The filtrate dissolved in dichloromethane and extracted with $NaHCO_3$. The organic layer was dried over magnesium sulfate and filtered. The filtrate removed in vacuo. The crude was purified by column chromatography to obtain 2-(4-(aminomethyl)-3-methoxyphenyl)-N-((2-(4-methylpiperidin-1-yl)-6-(trifluoromethyl)pyridin-3-yl)methyl)propanamide (65 mg, 51%).

Step 9: To a stirred solution of 2-(4-(aminomethyl)-3-methoxyphenyl)-N-((2-(4-methylpiperidin-1-yl)-6-(trifluoromethyl)pyridin-3-yl)methyl)propanamide (65 mg, 0.139 mmol) in pyridine, cooled to 0° C., was added methanesulfonyl chloride (65 mg). The resulting reaction mixture was stirred for 15 h at room temperature. The mixture dissolved in dichloromethane and washed with 1N HCl. The organic layer was dried over magnesium sulfate and filtered. The filtrate removed in vacuo. The crude was purified by column chromatography. 2-(3-Methoxy-4-(methylsulfonamidomethyl)phenyl)-N-((2-(4-methylpiperidin-1-yl)-6-(trifluoromethyl)pyridin-3-yl)methyl)propanamide (example 50) (34 mg) was obtained as 45% yield.

$^1$H NMR (300 MHz, $CDCl_3$) 7.44 (d, 1H, J=5.73 Hz, Ar), 7.21 (d, 1H, J=5.79 Hz, Ar), 7.15 (d, 1H, J=5.7 Hz, Ar), 6.83 (d, 1H, J=5.7 Hz, Ar), 6.78 (s, 1H, Ar), 6.14 (t, 1H, NH), 4.80 (t, 1H, NH), 4.43 (d, 2H, $CH_2$), 4.24 (d, 2H, $CH_2$), 3.80 (s, 3H, $OCH_3$), 3.56 (q, 1H), 3.25 (m, 2H, piperidine), 2.80 (s, 3H, mesyl), 2.76 (m, 2H, piperidine), 1.67 (t, 2H), 1.5 (br, 1H), 1.22 (m, 2H), 0.94 (d, 3H).

Synthesis of Example 51

-2-(3-methyl-4-(methylsulfonamidomethyl)phenyl)-N-((2-(pyrrolidin-1-yl)-6-(trifluoromethyl)pyridin-3-yl)methyl)propanamide

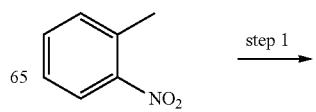

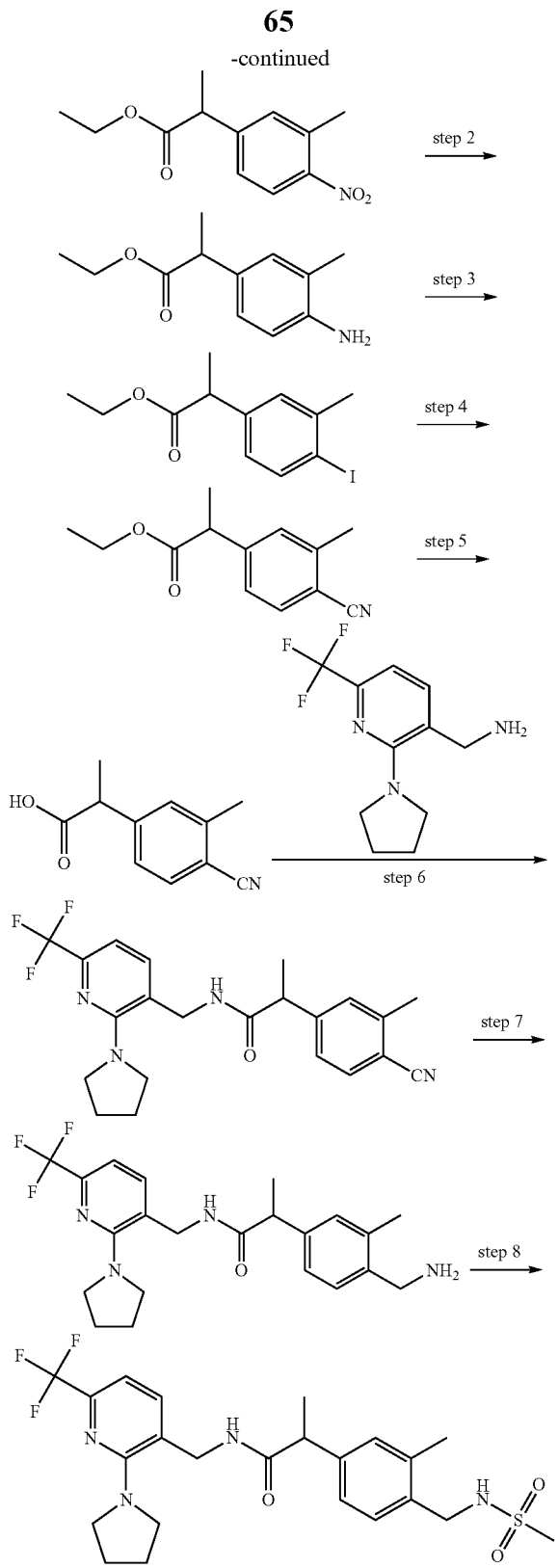

Step 1: To a stirred solution of added potassium tert. butoxide (2.05 g, 18.3 mmol) in dimethylformamide (10 mL) were slowly added the mixture of 1-methyl-2-nitrobenzene (1 g, 7.29 mmol) and ethyl-2-chloropropionate(0.98 mL, 7.70 mmol) at −30° C. The reaction mixture was stirred for 10 min and warmed to room temperature. The residue was dissolved with ethyl acetate and neutralized with NaHCO$_3$. The organic layer was washed with water two times, then dried over magnesium sulfate and filtered. The filtrate removed in vacuo. The crude was purified by column chromatography. Ethyl 2-(3-methyl-4-nitrophenyl)propanoate (1.2 g) was obtained as 70% yield.

Step 2: Ethyl 2-(3-methyl-4-nitrophenyl)propanoate (1.2 g, 5.05 mmol) was dissolved in methanol and tetrahydrofuran (1:1, 15 mL). 10% Pd/C (180 mg, 10%) was added to it. The resulting mixture was stirred at room temperature for 3 h under H$_2$. TLC showed complete consumption of starting material. The mixture was filtered through celite bed and the filtrate was concentrated under reduced pressure. The crude was purified by column chromatography to give pure compound ethyl 2-(4-amino-3-methylphenyl)propanoate (944 mg, 90%).

Step 3: To a stirred solution of ethyl 2-(4-amino-3-methylphenyl)propanoate (944 mg, 4.55 mmol) in acetonitrile, p-TsOH.H$_2$O (2.62 g, 13.66 mmol) was dropped slowly. The reaction mixture was activated for 10 min. Then NaNO$_2$ (629 mg, 9.11 mmol) in water was added dropwise. The mixture was stirred for 10 min. Then potassium iodide (1.89 g, 11.39 mmol) in water was added slowly dropwise. The reaction mixture was stirred at room temperature for 4 h. After the reaction is complete, 1 M NaOH solution was added to neutralize the reaction then ethyl acetate and water was used for work up. The organic layer was washed with water two times, then dried over magnesium sulfate and filtered. The filtrate removed in vacuo. The crude was purified by column chromatography. Ethyl 2-(4-iodo-3-methyl phenyl)propanoate (1.22 g) was obtained as 84% yield.

Step 4: To a stirred solution of ethyl 2-(4-iodo-3-methylphenyl)propanoate (1.22 g, 5.34 mmol) in anhydrous dimethylformamide were added zinc cyanide (645 mg, 5.50 mmol) and tetrakis(triphenylphosphine) palladium (617 mg, 0.53 mmol). The reaction mixture was refluxed for overnight then cooled to room temperature. The mixture was filtered using celite pad and the filtrate was evaporated. The residue was diluted with ethyl acetate and washed with water and brine. The organic layer was dried over magnesium sulfate and filtered. The filtrate was concentrated under reduced pressure to get the crude. The crude was purified by column chromatography. Ethyl 2-(4-cyano-3-methylphenyl)propanoate(1.05 g) was obtained as 90% yield.

Step 5: To a stirred solution of ethyl 2-(4-cyano-3-methylphenyl)propanoate (1.05 g, 4.82 mmol) in co-solvent with tetrahydrofuran and water (1:1) were added sodium hydroxide (482 mg, 12.06 mmol). The reaction mixture was stirred for overnight at room temperature, then acidified to pH 3~4 with acetic acid. The residue was diluted with ethyl acetate and washed with water and brine. The organic layer was dried over magnesium sulfate and filtered. The filtrate removed in vacuo. The crude 2-(4-cyano-3-methylphenyl)propanoic acid (1.1 g) was obtained as 99% yield.

Step 6: To a stirred solution of 2-(4-cyano-3-methylphenyl) propanoic acid (100 mg, 0.53 mmol) in acetonitrile were added N-(3-dimethylaminopropyl)-N'-ethylcarbodiimide (152 mg, 0.80 mmol), 1-hydroxybenzotriazole (107 mg, 0.80 mmol), (2-(pyrrolidin-1-yl)-6-(trifluoromethyl)pyridin-3-yl)methanamine (143 mg, 0.58 mmol) and triethylamine (0.18 mL, 1.33 mmol). The reaction mixture was stirred for overnight at room temperature. The mixture was diluted with ethyl acetate and washed with water and brine. The organic layer was dried over magnesium sulfate and filtered. The filtrate removed in vacuo. The crude was purified by column chromatography. 2-(4-Cyano-3-methylphenyl)-N-((2-(pyrrolidin-1-yl)-6-(trifluoromethyl)pyridin-3-yl)methyl)propanamide (189 mg) was obtained as 86% yield.

Step 7: To a stirred solution of 2-(4-cyano-3-methylphenyl)-N-((2-(pyrrolidin-1-yl)-6-(trifluoromethyl)pyridin-3-yl)methyl)propanamide (90 mg, 0.22 mmol) in ethanol was cooled to 0° C. and added NiCl$_2$.6H$_2$O (51 mg, 0.22 mmol) and stirred more than 15 mins. Sodium borohydride (57 mg, 1.51 mmol) was then added in small portions. The reaction was exothermic and effervescent. The resulting reaction mixture was allowed to warm to room temperature and left to stir for 2 h. The mixture was filtered using celite pad. The filtrate was concentrated was evaporated. The residue was dissolved in ethyl acetate and washed with water and brine, but when it does not separate easily, small amount of 1N HCl and saturated NaHCO$_3$ was used. The organic layer was dried over magnesium sulfate and filtered. The filtrate removed in vacuo. The crude was purified by column chromatography. 2-(4-(Aminomethyl)-3-methylphenyl)-N-((2-(pyrrolidin-1-yl)-6-(trifluoromethyl)pyridin-3-yl)methyl)propanamide (109 mg) was obtained as 99% yield.

Step 8: To a stirred solution of 2-(4-(aminomethyl)-3-methylphenyl)-N-((2-(pyrrolidin-1-yl)-6-(trifluoromethyl)pyridin-3-yl)methyl)propanamide (109 mg, 0.26 mmol) in pyridine was added methanesulfonylchloride (0.03 mL, 0.42 mmol) The reaction mixture was stirred for overnight at room temperature. The mixture was diluted with ethyl acetate and washed with 1 N HCl and brine. The organic layer was dried over magnesium sulfate and filtered. The filtrate removed in vacuo. The crude was purified by column chromatography. 2-(3-Methyl-4-(methylsulfonamidomethyl)phenyl)-N-((2-(pyrrolidin-1-yl)-6-(trifluoromethyl)pyridin-3-yl)methyl)propanamide (example 51) (60 mg) was obtained as 46% yield.

$^1$H NMR (300 MHz, DMSO) 8.39 (bs, 1H, NH), 7.43 (d, 1H, J=7.5 Hz, Ar), 7.35 (bs, 1H, NH), 7.24 (d, 1H, J=7.8Hz, Ar), 7.12 (m, 2H, Ar), 7.00 (d, 1H, J=7.5 Hz, Ar), 4.30 (bt, 2H, J=6.6 Hz, CH$_2$), 4.10 (s, 2H, CH), 3.63 (m, 1H, CH), 2.89 (s, 3H, Ms), 2.28 (s, 3H, CH$_3$), 1.79 (m, 4H, pyrrolidine), 1.32 (d, 3H, J=7.2 Hz, CH$_3$).

Synthesis of Example 52

—N-(2-methyl-4-(3-((2-(pyrrolidin-1-yl)-6-(trifluoromethyl)pyridin-3-yl)methyl)ureido)benzyl)methanesulfonamide

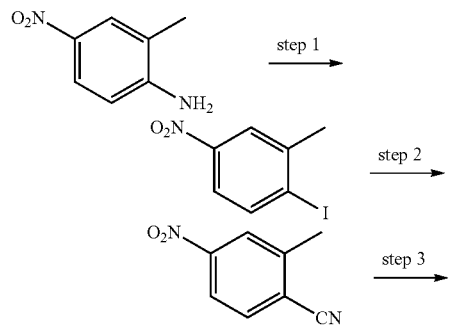

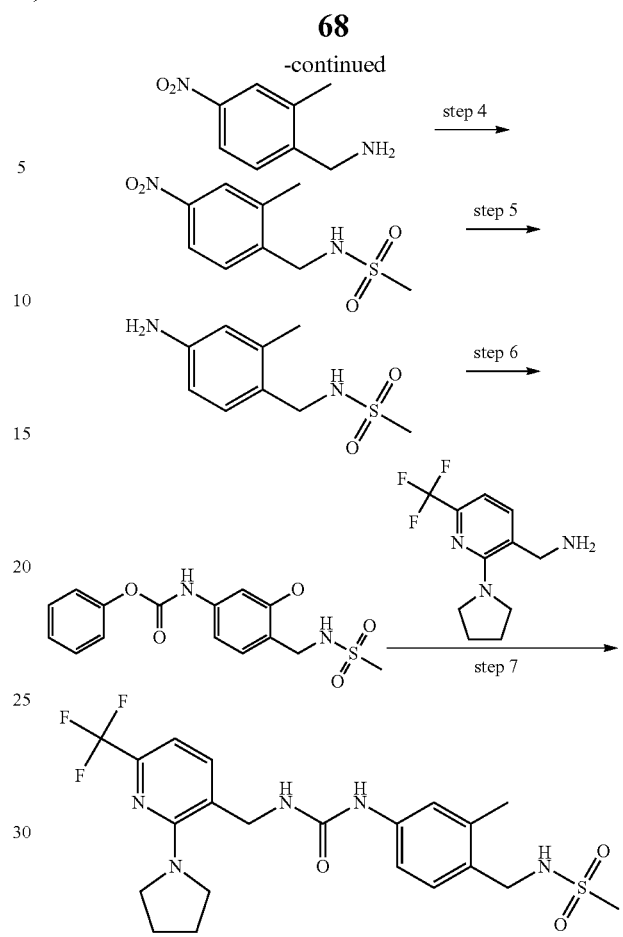

Step 1: To a stirred solution of 2-methyl-4-nitroaniline (500 mg, 3.286 mmol) in acetonitrile and water were added p-TsOH.H$_2$O (1.875 g, 9.858 mmol), sodium nitrite (453 mg, 6.572 mmol) and potassium iodide (1.363 g, 8.215 mmol). The reaction mixture was stirred for 4 h at room temperature. The mixture dissolved in ethyl acetate and washed with water and brine. The organic layer was dried over magnesium sulfate and filtered. The filtrate removed in vacuo. The crude was purified by column chromatography. 1-Iodo-2-methyl-4-nitrobenzene (812 mg) was obtained as 94% yield.

Step 2: To a stirred solution of 1-iodo-2-methyl-4-nitrobenzene (812 mg, 3.087 mmol) in dimethylformamide were added zinc cyanide (544 mg, 4.630 mmol) and tetrakis(triphenylphosphine) palladium (713 mg, 0.6174 mmol). The reaction mixture was stirred for 24 h at 120° C., then cooled to room temperature, diluted with ethylacetate. The mixture was filtered using celite pad. The filtrate dissolved in ethyl acetate and extracted with NaHCO$_3$. The organic layer was dried over magnesium sulfate and filtered. The filtrate removed in vacuo. The crude was purified by column chromatography. 2-Methyl-4-nitrobenzonitrile (407 mg) was obtained as 81% yield.

Step 3: To a stirred solution of 2-methyl-4-nitrobenzonitrile (407 mg, 2.510 mmol) in tetrahydrofuran was added 2 M borane-methyl sulfide complex in tetrahydrofuran (2.1 mL). The reaction mixture was stirred for 15 h at 70° C. The mixture was cooled to room temperature, then quenched by water. The mixture dissolved in ethyl acetate and washed with water and brine. The organic layer was dried over magnesium sulfate and filtered. The filtrate removed in vacuo. The crude was purified by column chromatography. (2-Methyl-4-nitrophenyl)methanamine (178 mg) was obtained as 43% yield.

Step 4: To a stirred solution of (2-methyl-4-nitrophenyl)methanamine (178 mg, 1.071 mmol) in pyridine, cooled to 0° C., were added methanesulfonyl chloride (0.16 mL, 2.0349 mmol). The resulting reaction mixture was stirred for 2 h. The mixture dissolved in dichloromethane and washed with 1N HCl. The organic layer was dried over magnesium sulfate and filtered. The filtrate removed in vacuo. The crude was purified by column chromatography. N-(2-methyl-4-nitrobenzyl)methanesulfonamide (100 mg) was obtained as 38% yield.

Step 5: To a stirred solution of N-(2-methyl-4-nitrobenzyl)methanesulfonamide (100 mg, 0.409 mmol) in tetrahydrofuran and ethanol as co-solvent were added 10% palladium on carbon (40 mg). The mixture was charged with $H_2$ (gas) balloon. The resulting mixture was stirred for 24 h, then filtered using celite. The filtrate removed in vacuo. The crude was purified by column chromatography. N-(4-amino-2-methylbenzyl)methanesulfonamide (61 mg) was obtained as 70% yield.

Step 6: To a stirred solution of N-(4-amino-2-methylbenzyl)methanesulfonamide (61 mg, 0.285 mmol) in tetrahydrofuran and acetonitrile as co-solvent were added phenylchloroformate (0.04 mL, 0.299 mmol) and pyridine (0.03 mL, 0.342 mmol). The reaction mixture was stirred for 3 h at room temperature. The mixture dissolved in ethyl acetate and washed with water and brine. The organic layer was dried over magnesium sulfate and filtered. The filtrate removed in vacuo. The crude was purified by column chromatography. Phenyl 3-methyl-4-(methylsulfonamidomethyl)phenyl carbamate (93 mg) was obtained as 98% yield.

Step 7: To a stirred solution of phenyl 3-methyl-4-(methylsulfonamidomethyl)phenylcarbamate (46 mg, 0.137 mmol) and (2-(pyrrolidin-1-yl)-6-(trifluoromethyl)pyridin-3-yl)methanamine (34 mg, 0.137 mmol) in acetonitrile were added dimethylaminopyridine (17 mg, 0.137 mmol). The reaction mixture was stirred for 15 h at 50° C. The mixture dissolved in ethyl acetate and washed with water and brine. The organic layer was dried over magnesium sulfate and filtered. The filtrate removed in vacuo. The crude was purified by column chromatography. N-(2-methyl-4-(3-((2-(pyrrolidin-1-yl)-6-(trifluoromethyl)pyridin-3-yl)methyl)ureido)benzyl)methanesulfonamide (example 52) (57 mg) was obtained as 86% yield.

$^1$H NMR (300 MHz, DMSO) 8.60 (s, 1H), 7.65 (d, J=7.68 Hz, 1H), 7.27-7.09 (m, 5H), 6.61 (br t, 1H), 4.39 (d, J=5.31 Hz, 2H), 4.04 (d, J=5.88 Hz, 2H), 3.52 (t, J=6.42 Hz, 4H), 2.84 (s, 3H), 2.24 (s, 3H), 1.89 (t, J=6.42 Hz, 4H).

Synthesis of Example 53

—N-(2-methyl-4-(3-((2-(4-methylpiperidin-1-yl)-6-(trifluoromethyl)pyridin-3-yl)methyl)ureido)benzyl)methanesulfonamide

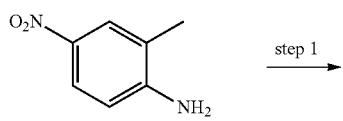

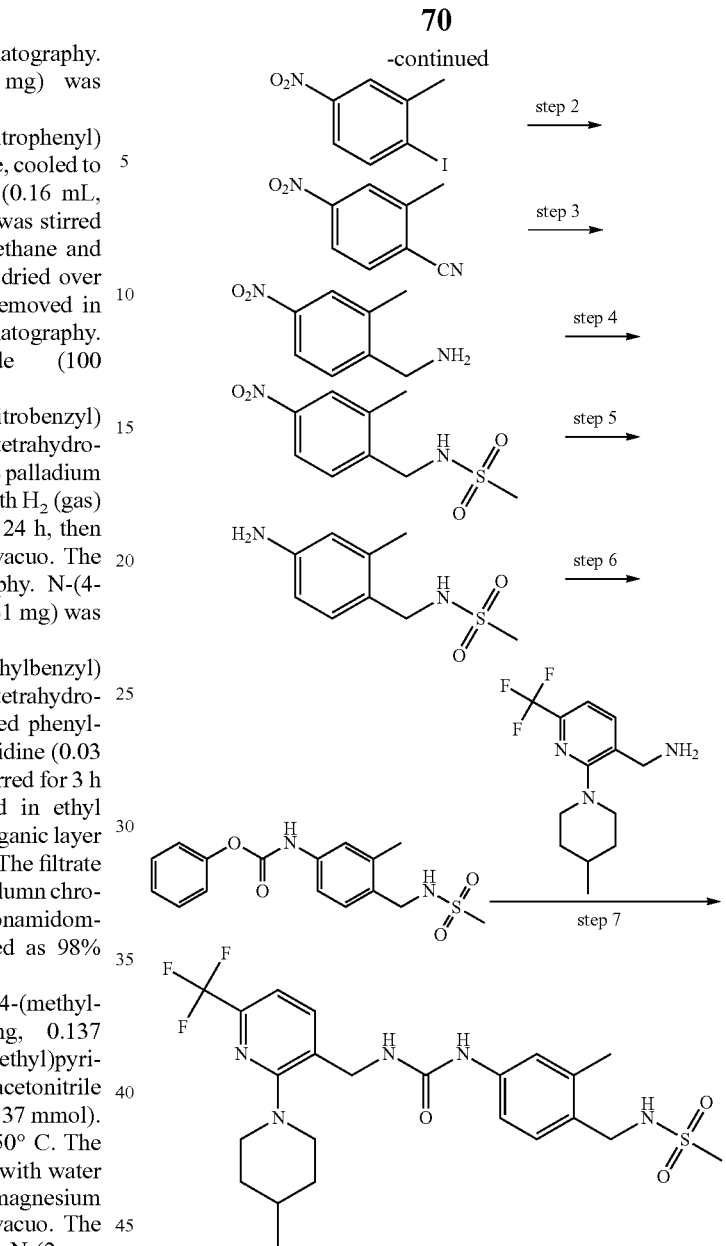

Step 1: A solution of p-TsOH H$_2$O (3 equiv.) in acetonitrile was added to a solution of 2-methyl-4-nitroaniline (1 equiv) in acetonitrile. The resulting suspension of amine salt was cooled to 10-15° C. and to this was added, gradually, a solution of NaNO$_2$ (2 equiv.) and potassium iodide (2.5 equiv.) in water. The reaction mixture was stirred for 10 min then allowed to come to 20° C. and stirred until the starting material was consumed. After 4 h, water, NaHCO$_3$ (until pH=9-10) was added and extracted with ethyl acetate. The organic layer was washed with water, dried over magnesium sulfate and concentrated in vacuo. The residue was purified on a silica gel column using ethylacetate-hexane as solvent system to give 1-iodo-2-methyl-4-nitrobenzene.

Step 2: 1-Iodo-2-methyl-4-nitrobenzene, Pd$_2$(dba)$_3$, zinc cyanide were placed in round flask charged with N$_2$ and dissolved in dimethylformamide. The reaction mixture was stirred at 120° C. for 24 h and cooled to room temperature. Extracted with ethyl acetate and washed with 2 N NH₄OH solution. The organic layer was washed with water, dried over sodium sulfate and concentrated in vacuo. The residue was purified on a silica gel column using ethylacetate-hexane as solvent system to give 2-methyl-4-nitrobenzonitrile.

Step 3: To the solution of 2-methyl-4-nitrobenzonitrile in tetrahydrofuran, 2 M borane-methyl sulfide complex in tetrahydrofuran was drop-wised slowly and the mixture refluxed during a day. After cooling the reaction to room temperature, water was drop-wised to removed left borane and extracted with ethyl acetate, washed with water several times. The crude resultant was purified by column chromatography and (2-methyl-4-nitrophenyl)methanamine was obtained.

Step 4: Pyridine was added to the solution of (2-methyl-4-nitrophenyl)methanamine in dichloromethane, followed by methanesulfonylchloride. The reaction mixture was stirred for 2 h at room temperature. The mixture was diluted with ethyl acetate and washed with 1N HCl and brine. The organic layer was dried over magnesium sulfate and filtered. The filtrate removed in vacuo. The crude was purified by column chromatography. N-(2-methyl-4-nitrobenzyl)methanesulfonamide was obtained.

Step 5: 10% Palladium on carbon was added to N-(2-methyl-4-nitrobenzyl)methanesulfonamide solution in methanol and the mixture was charged with H₂. After stirring the reaction mixture for 15 h, the mixture was filtered using Celite and purified by column chromatography to get N-(4-amino-2-methylbenzyl)methanesulfonamide in hand.

Step 6: To a stirred solution of N-(4-amino-2-methylbenzyl)methanesulfonamide in acetone/tetrahydrofuran was added pyridine at 0° C. The reaction mixture was stirred for 3 h at room temperature. The residue was dissolved in ethyl acetate and washed with water and brine. The organic layer was dried over magnesium sulfate and filtered. The filtrate removed in vacuo. The crude was purified by column chromatography and phenyl 3-methyl-4-(methylsulfonamidomethyl)phenylcarbamate was obtained.

Step 7: To a stirred solution of phenyl 3-methyl-4-(methylsulfonamidomethyl)-phenylcarbamate in acetonitrile was added (2-(4-methylpiperidin-1-yl)-6-(trifluoromethyl)pyridin-3-yl)methanamine derivatives synthesized previously, followed by dimethylaminopyridine (1 equiv.). The reaction mixture was stirred for 15 h at 50° C. The residue was dissolved in dichloromethane and washed with water and brine. The organic layer was dried over magnesium sulfate and filtered. The filtrate removed in vacuo. After column chromatography, the N-(2-methyl-4-(3-((2-(4-methylpiperidin-1-yl)-6-(trifluoromethyl)pyridin-3-yl)methyl)ureido)benzyl)methanesulfonamide (example 53) was obtained.

¹H NMR (400 MHz, CDCl₃) δ 7.45(d, 1H, J=8.00 Hz, Ar—H), 7.18-7.22(m, 3H, Ar—H), 7.03(d, 1H, Ar—H), 6.62(s, 1H), 5.58 (bs, 1H, α-NH), 4.67 (bs, 1H, Ar-α-NH), 4.47 (m, 3H), 4.20 (d, 2H, J=4.00 Hz, α-CH₂), 3.48 (d, 2H, J=8.00), 2.79-2.93 (m, 7H), 2.29(s, 3H, Ar—CH₃), 1.25-1.68 (m, 5H), 0.96 (d, 3H, J=4.00 Hz).

Synthesis of Example 54

-2-(4-(ethylsulfonamidomethyl)-3-fluorophenyl)-N-((2-(pyrrolidin-1-yl)-6-(trifluoromethyl)pyridin-3-yl)methyl)propanamide

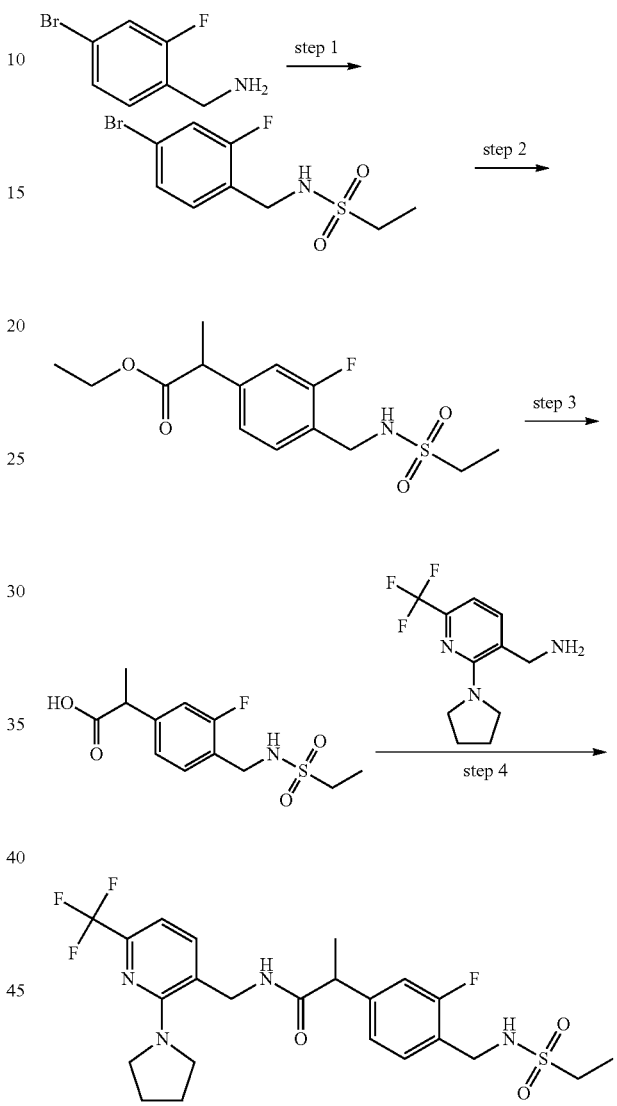

Step 1: (4-Bromo-2-fluorophenyl)methanamine (924 mg, 4.53 mmol) was dissolved in pyridine and ethane sulfonyl chloride (0.82 mL, 8.60 mmol) was added to the solution at 0° C. The mixture was stirred for 1 h at 0° C. Then, the mixture was quenched with 1N HCl and extracted with ethyl acetate. Drying over magnesium sulfate and evaporation of the ethyl acetate and purified by column chromatography gave N-(4-bromo-2-fluorobenzyl)-ethanesulfonamide in pure form (1.06 g, 79%).

Step 2: To a solution of N-(4-bromo-2-fluorobenzyl)ethane-sulfonamide (305 mg, 1.03 mmol) in dimethylformamide, Manganese (113 mg, 2.06 mmol), (2,2'-Bipyridine)nickel (II)-dibromide (27 mg, 0.07 mmol), ethyl 2-chloropropanoate (0.17 mL, 1.34 mmol) was added. It was followed by addition of trifluoroacetic acid (0.002 mL, 0.028 mmol). The mixture was stirred for 24 h at 65° C. The reaction mixture was quenched by concentrated HCl (7 drops). Then it was extracted with diethyl ether, dried over magnesium sulfate, the solvent was evaporated in vacuo. It was purified by column chromatography to obtain ethyl 2-(4-(ethylsulfonamidomethyl)-3-fluorophenyl)propanoate in pure form (65 mg, 20%).

Step 3: To a solution of ethyl 2-(4-(ethylsulfonamidomethyl)-3-fluorophenyl)propanoate (60 mg, 0.189 mmol) in tetrahydrofuran and water co-solvent, sodium hydroxide (19 mg) was added at room temperature. The mixture was stirred for overnight and extracted with ethyl acetate, dried over magnesium sulfate, the solvent was evaporated in vacuo. It was purified by column chromatography to give 2-(4-(ethylsulfonamidomethyl)-3-fluorophenyl)propanoic acid (55 mg).

Step 4: 2-(4-(Ethylsulfonamidomethyl)-3-fluorophenyl)propanoic acid (60 mg, 0.207 mmol) and (2-(pyrrolidin-1-yl)-6-(trifluoromethyl)pyridin-3-yl)methanamine (57 mg, 0.228 mmol) were dissolved in 1,4-dioxane. Followed by addition of N-hydroxybenzotriazole (39 mg, 0.285 mmol) and N-(3-dimethylaminopropyl)-N'-ethylcarbodiimide (55 mg, 0.285 mmol) and triethylamine (0.066 mL, 0.475 mmol). The reaction mixture was stirred for overnight, quenched by water and extracted with ethyl acetate. Drying over magnesium sulfate, evaporation of the ethyl acetate and purification by column chromatography gave 2-(4-(ethylsulfonamidomethyl)-3-fluorophenyl)-N-((2-(pyrrolidin-1-yl)-6-(trifluoromethyl)pyridin-3-yl)methyl)propanamide (example 54) (55 mg, 47%).

$^1$H—NMR (300 MHz, CDCl$_3$): δ 7.37 (d, 1 H, J=7.86 Hz, Ar—H), 7.33 (s, 1 H, Ar—H), 7.05 (m, 2 H, Ar—H), 6.94 (d, 1 H, J=7.50 Hz, Ar—H), 5.65 (m, 1 H, amide-NH), 4.51 (m, 1 H, amide-NH), 4.46 (d, 2 H, J=5.28 Hz, Ar—CH$_2$), 4.33 (d, 2 H, J=6.21 Hz, Ar—CH$_2$), 3.55(q, 1 H, J=7.14 Hz, amide-α-H), 3.42 (m, 4 H, pyrrole-H), 2.98 (q, 2 H, J=7.32 Hz, ethanesulfonly-2H), 1.85 (m, 4 H, pyrrole-H), 1.51 (d, 3 H, J=6.93 Hz, amide-3H), 1.33 (t, 3 H, J=7.32 Hz ethanesulfonly-3H)

Synthesis of Example 55

-2-(4-(ethylsulfonamidomethyl)-3-fluorophenyl)-N-((2-(4-methylpiperidin-1-yl)-6-(trifluoromethyl)pyridin-3-yl)methyl)propanamide

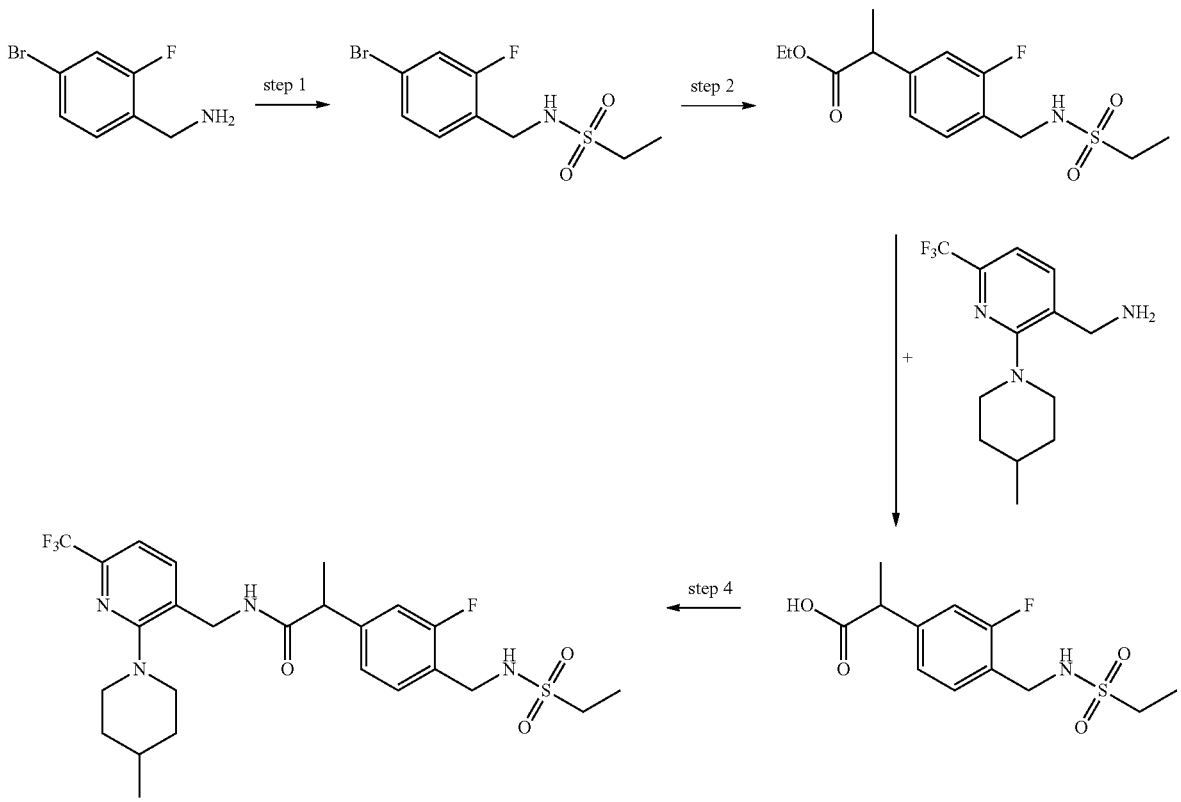

Step 1-3: according to example 54.

Step 4: 2-(4-(Ethylsulfonamidomethyl)-3-fluorophenyl)propanoic acid (55 mg , 0.19 mmol) and (2-(4-methylpiperidin-1-yl)-6-(trifluoromethyl)pyridin-3-yl)methanamine (57 mg, 0.209 mmol) was dissolved in 1,4-dioxane, followed by addition of 1-hydroxybenzotriazole (39 mg, 0.285 mmol), 1-ethyl-3-(3-dimethylaminopropyl) carbodiimide (55 mg, 0.285 mmol) and triethylamine (0.066 mL, 0.475 mmol). The reaction mixture was stirred for overnight and then quenched by water and extracted with ethyl acetatde. Drying over magnesium sulfate, evaporation of the organic solvent and purified by column chromatography (silica gel: 100-200 mesh, eluent: ethyl acetate/n-hexane 5:1) gave the compound 2-(4-

(ethylsulfonamidomethyl)-3-fluorophenyl)-N-((2-(4-methylpiperidin-1-yl)-6-(trifluoromethyl)pyridin-3-yl)methyl)propanamide (example 55) (85 mg, 83%).

$^1$H—NMR (CDCl$_3$) 7.47 (d, 1H, Ar, J=7.50 Hz), 7.37 (t, 1H, Ar), 7.20 (d, 1H, Ar, J=7.68 Hz), 7.07 (m, 2H), 6.22 (m, 1H), 4.50 (m, 1H), 4.47 (d, 2H , 5.85 Hz), 4.32 (d, 2H, J=6.24 Hz), 3.60 (q, 1H , J=6.96 Hz), 3.33 (m, 2H), 3.01 (q, 2H, J=7.32 Hz), 2.83 (m, 2H), 1.72 (m, 2H), 1.56 (d, 3H), 1.33 (t, 3H, J=7.32 Hz), 1.33 (m , 1H), 1.23 (m, 2H), 0.97 (d, 3H, J=6.6 Hz).

Synthesis of Example 57

-1-{[2-pyrrolidin-1-yl-6-(trifluoromethyl)pyridin-3-yl]methyl}-3-{4-[(sulfamoylamino)methyl]phenyl}urea Step 1: N-Bromosuccinimide (1.51 g , 8.509 mmol) was added to a solution of 1-methyl-4-nitrobenzene (1.2 g, 7.735 mmol) in carbon tetrachloride. At room temperature 70% benzoyl peroxide (120 mg) was added to the mixture and refluxed for 24 h. The mixture was extracted with ethyl acetate, drying over magnesium sulfate, evaporation of the solvent and purification by column chromatography (silica gel: 100-200 mesh, eluent: ethyl acetate/n-hexane) 1-(bromomethyl)-4-nitrobenzene (1.1 g, 61%) in pure form.

Step 2: To a solution of 1-(bromomethyl)-4-nitrobenzene (1.1 g , 4.69 mmol) in dimethylformamide, potassium phthalimide (1.9 g, 10.314 mmol) was added. The mixture was reacted for overnight, extracted with ethyl acetate and washed by brine (3×20 mL). Drying over magnesium sulfate, evaporation of the solvent and purification by column chromatography (silica gel: 100-200 mesh, eluent: ethyl acetate/n-hexane) 2-(4-nitrobenzyl)isoindoline-1,3-dione (1.6 g, 99%).

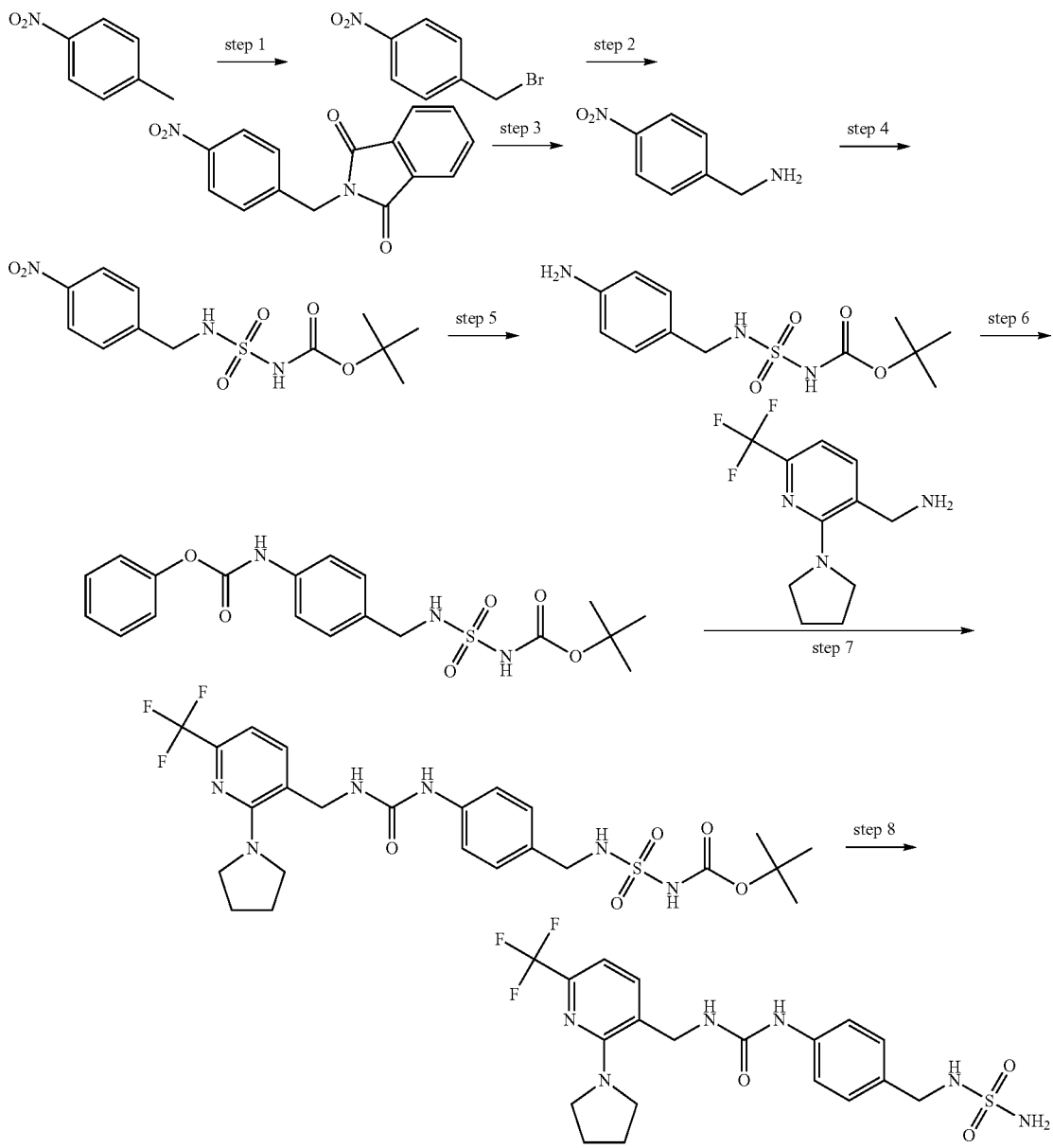

Step 3: To a stirred solution of 2-(4-nitrobenzyl)isoindoline-1,3-dione (1.6 g, 5.33 mmol) in tetrahydrofuran was added hydrazine monohydrate (4 equivalents). The mixture was stirred at reflux for 6 h, until complete consumption, as evidenced by TLC analysis, the mixture was cooled to room temperature. The mixture was treated with potassium bicarbonate to adjust the pH to 12~13. It was extracted with ethyl acetate, washed by brine, dried over magnesium sulfate and concentrated under reduced pressure. The residue was purified by column chromatography (silica gel: 100-200 mesh, eluent: ethyl acetate/n-hexane) to afford (4-nitrophenyl)methanamine (592 mg, 65%).

Step 4: Chlorosulfonyl isocyanate (0.063 mL) and tert-butanol (0.07 ml) was mixed in dichloromethane (5 mL). After 10 minutes, a solution of (4-nitrophenyl)methanamine (100 mg, 0.657 mmol) in dichloromethane was added and stirred for 30 minutes at 50° C. The mixture was allowred to cool to room temperature, triethylamine (0.11 mL) was added and the mixture was stirred for 3 h more. The reaction mixture was extracted with ethyl acetate, washed by brine and dried over magnesium sulfate. After evaporation of the ethyl acetate the crude compompound was purified by column chromatography (silica gel: 100-200 mesh, eluent: ethyl acetate/n-hexane) to gave tert-butyl N-(4-nitrobenzyl)sulfamoylcarbamate (112 mg, 51%).

Step 5: 10% Pd/C (7 mg) was added to a solution of tert-butyl N-(4-nitrobenzyl)sulfamoylcarbamate (65 mg) in ethanol and tetrahydrofuran. The mixture was charged with hydrogen gas balloon and stirred for 6 h at room temperature. The mixture was filtered using celite and evaporated in vacuo to gave tert-butyl N-(4-aminobenzyl)sulfamoyl-carbamate (58 mg, 98%).

Step 6: To a stirred solution of tert-butyl N-(4-aminobenzyl)sulfamoylcarbamate (86 mg, 0.285 mmol) in tetrahydrofuran—acetonitrile (1:1) was added pyridine (0.03 mL, 0.342 mmol) and phenylchloroformate (0.04 mL, 0.3 mmol) at 0° C. The mixture was stirred at 0° C. for 30 min and heated up to room temperature, then it was stirred for 30 min. The mixture was extracted with ethyl acetate, washed by brine, dried over magnesium sulfate and concentrated in vacuo. Purification by column chromatography (silica gel: 100-200 mesh, eluent: ethyl acetate/n-hexane) gave the tert-butyl N-(4-(3-((phenylcarbamate)methyl)-ureido)benzyl)sulfamoylcarbamate in pure form (59 mg, 49%).

Step 7: tert-Butyl N-(4-(3-((phenylcarbamate)methyl)ureido)benzyl)sulfamoylcarbamate (58 mg, 0.138 mmol) was dissolved in acetonitrile. (2-(Pyrrolidin-1-yl)-6-(trifluoromethyl)pyridin-3-yl)methanamine (38 mg, 0.138 mmol) and 4-dimethylaminopyridine (16 mg) were added to the solution. The reaction mixture was stirred for overnight at 50° C. The mixture was extracted with ethyl acetate and washed with brine. Drying over magnesium sulfate, evaporation of the ethyl acetate and purification by column chromatography gave tert-butyl N-(4-(3-((2-(pyrrolidin-1-yl)-6-(trifluoromethyl)pyridin-3-yl)methyl)ureido)-benzyl)sulfamoylcarbamate (50 mg, 60%).

Step 8: To a solution of tert-butyl N-(4-(3-((2-(pyrrolidin-1-yl)-6-(trifluoromethyl)pyridin-3-yl)methyl)ureido)benzyl)sulfamoylcarbamate (70 mg, 0.122 mmol) in dichloromethane (6 mL) trifluoroacetic acid (2 mL) was added at 0° C. The mixture was stirred for 30 min at 0° C. and for 2 h at room temperature. The mixture was neutralized by sodium bicarbonate to pH 7~8, extracted with ethyl acetate and washed with brine. Drying over magnesium sulfate, evaporation of the ethyl acetate and purification by column chromatography gave 1-{[2-pyrrolidin-1-yl-6-(trifluoromethyl)pyridin-3-yl]methyl}-3-{4-[(sulfamoylamino)methyl]-phenyl}urea (example 57) (50 mg, 86%).

$^1$H—NMR (400 MHz, CD$_3$OD): δ 7.81 (d, 1 H, Ar, J=7.52 Hz), 7.30 (dd, 4 H, Ar, J$_1$=8.44, J$_2$=8.44), 7.01 (d, 1 H, Ar, J=7.52 Hz), 4.48 (s, 2 H, CH$_2$NH), 4.12 (s, 2 H, CH$_2$NH), 3.58 (m, 4 H, pyrrole), 1.98 (m, 4 H, pyrrole)

Synthesis of Example 59

-1-{[2-(4-methylpiperidin-1-yl)-6-(trifluoromethyl)pyridin-3-yl]methyl}-3-{4-[(sulfamoylamino)methyl]phenyl}urea

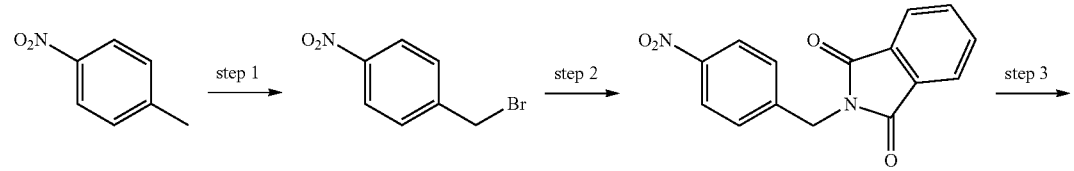

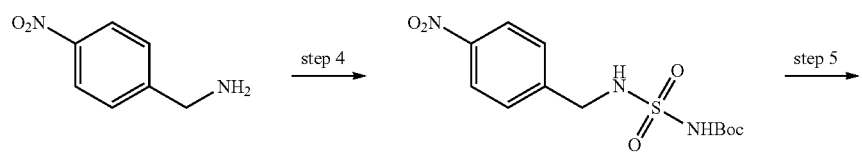

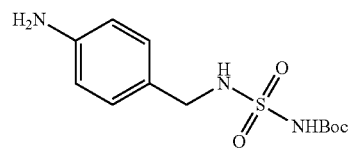
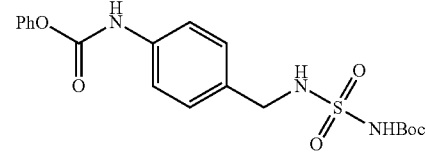
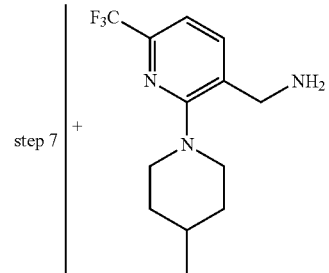
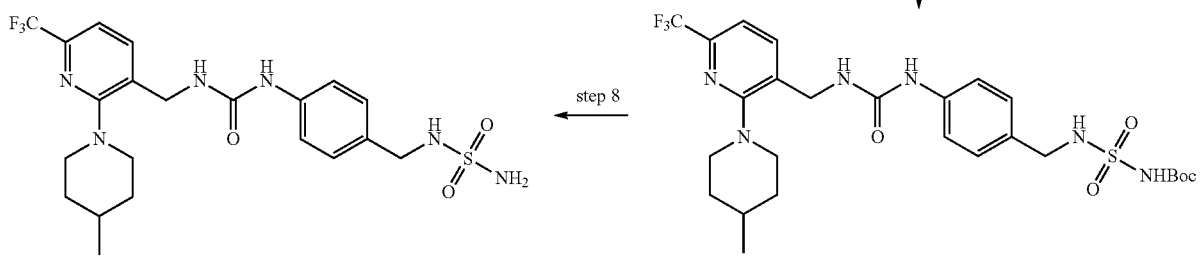

Step 1-6: according to example 57.

Step 7: tert-Butyl N-(4-(3-((phenylcarbamate)methyl)ureido)benzyl)sulfamoylcarbamate (58 mg, 0.138 mmol) was dissolved in acetonitrile, (2-(4-methylpiperidin-1-yl)-6-(trifluoromethyl)pyridin-3-yl)methanamine (38 mg, 0.138 mmol) and 4-dimethylaminopyridine (16 mg) were added to the solution. The reaction mixture was stirred for overnight at 50° C. The mixture was extracted with ethyl acetate, washed by brine and dried over magnesium sulfate. Evaporation of the ethyl acetate and purification by column chromatography (silica gel: 100-200 mesh, eluent: ethyl acetate/n-hexane) gave tert-butyl N-(4-(3-((2-(4-methylpiperidin-1-yl)-6-(trifluoromethyl)pyridin-3-yl)methyl)ureido)benzyl)sulfamoylcarbamate (50 mg, 60% yield).

Step 8: To a solution of tert-butyl N-(4-(3-((2-(4-methylpiperidin-1-yl)-6-(trifluoromethyl)pyridin-3-yl)methyl)ureido)benzyl)sulfamoylcarbamate (88 mg, 0.147 mmol) in dichloromethane (6 mL), tetrahydrofuran (2 mL) is added at 0° C. The mixture was stirred for 30 min at 0° C. and stirred for 2 h more at room temperature. After neutralisation by sodium bicarbonate to pH 7~8 the mixture was extracted with ethyl acetate and washed by brine. Drying over magnesium sulfate, evaporation of the ethyl acetate and purification by column chromatography (silica gel: 100-200 mesh, eluent: ethyl acetate/n-hexane) gave the N-(4-(3-((2-(4-methylpiperidin-1-yl)-6-(trifluoromethyl)pyridin-3-yl)methyl)ureido)benzyl)-aminosulfonamide (example 59) in pure form (58 mg, 78%).

$^1$H—NMR (CD$_3$OD) δ 7.81 (d, 1H, Ar, J=7.68 Hz), 7.34 (m, 5H, Ar) 4.44 (s, 2H, CH$_2$NH), 4.13 (s, 2H, CH$_2$NH), 3.46 (d, 2H, J=12.27 Hz), 2.87 (t, 2H), 1.76 (d, 2H, J=10.44 Hz), 1.44 (m, 1H), 1.30 (m, 2H), 1.01 (d, 3H, J=6.24 Hz).

Synthesis of Example 60

-1-{3-fluoro-4-[(sulfamoylamino)methyl]phenyl}-3-{[2-pyrrolidin-1-yl-6-(trifluoromethyl)pyridin-3-yl]methyl}urea

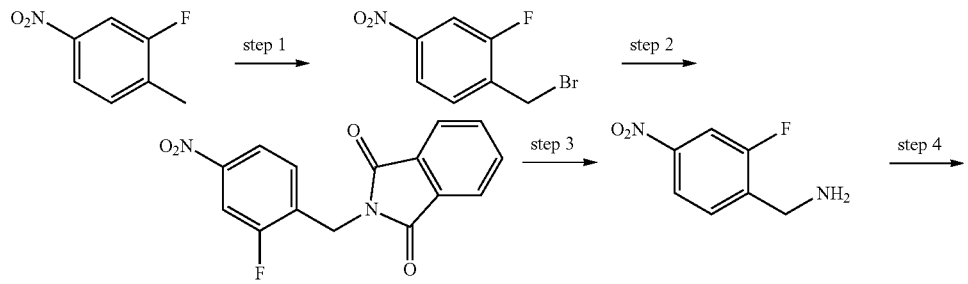

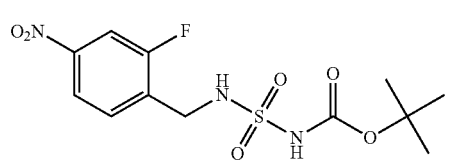
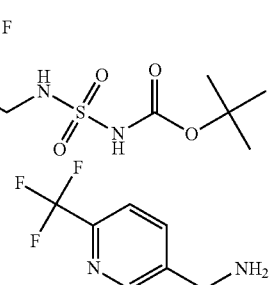
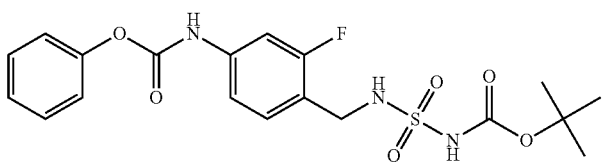
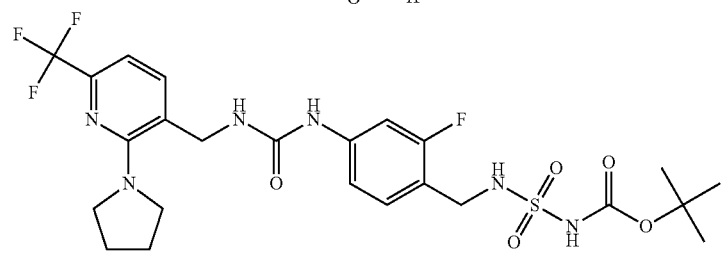
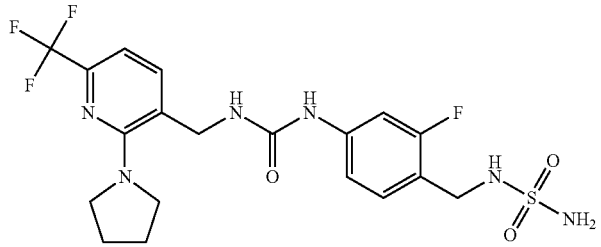

Step 1: N-Bromosuccinimide (1.27 g, 7.09 mmol) was added to a solution of 2-fluoro-1-methyl-4-nitrobenzene (1.0 g, 6.446 mmol) in carbon tetrachloride. At room temperature 70% benzoyl peroxide (150 mg) was added to the mixture and refluxed for 24 h. The mixture was extracted with ethyl acetate, drying over magnesium sulfate, evaporation of the solvent and purification by column chromatography (silica gel: 100-200 mesh, eluent: ethyl acetate/n-hexane) 1-(bromomethyl)-2-fluoro-4-nitrobenzene (1.05 g, 69%).

Step 2: To a solution of 1-(bromomethyl)-2-fluoro-4-nitrobenzene (1.05 g, 4.48 mmol) in dimethylformamide, potassium phthalimide (1.8 g, 9.852 mmol) was added. The mixture was reacted for overnight, extracted with ethyl acetate and washed by brine (3×20 mL). Drying over magnesium sulfate, evaporation of the solvent and purification by column chromatography (silica gel: 100-200 mesh, eluent: ethyl acetate/n-hexane) 2-(2-fluoro-4-nitrobenzyl)isoindoline-1,3-dione (1.35 g, 99%).

Step 3: To a stirred solution of 2-(2-fluoro-4-nitrobenzyl)isoindoline-1,3-dione (1.35 g, 4.48 mmol) in tetrahydrofuran was added hydrazine monohydrate (1.3 mL).The mixture was stirred at reflux for 6 h, until complete consumption, as evidenced by TLC analysis, the mixture was cooled to room temperature. The mixture was treated with potassium bicarbonate to adjust the pH to 12~13. It was extracted with ethyl acetate, washed by brine, dried over magnesium sulfate and concentrated under reduced pressure. The residue was purified by column chromatography (silica gel: 100-200 mesh, eluent: ethyl acetate/n-hexane) to afford (2-fluoro-4-nitrophenyl)methanamine (316 mg, 41%).

Step 4: Chlorosulfonyl isocyanate (0.1 mL) and tert-butanol (0.12 ml) was mixed in dichloromethane (5 mL). After 10 minutes, a solution of (2-fluoro-4-nitrophenyl)methanamine (200 mg, 1.176 mmol) in dichloromethane was added and stirred for 30 minutes at 50° C. The mixture was allowred to cool to room temperature, triethylamine (0.11 mL) was added and the mixture was stirred for 3 h more. The reaction mixture was extracted with ethyl acetate, washed by brine and dried over magnesium sulfate. After evaporation of the ethyl acetate the crude compompound was purified by column chromatography (silica gel: 100-200 mesh, eluent: ethyl acetate/n-hexane) to gave tert-butyl N-(2-fluoro-4-nitrobenzyl)sulfamoylcarbamate (139 mg, 34%).

Step 5: 10% Pd/C (42 mg) was added to a solution of tert-butyl N-(2-fluoro-4-nitrobenzyl)sulfamoylcarbamate (135 mg) in ethanol and tetrahydrofuran. The mixture was charged with hydrogen gas balloon and stirred for 6 h at room temperature. The mixture was filtered using celite and evaporated in vacuo to tert-butyl N-(4-amino-2-fluorobenzyl)sulfamoylcarbamate (127 mg, 99%).

Step 6: To a stirred solution of tert-butyl N-(4-amino-2-fluorobenzyl)sulfamoylcarbamate (127 mg, 0.398 mmol) in tetrahydrofuran—acetonitrile (1:1) was added pyridine (0.04 mL, 0.478 mmol) and phenylchloroformate (0.05 mL, 0.418 mmol) at 0° C. The mixture was stirred at 0° C. for 30 min and heated up to room temperature, then it was stirred for 30 min. The mixture was extracted with ethyl acetate, washed by brine, dried over magnesium sulfate and concentrated in vacuo. Purification by column chromatography (silica gel: 100-200 mesh, eluent: ethyl acetate/n-hexane) gave the tert-butyl N-(2-fluoro-4-(phenylcarbamate)methyl)ureido)benzyl)sulfamoylcarbamate in pure form (160 mg, 91%).

Step 7: Tert-butyl N-(2-fluoro-4-(phenylcarbamate)methyl)ureido)benzyl)sulfamoylcarbamate (60 mg, 0.137 mmol) was dissolved in acetonitrile. (2-(Pyrrolidin-1-yl)-6-(trifluoromethyl)pyridin-3-yl)methanamine (37 mg, 0.137 mmol) and 4-dimethylaminopyridine (17 mg) were added to the solution. The reaction mixture was stirred for overnight at 50° C. The mixture was extracted with ethyl acetate and washed with brine. Drying over magnesium sulfate, evaporation of the ethyl acetate and purification by column chromatography gave tert-butyl N-(2-fluoro-4-(3-((2-(pyrrolidin-1-yl)-6-(trifluoromethyl)pyridin-3-yl)methyl)ureido)benzyl)sulfamoylcarbamate (60 mg, 71%).

Step 8: To a solution of tert-butyl N-(2-fluoro-4-(3-((2-(pyrrolidin-1-yl)-6-(trifluoromethyl)pyridin-3-yl)methyl)ureido)benzyl)sulfamoylcarbamate (60 mg, 0.102 mmol) in dichloromethane (6 mL) was added trifluoroacetic acid (2 mL) at 0° C. The mixture was stirred for 30 min at 0° C. and for 2 h at room temperature. The mixture was neutralized by sodium bicarbonate to pH 7~8, extracted with ethyl acetate and washed with brine. Drying over magnesium sulfate, evaporation of the ethyl acetate and purification by column chromatography gave 1-{3-fluoro-4-[(sulfamoylamino)methyl]phenyl}-3-{[2-pyrrolidin-1-yl-6-(trifluoromethyl)pyridin-3-yl]methyl}urea (example 60) (35 mg, 73%).

$^1$H—NMR (300 MHz, acetone-d6): δ 8.31 (s, 1 H, NH), 7.74 (d, 1 H, Ar, J=7.5 Hz), 7.56 (dd, 1H, Ar, $J_1$=13.02 Hz, $J_2$=2.01 Hz), 7.35 (t, 1H, Ar, J=8.4 Hz), 7.05 (m, 2 H, Ar), 6.29 (m, 1 H, NH), 5.95 (m, 2 H, NH), 4.54 (d, 2 H, J=5.31 Hz), 4.22 (d, 2 H, J=5.67 Hz), 3.60 (m, 4 H, pyrrole), 1.95 (m, 4 H, pyrrole).

Synthesis of Example 61

-1-{3-fluoro-4-[(sulfamoylamino)methyl]phenyl}-3-{[2-(4-methylpiperidin-1-yl)]-6-(trifluoromethyl)pyridin-3-yl]methyl}urea

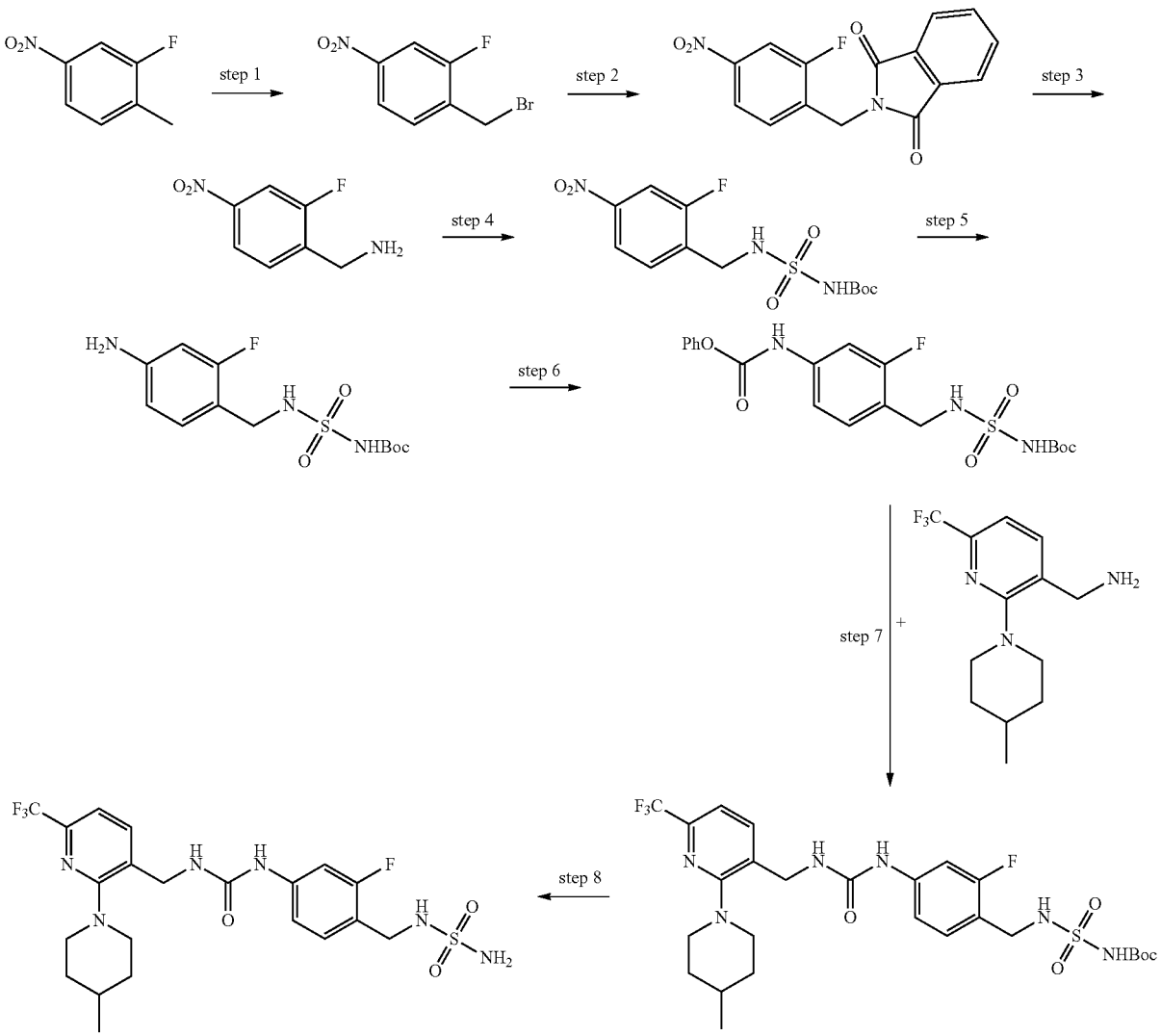

Step 1-6: according to example 60.

Step 7: Tert-butyl N-(2-fluoro-4-(phenylcarbamate)methyl) ureido)benzyl)sulfamoyl carbamate (60 mg, 0.137 mmol) was dissolved in acetonitrile, (2-(4-methylpiperidin-1-yl)-6-(trifluoromethyl)pyridin-3-yl)methanamine (37 mg, 0.137 mmol) and 4-dimethylaminopyridine (17 mg) were added to the solution. The reaction mixture was stirred for overnight at 50° C. The mixture was extracted with ethyl acetate, washed by brine and dried over magnesium sulfate. Evaporation of the ethyl acetate and purification by column chromatography (silica gel: 100-200 mesh, eluent: ethyl acetate/n-hexane) gave tert-butyl N-(2-fluoro-4-(3-((2-(4-methylpiperidin-1-yl)-6-(trifluoromethyl)pyridin-3-yl)methyl)ureido)benzyl)sulfamoylcarbamate (60 mg, 71% yield).

Step 8: To a solution of tert-butyl N-(2-fluoro-4-(3-((2-(4-methylpiperidin-1-yl)-6-(trifluoromethyl)pyridin-3-yl)methyl)ureido)benzyl)sulfamoylcarbamate (60 mg, 0.097 mmol) in dichloromethane (6 mL), tetrahydrofuran (2 mL) is added at 0° C. The mixture was stirred for 30 min at 0° C. and stirred for 2 h more at room temperature. After neutralisation by sodium bicarbonate to pH 7~8 the mixture was extracted with ethyl acetate and washed by brine. Drying over magnesium sulfate, evaporation of the ethyl acetate and purification by column chromatography (silica gel: 100-200 mesh, eluent: ethyl acetate/n-hexane) gave the N-(2-fluoro-4-(3-((2-(4-methylpiperidin-1-yl)-6-(trifluoromethyl)pyridin-3-yl)methyl)ureido)benzyl)aminosulfonamide (example 61) in pure form (35 mg, 70%).

$^1$H—NMR (CD$_3$OD) δ 7.79 (d, 1H, Ar, J=7.14 Hz), 7.38 (m, 3H, Ar), 7.03 (dd, 1H, Ar,), 4.44 (s, 2H), 4.10 (s, 2H), 3.30 (m, 2H), 2.90 (t, 2H), 1.77 (m, 2H), 1.58 (m, 1H), 1.45 (m, 2H), 1.00 (d, 3H, J=6.6 Hz).

Synthesis of Example 63

-2-(3-fluoro-4-((N-methylmethylsulfonamido)methyl)phenyl)-N-((2-(4-methylpiperidin-1-yl)-6-(trifluoromethyl)pyridin-3-yl)methyl)propanamide

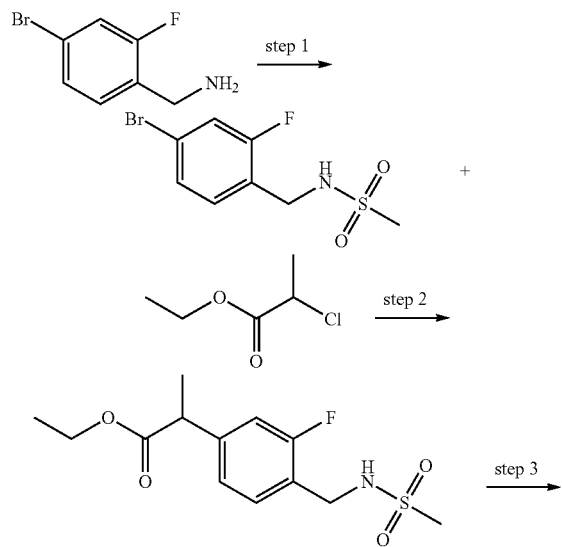

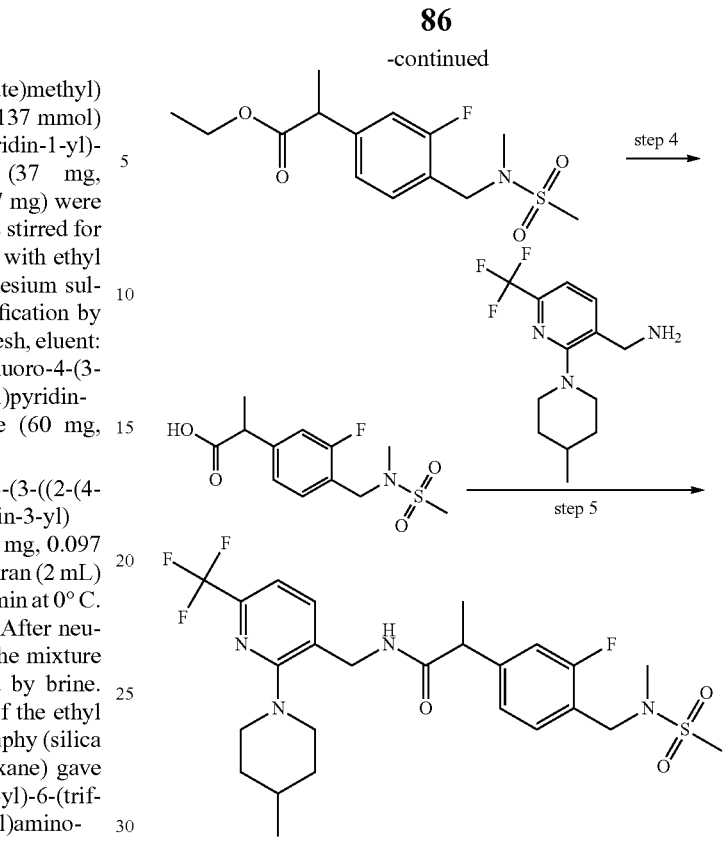

Step 1: (4-Bromo-2-fluorophenyl)methanamineis stirred in pyridine and methanesulfonyl chloride (1.9 equiv.) is dropwise at 0° C. After remove in ice bath, reaction mixture is stirred at room-temperature during 1 h. The reaction is quenched with 1 N HCl and extracted with ethyl acetate. Extracted organic layer is dried over by magnesium sulfate. Reaction mixture is purified by column chromatography and obtained N-(4-bromo-2-fluorobenzyl)methanesulfonamide.

Step 2: N-(4-bromo-2-fluorobenzyl)methanesulfonamide is dissolved in anhydrous dimethylformamide and charged with N$_2$. Ethyl-2-chloro propionate (1.3 equiv.) is dropped to the reactant and manganese (2 equiv.), nickel-2,2'-bipyridine (0.1 equiv.) is added with trifluoroacetic acid (0.026 equiv.). The reaction is refluxed overnight. The reaction mixture is warmed to ambient temperature. The reaction is quenched with 1 N HCl and organic layer is extracted with diethyl ether. The extracted organic layer is dried over magnesium sulfate, and concentrated into ethyl 2-(3-fluoro-4-(methylsulfonamidomethyl)phenyl)propanoate that is carried onto the next step without purification.

Step 3: Crude ethyl 2-(3-fluoro-4-(methylsulfonamidomethyl)phenyl)propanoate is stirred in acetone at 0° C., add K$_2$CO$_3$ (1.5 equiv.). After that, methyliodide (3 equiv.) is drop-wised and the reaction mixture is refluxed. After 15 h, the reaction mixture is quenched with water and extracted with ethyl acetate. The organic layer is dried over magnesium sulfate and concentrated. Reaction mixture was purified by column chromatography and obtained ethyl 2-(3-fluoro-4-((N-methylmethylsulfonamido)methyl)phenyl) propanoate.

Step 4: A solution of ethyl 2-(3-fluoro-4-((N-methylmethylsulfonamido)methyl)phenyl)propanoate in tetrahydrofuran and water (1:1) was added NaOH (2.5 equiv.) and stirred at room temperature. After 15 h, the reaction mixture was acidified by acetic acid until pH=2–3. The acid is extracted with dichloromethane and water. The organic layer was washed with water, dried over magnesium sulfate and concentrated in vacuo. The product was purified column chromatography and 2-(3-fluoro-4-((N-methylmethylsulfonamido)methyl)phenyl)propanoic acid product.

Step 5: A solution of 2-(3-fluoro-4-((N-methylmethylsulfonamido)methyl)phenyl)propanoic acid in 1,4-dioxane was added N-(3-dimethylaminopropyl)-N'-ethylcarbodiimide (1.5 equiv), 1-hydroxybenzotriazole (1.5 equiv), and (2-(4-methylpiperidin-1-yl)-6-(trifluoromethyl)pyridin-3-yl)methanamine (1 equiv) were added and dropped triethylamine (2.5 equiv). The reaction mixture was stirred overnight at room temperature. Added water to the reaction mixture and extracted with ethyl acetate. The extracted organic layer was dried over magnesium sulfate. Evaporation of the solvent followed by column chromatographic purification (ethyl acetate:hexane) afforded 2-(3-fluoro-4-((N-methylmethylsulfonamido) methyl)phenyl)-N-((2-(4-methylpiperidin-1-yl)-6-(trifluoromethyl)pyridin-3-yl) methyl)propanamide (example 63).

1H NMR (300 MHz, CDCl$_3$) δ 7.44 (q, 2H, J=7.50 Hz, Ar—H), 7.19 (d, 1H, J=6.00 Hz, Ar—H), 7.02-7.11 (m, 2H, Ar—H), 6.23 (bs, 1H, Ar—NH), 4.46 (d, 2H, J=6.00 Hz, piperidine-α-H), 4.36 (s, 2H, Ar-α-H), 3.58 (q, 1H, J=7.50 Hz, Ar-α-H), 3.28 (m, 2H, piperidine-H), 2.86 (s, 3H, methansulfonyl-CH$_3$), 2.77 (s, 3H, Ar—N—CH$_3$), 1.71 (m, 2H, piperidine-H), 1.54 (m, 7H, piperidine-4H and Ar-α-CH$_3$), 0.97 (d, 3H, J=6.00 Hz, piperidine-CH$_3$).

Synthesis of Example 64

-2-(3-fluoro-4-((sulfamoylamino)methyl)phenyl)-N-((2-(4-methylpiperidin-1-yl)-6-(trifluoromethyl)pyridin-3-yl)methyl)propanamide

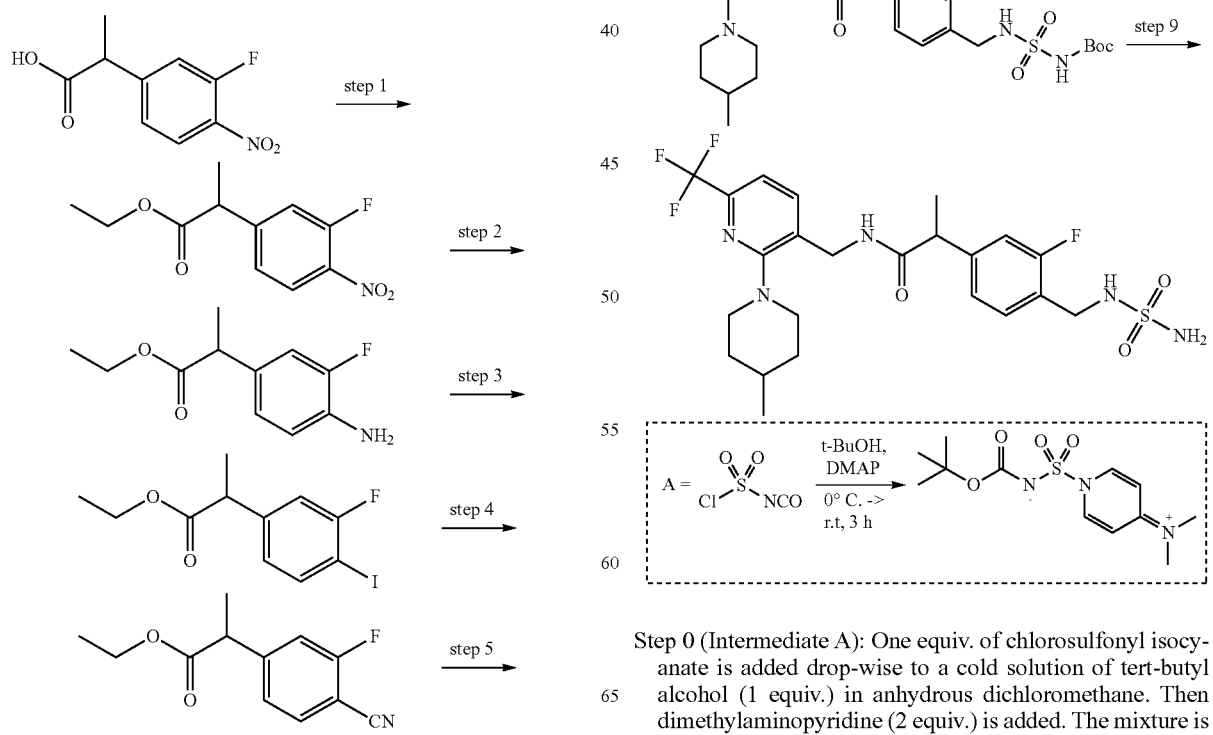

Step 0 (Intermediate A): One equiv. of chlorosulfonyl isocyanate is added drop-wise to a cold solution of tert-butyl alcohol (1 equiv.) in anhydrous dichloromethane. Then dimethylaminopyridine (2 equiv.) is added. The mixture is stirred for 3 h at room temperature. The organic layer is extracted with dichloromethane and washed with water. After column chromatography, colorless powder is obtained.

Step 1: Sulfuric acid (0.3 mL) was added to a solution of 2-(3-fluoro-4-nitro-phenyl)-propionic acid in ethanol. The mixture was refluxed. After 6 h, the mixture was basified by aqueous sodium bicarbonate and extracted with ethyl acetate (ethyl acetate). Drying over magnesium sulfate and evaporation of the ethyl acetate and purified by column chromatography (ethyl acetate:hexane) gave the ethyl 2-(3-fluoro-4-nitrophenyl)propanoate in pure form Step 2: 10% Palladium on carbon was added to a solution ethyl 2-(3-fluoro-4-nitrophenyl)propanoate in ethanol and tetrahydrofuran and the mixture was charged with $H_2$ (g). After stirring the reaction mixture for 6 h, the mixture was filtered using celite and purified by column chromatography give ethyl 2-(4-amino-3-fluorophenyl)propanoate.

Step 3: A solution of p-TsOH $H_2O$ (3 equiv.) in acetonitrile was added to a solution of ethyl 2-(4-amino-3-fluorophenyl)propanoate (1 equiv) in acetonitrile. The resulting suspension of amine salt was cooled to 10-15° C. and to this was added, gradually, a solution of $NaNO_2$ (2 equiv.) and potassoim iodide (2.5 equiv.) in water. The reaction mixture was stirred for 10 min then allowed to come to 20° C. and stirred until the starting material was consumed. After 4 h, water, $NaHCO_3$ (until pH=9-10) was added and extracted with ethyl acetate. The organic layer was washed with water, dried over magnesium sulfate and concentrated in vacuo. The residue was purified on a silica gel column using ethyl acetate-hexane as solvent system to give ethyl 2-(3-fluoro-4-iodophenyl)propanoate.

Step 4: Ethyl 2-(3-fluoro-4-iodophenyl)propanoate, $Pd_2(dba)_3$, dppf, cinc powder and cinc cyanide were placed in round flask charged with $N_2$ and DMA (0.02 equiv.) was dropped by syringe. The reaction mixture was stirred at 120° C. for 15 h and cooled to room temperature. Extracted with ethyl acetate and washed with 2 N $NH_4OH$ solution. The organic layer was washed with water, dried over sodium sulfate and concentrated in vacuo. The residue was purified on a silica gel column using ethyl acetate -hexane as solvent system to give ethyl 2-(4-cyano-3-fluorophenyl)propanoate.

Step 5: A solution of ethyl 2-(4-cyano-3-fluorophenyl)propanoate in tetrahydrofuran and water (1:1) is added NaOH (2.5 equiv.) and stirred at room temperature. After 15 h, the reaction mixture is acidified by acetic acid until pH=2-3. The acid is extracted with dichloromethane and water. The organic layer is washed with water, dried over magnesium sulfate and concentrated in vacuo. The product is purified column chromatography (dichloromethane: methanol=10:1) and gained 2-(4-cyano-3-fluorophenyl)propanoic acid.

Step 6: N-(3-dimethylaminopropyl)-N'-ethylcarbodiimide (1.5 equiv), 1-hydroxybenzotriazole (1.5 equiv), and (2-(4-methylpiperidin-1-yl)-6-(trifluoromethyl)pyridin-3-yl) methanamine (1 equiv) are added to a solution of the 2-(4-cyano-3-fluorophenyl)propanoic aciddrop-wise triethylamine (2.5 equiv). The reaction mixture is stirred overnight at room temperature. The reaction is quenched with water and extracted with ethyl acetate. The extracted organic layer is dried over magnesium sulfate. After evaporate solvent, purified by column chromatographic purification (ethyl acetate:hexane) afforded 2-(4-cyano-3-fluorophenyl)-N-((2-(4-methylpiperidin-1-yl)-6-(trifluoromethyl)pyridin-3-yl)methyl)propanamide.

Step 7: Nickel(II) chloride hexahydride (1 equiv.) and 2-(4-cyano-3-fluorophenyl)-N-((2-(4-methylpiperidin-1-yl)-6-(trifluoromethyl)pyridin-3-yl)methyl)propanamide are stirred in anhydrous ethanol during 15 min for activation. Sodium borohydride (7 equiv.) is added on it and react for 2 h. Adding celite to the reaction and filter it using celite packed filter, washing with ethanol. The reaction mixture is purified after concentration to give 2-(4-(aminomethyl)-3-fluorophenyl)-N-((2-(4-methyl piperidi n-1-yl)-6-(trifluoromethyl)pyridin-3-yl)methyl)propanamide.

Step 8: 2-(4-(Aminomethyl)-3-fluorophenyl)-N-((2-(4-methylpiperidin-1-yl)-6-(trifluoromethyl)pyridin-3-yl)methyl)propanamide and intermediate (A) are dissolved in dichloromethane, drop-wise triethylamine (0.1 equiv.). The reaction is stirred for 15 h at room temperature and quenched with water. The organic layer is extracted by dichloromethane and concentrated. After purification, tert-butyl N-(2-fluoro-4-(1-((2-(4-methylpiperidin-1-yl)-6-(trifluoromethyl)pyridin-3-yl)methylamino)-1-oxopropan-2-yl)benzyl)sulfamoylcarbamate is obtained.

Step 9: Trifluoroacetic acid (12 mL) is added to tert-butyl N-(2-fluoro-4-(1-((2-(4-methylpiperidin-1-yl)-6-(trifluoromethyl)pyridin-3-yl)methylamino)-1-oxopropan-2-yl) benzypsulfamoylcarbamate solutions in dichloromethane and the reaction is stirred for 4 h at room temperature. Water is dropped to the mixture and organic compound is extracted with dichloromethane. The mixture is purified after concentration and 2-(3-fluoro-4-((sulfamoylamino)methyl)phenyl)-N-((2-(4-methyl piperidin-1-yl)-6-(trifluoromethyl)pyridin-3-yl)methyl)propanamide (example 64) was obtained.

$^1$H NMR (400 MHz, CDCl3) δ 7.45(d, 1H, J=8.00 Hz, Ar—H), 7.33(t, 1H, J=8.00, Ar—H), 7.18(d, 1H, J=8.00, Ar—H), 7.03(m, 2H, Ar—H), 6.21(bs, 1H, α-NH), 4.43 (bs, 1H, Ar-α-NH), 4.46 (m, 2H, Ar-α-CH$_2$), 4.41 (d, 2H, J=4.00 Hz, α-CH$_2$), 4.32 (d, 2H, J=8.00, α-CH$_2$), 3.47 (m, 1H), 2.38 (s, 3H, Ar—CH$_3$), 1.44 (bt, 3H, α-CH$_3$), 1.20-1.26(m, 5H), 0.96 (d, 3H, J=4.00 Hz).

Synthesis of Example 65

—N-(2-fluoro-5-(3-((2-(4-methylpiperidin-1-yl)-6-(trifluoromethyl)pyridin-3-yl)methyl)ureido)benzyl) methanesulfonamide

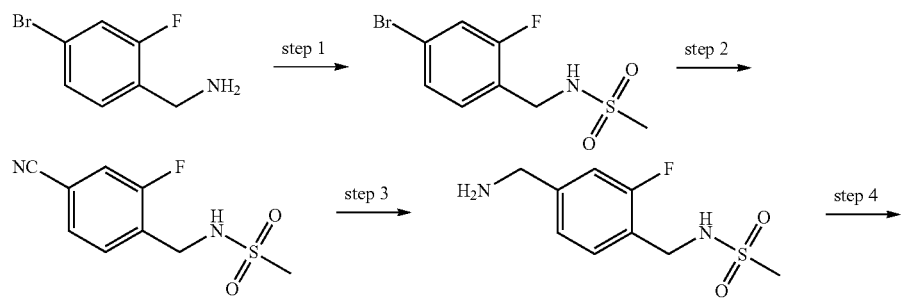

-continued

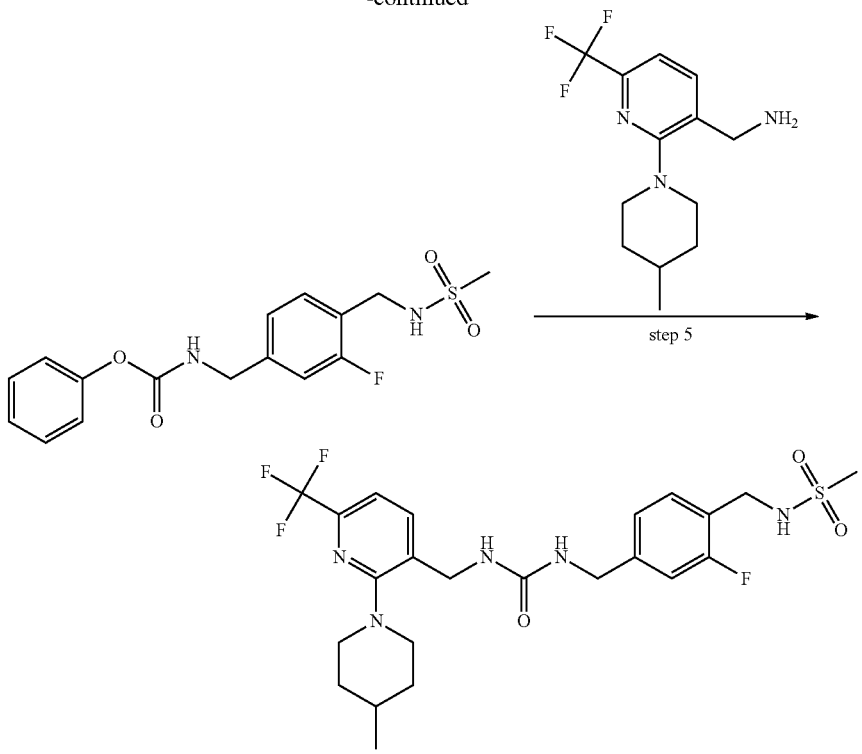

Step 1: To a stirred solution of (4-bromo-2-fluorophenyl)methanamine in pyridine was added methane sulfonylchloride. The reaction mixture was stirred for overnight at room temperature. The reaction was stopped adding 1 N HCl and organic compound was extracted with ethyl acetate. The organic layer was dried over magnesium sulfate and filtered. The crude was purified by column chromatography to obtain N-(4-bromo-2-fluorobenzyl)methanesulfonamide.

Step 2: N-(4-bromo-2-fluorobenzyl)methanesulfonamide, $Pd_2(dba)_3$, dppf, cinc powder and cinc cyanide were placed in round flask charged with $N_2$ and DMA (0.02 equiv.) was dropped by syringe. The reaction mixture was stirred at 120° C. in sealed tube for 15 h. The reaction was cooled down until room temperature and extracted with ethyl acetate and washed with 2N $NH_4OH$ solution. The organic layer was washed with water, dried and concentrated in vacuo. The residue was purified on a silica gel column using ethyl acetate-hexane as solvent system to give N-(4-cyano-2-fluorobenzyl)methanesulfonamide.

Step 3: 10% Palladium on carbon was added to N-(4-cyano-2-fluorobenzyl)methanesulfonamide solution in methanol and the mixture was charged with $H_2$ (g). After stirring the reaction mixture for 15 h, the mixture was filtered using Celite and purified by column chromatography to give N-(4-(aminomethyl)-2-fluorobenzyl)methanesulfonamide.

Step 4: To a stirred solution of N-(4-(aminomethyl)-2-fluorobenzyl)methanesulfonamide in acetone/tetrahydrofuran was added pyridine at 0° C. The reaction mixture was stirred for 3 h at room temperature. The residue was dissolved in ethyl acetate and washed with water and brine. The organic layer was dried over magnesium sulfate and filtered. The filtrate removed in vacuo. The crude was purified by column chromatography and phenyl 3-fluoro-4-(methylsulfonamidomethyl)benzylcarbamate was obtained.

Step 5: To a stirred solution of phenyl 3-fluoro-4-(methylsulfonamidomethyl)benzylcarbamate in acetonitrile was added (2-(4-methylpiperidin-1-yl)-6-(trifluoromethyl)pyridin-3-yl)methanamine, followed by dimethylaminopyridine (1 equiv.). The reaction mixture was stirred for 15 h at 50° C. The residue was dissolved in dichloromethane and washed with water and brine. The organic layer was dried over magnesium sulfate and filtered. The filtrate removed in vacuo. After column chromatography, N-(2-fluoro-4-((3-((2-(4-methylpiperidin-1-yl)-6-(trifluoromethyl)pyridin-3-yl)methyl)ureido)methyl)benzyl)-methanesulfonamide (example 65) was obtained.

$^1H$ NMR (400 MHz, $CDCl_3$) δ 7.45(d, 1H, J=8.00 Hz, Ar—H), 7.33 (t, 1H, J=8.00, Ar—H), 7.18 (d, 1H, J=8.00, Ar—H), 7.03 (m, 2H, Ar—H), 5.40 (bs, 1H, α-NH), 4.67 (bs, 1H, Ar-α-NH), 4.46 (m, 2H, Ar-α-$CH_2$), 4.35 (d, 4H, J=4.00 Hz, α-$CH_2$), 3.24 (d, 2H, J=8.00), 2.79-2.93 (m, 5H), 1.25-1.68 (m, 5H), 0.96 (d, 3H, J=4.00 Hz).

Synthesis of Example 66

-2-(4-fluoro-3-(methylsulfonamidomethyl)phenyl)-N-((2-(4-methylpiperidin-1-yl)-6-(trifluoromethyl)pyridin-3-yl)methyl)propanamide

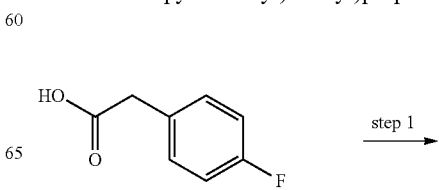

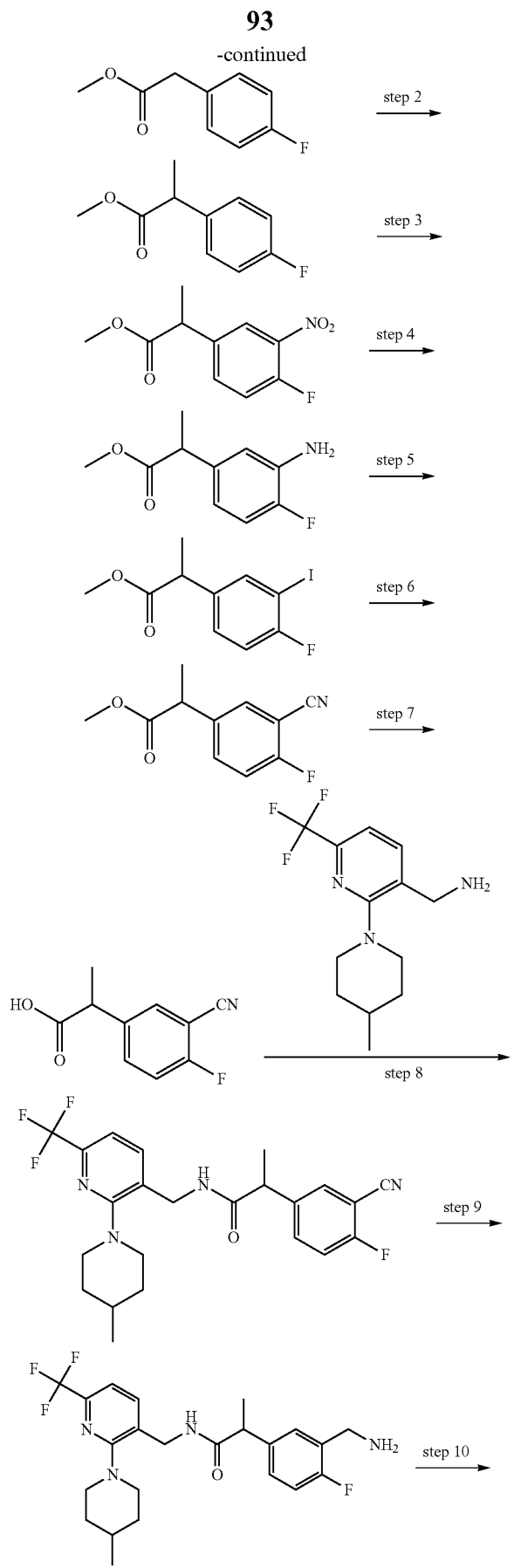

Step 1: To the solution 2-(4-fluorophenyl)acetic acid (700 mg, 43.4 mmol) in methanol was slowly added sulfuric acid (0.42 mL, 4.34 mmol,0.1 eq) at room temperature. The reaction mixture was refluxed for 3 h at 70° C. under $N_2$ TLC showed complete consumption of starting material. The reaction mixture was cooled to room temperature. Solvent was removed in vacuo and extracted with ethyl acetate. The organic part was washed with brine. The organic layer was dried over magnesium sulfate and concentrated under reduced pressure to afford crude product which was purified by column chromatography to methyl 2-(4-fluorophenyl)acetate (660 mg, 84%).

Step 2: To the cooled solution of sodium hydride (501 mg, 2.285 mmol, 60% suspension in oil) in anhydrous tetrahydrofuran was added solution of methyl 2-(4-fluorophenyl) acetate (990 mg, 2.285 mmol) dropwise at 0° C. Reaction mixture was stirred at room temperature for 1 h. TLC showed complete consumption of starting material. The reaction mixture was quenched with brine and extracted with ethyl acetate. The organic part was washed with brine. The organic layer was dried over magnesium sulfate and concentrated under reduced pressure to afford crude product which was purified by column chromatography to methyl 2-(4-fluorophenyl)propanoate (551 mg, 52%)

Step 3: To a solution of methyl 2-(4-fluorophenyl)propanoate (200 mg, 19.5 mmol) in 14 mL of sulfuric acid at 0° C. was added 69% $HNO_3$ (0.4 mL) dropwise over 5 min. After stirring for 35 min at 0° C., the solution was diluted with ethyl acetate at 0° C., and then the resultant solution was poured into cold water. Water layer was extracted with ethyl acetate. The combined organic layer was washed with water, brine then dried over sodium sulfate. After removing solvent in vacuo, the residue was purified by silica gel column chromatography to give methyl 2-(4-fluoro-3-nitrophenyl)propanoate (175 mg, 79%)

Step 4: Starting material methyl 2-(4-fluoro-3-nitrophenyl) propanoate (1.55 g, 1.23 mmol) was dissolved in methanol. 20% w/w Pd/C (10 wt %) was added to it. The resulting mixture was stirred at room temperature for 2 h under $H_2$ gas. TLC showed complete consumption of starting material. The mixture was filtered by celite bed and then the filterate was concentrated under reduced pressure to afford methyl 2-(3-amino-4-fluorophenyl)propanoate (1.25 g, 88%)

Step 5: To a solution of p-TsOH.$H_2O$ (0.680 g, 3.4 mmol) in acetonitrile (12 mL) was added the methyl 2-(3-amino-4-fluorophenyl)propanoate (3 mmol). The resulting suspension of amine salt was cooled to 10-15° C. and to this was added, gradually, a solution of $NaNO_2$ (0.476 g, 6.9 mmol) and potassoim iodide (1.432 g, 8.6 mmol) in water (1.8 mL). The reaction mixture was stirred for 10 min then allowed to come to 20° C. and stirred for 16 h reaction mixture was then added water (50 mL), $NaHCO_3$ (1 M;

until pH=9-10) and Na$_2$S$_2$O$_3$ (2 M, 6 mL). The precipitated aromatic iodide was filtered or extracted with ethyl acetate and purified by flash chromatography to get methyl 2-(4-fluoro-3-iodophenyl)propanoate (0.711 g, 68%).

Step 6: A mixture of methyl 2-(4-fluoro-3-iodophenyl)propanoate (530 mg, 1.72 mmol), cuprous cyanide (309 mg, 3.45 mmol) and dimethylformamide (5 mL) was heated at 140° C. for 7 h. After the reaction was completed the mixture was cooled to room temperature, poured into water (100 mL), and stirred at room temperature for 0.5 h. and extracted with ethyl acetate (3×50 mL). The combined organic layers were washed with water and brine, dried over magnesium sulfate, and concentrated in vacuo which offered methyl 2-(3-cyano-4-fluorophenyl)propanoate (256 mg, 71%)

Step 7: A solution of methyl 2-(3-cyano-4-fluorophenyl)propanoate (250 mg, 1.2 mmol) in water and tetrahydrofuran (1:2, 30 mL) was treated with lithium hydroxide (3.0 mmol) at 0° C. and stirred for 2 h at room temperature. The mixture was diluted with water and dichloromethane, acidified with 1 N HCl solution, and extracted with dichloromethane several times. The combined organic layers were washed with water and brine, dried over magnesium sulfate, and concentrated in vacuo which offered 2-(3-cyano-4-fluorophenyl)propanoic acid (210 mg, 88%)

Step 8: A solution of 2-(3-cyano-4-fluorophenyl)propanoic acid (50 mg, 0.256 mmol) in 1,4 Dioxane was cooled in an ice bath and N-(3-dimethylaminopropyl)-N'-ethylcarbodiimide (73 mg, 0.384 mmol), 1-hydroxybenzotriazole (51 mg, 0.384 mmol), Triethylamine (72 μl, 0.760 mmol) and the (2-(4-methylpiperidin-1-yl)-6-(trifluoromethyl)pyridin-3-yl)methanamine (70 mg, 0.256 mmol), were added consecutively. The reaction mixture was stirred overnight at room temperature. Water was added to the reaction mixture and extracted with dichloromethane. The combined organic extracts were washed successively with saturated NaHCO$_3$ solution, 0.5 N HCl and then water and dried over magnesium sulfate. Evaporation of the solvent followed by column chromatographic purification afforded 2-(3-cyano-4-fluorophenyl)-N-((2-(4-methylpiperidin-1-yl)-6-(trifluoromethyl)pyridin-3-yl)methyl)propanamide (73 mg, 58%)

Step 9: To a stirred solution of 2-(3-cyano-4-fluorophenyl)-N-((2-(4-methylpiperidin-1-yl)-6-(trifluoromethyl)pyridin-3-yl)methyl)propanamide (70 mg, 0.156 mmol) in dry ethanol (15 mL), cooled to 0° C., were added NiCl$_2$.6 H$_2$O (37 mg, 0.156 mmol). Sodium borohydride (36 mg, 0.936 mmol) was then added in small portions over 10 min. The reaction was exothermic and effervescent. The reaction mixture was allowed to warm to room temperature and left to stir for a further 1 h.The purple residue was dissolved in ethyl acetate (50 mL) and extracted with saturated NaHCO$_3$. The organic layer was dried over magnesium sulfate and the solvent removed in vacuo to yield 2-(3-(aminomethyl)-4-fluorophenyl)-N-((2-(4-methylpiperidin-1-yl)-6-(trifluoromethyl)pyridin-3-yl)methyl)propanamide (40 mg, 35%).

Step 10: A cooled solution of 2 2-(3-(aminomethyl)-4-fluorophenyl)-N-((2-(4-methylpiperidin-1-yl)-6-(trifluoromethyl)pyridin-3-yl)methyl)propanamide (34 mg, 0.075 mmol) in dichloromethane was added triethylamine (25 μL, 0.189 mmol) at 0° C. resulting solution was treated dropwise with methanesulfonyl chloride (7.4 μL, 0.091 mmol) over 10 min and stirred for 1 h at room temperature. After aqueous workup, the residue was purified by flash column chromatography to obtain 2-(4-fluoro-3-(methylsulfonamidomethyl)phenyl)-N-((2-(4-methylpiperidin-1-yl)-6-(trifluoromethyl)pyridin-3-yl)methyl)propanamide (example 66) (31 mg, 80%).

$^1$H NMR (300 MHz, CD$_3$OD) δ 7.50-7.45 (m, 2H, Ar—H), 7.34-7.28 (m, 1H, Ar—H), 7.24-7.21 (d, 1H, J=9.0, Ar—H), 7.10-7.07 (d, 1H, J=9.0, Ar—H), 7.06-7.03 (d, 1H, J=9.0, Ar—H), 4.38-4.33 (d, 2H, J=9.0), 4.29 (s, 2H, CH$_2$NHMs) 3.76-3.69 (q, 1 H, CH—CH$_3$), 3.39-3.35 (m, 2H), 2.86 (s, 3H, NHSO$_2$CH$_3$), 2.82-2.74 (m, 3H), 1.72-1.68 (m, 2H), 1.48-1.46 (d, 3H), 1.27-1.37 (m, 3H), 0.99-0.96 (d, 3H, J=9.0).

Exemplary compounds 67 and 68 can be prepared in a similar manner as example 64.

Exemplary compounds 69-72 can be obtained by chiral resolution of examples 67 and 68. These resolutions can be e.g. performed by chiral high performance liquid chromatography (HPLC) on a Chiralpak AD-H, 5 μM, 250×20 mm. Products can be detected by a JASCO UV-1575 wavelength UV monitor. As mobile phase can be used a mixture of n-hexane/ethanol (7:3, v/v) with a flow rate 19 mL/min at 25° C.

Mass spectrometric data are cited hereinafter by way of example for the following exemplary compounds (Table 1):

TABLE 1

| Exemplary compound | [M + H] |
| --- | --- |
| 1 | 512.0 |
| 2 | 484.5 |
| 3 | 484.5 |
| 4 | 472.1 |
| 5 | 500.0 |
| 6 | 513.1 |
| 8 | 477.1 |
| 9 | 505.2 |
| 14 | 519.1 |
| 17 | 503.2 |
| 21 | 517.2 |
| 24 | 518.1 |
| 25 | 517.1 |
| 28 | 519.1 |
| 29 | 530.0 |
| 30 | 531.2 |
| 34 | 636.4 |
| 35 | 519.4 |
| 45 | 519.3 |
| 46 | 547.5 |
| 47 | 516.1 |
| 48 | 515.1 |
| 49 | 530.0 |
| 50 | 542.2 |
| 51 | 498.0 |
| 52 | 486.1 |
| 53 | 514.0 |
| 54 | 517.1 |
| 55 | 544.3 |
| 56 | 486.2 |
| 57 | 472.9 |
| 58 | 513.8 |
| 59 | 500.9 |
| 60 | 491.0 |
| 61 | 519.1 |
| 63 | 545.2 |
| 64 | 532.0 |
| 65 | 532.0 |
| 66 | 531.0 |

Pharmacological Methods

I. Functional Testing Carried Out on the Vanilloid Receptor 1 (VR1/TRPV1 Receptor)

The agonistic or antagonistic effect of the substances to be tested on the rat-species vanilloid receptor 1 (VR1/TRPV1) can be determined using the following assay. In this assay, the influx of Ca$^{2+}$ through the receptor channel is quantified with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:

Complete medium: 50 mL HAMS F12 nutrient mixture (Gibco Invitrogen GmbH, Karlsruhe, Germany) with 10% by volume of FCS (foetal calf serum, Gibco Invitrogen GmbH, Karlsruhe, Germany, heat-inactivated); 2 mM L-glutamine (Sigma, Munich, Germany); 1% by weight of AA solution (antibiotic/antimyotic solution, PAA, Pasching, Austria) and 25 ng/mL NGF medium (2.5 S, Gibco Invitrogen GmbH, Karlsruhe, Germany)

Cell culture plate: Poly-D-lysine-coated, black 96-well plates having a clear base (96-well black/clear plate, BD Biosciences, Heidelberg, Germany) are additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 μg/mL. Aliquots having a laminin concentration of 100 μg/mL are removed and stored at −20° C. The aliquots are diluted with PBS in a ratio of 1:10 to 10 μg/mL of laminin and respectively 50 μL of the solution are pipetted into a recess in the cell culture plate. The cell culture plates are incubated for at least two hours at 37° C., the excess solution is removed by suction and the recesses are each washed twice with PBS. The coated cell culture plates are stored with excess PBS which is not removed until just before the feeding of the cells.

Preparation of the Cells:

The vertebral column is removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (percent by volume) of an AA solution (antibiotic/antimyotic solution, PAA, Pasching, Austria). The vertebral column is cut longitudinally and removed together with fasciae from the vertebral canal. Subsequently, the dorsal root ganglia (DRG) are removed and again stored in cold HBSS buffer mixed with 1% by volume of an AA solution. The DRG, from which all blood remnants and spinal nerves have been removed, are transferred in each case to 500 μL of cold type 2 collagenase (PAA, Pasching, Austria) and incubated for 35 minutes at 37° C. After the addition of 2.5% by volume of trypsin (PAA, Pasching, Austria), incubation is continued for 10 minutes at 37° C. After complete incubation, the enzyme solution is carefully pipetted off and 500 μL of complete medium are added to each of the remaining DRG. The DRG are respectively suspended several times, drawn through cannulae No. 1, No. 12 and No. 16 using a syringe and transferred to a 50 mL Falcon tube which is filled up to 15 mL with complete medium. The contents of each Falcon tube are respectively filtered through a 70 μm Falcon filter element and centrifuged for 10 minutes at 1,200 rpm and room temperature. The resulting pellet is respectively taken up in 250 μL of complete medium and the cell count is determined.

The number of cells in the suspension is set to $3 \times 10^5$ per mL and 150 μL of this suspension are in each case introduced into a recess in the cell culture plates coated as described hereinbefore. In the incubator the plates are left for two to three days at 37° C., 5% by volume of $CO_2$ and 95% relative humidity. Subsequently, the cells are loaded with 2 μM of Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at room temperature used for $Ca^{2+}$ measurement in a FLIPR assay. The $Ca^{2+}$-dependent fluorescence is in this case measured before and after the addition of substances (λex=488 nm, λem=540 nm). Quantification is carried out by measuring the highest fluorescence intensity (FC, fluorescence counts) over time.

FLIPR Assay:

The FLIPR protocol consists of 2 substance additions. First the compounds to be tested (10 μM) are pipetted onto the cells and the $Ca^{2+}$ influx is compared with the control (capsaicin 10 μM). This provides the result in % activation based on the $Ca^{2+}$ signal after the addition of 10 μM of capsaicin (CP). After 5 minutes' incubation, 100 nM of capsaicin are applied and the $Ca^{2+}$ influx is also determined.

Desensitising agonists and antagonists lead to suppression of the $Ca^{2+}$ influx. The % inhibition is calculated compared to the maximum achievable inhibition with 10 μM of capsazepine.

Triple analyses (n=3) are carried out and repeated in at least 3 independent experiments (N=4).

Starting from the percentage displacement caused by different concentrations of the compounds to be tested of general formula I, $IC_{50}$ inhibitory concentrations which cause a 50-percent displacement of capsaicin were calculated. $K_i$ values for the test substances were obtained by conversion by means of the Cheng-Prusoff equation (Cheng, Prusoff; Biochem. Pharmacol. 22, 3099-3108, 1973).

Pharmacological Data

The affinity of the compounds according to the invention for the vanilloid receptor 1 (VR1/TRPV1 receptor) was determined as described hereinbefore (pharmacological method I).

The compounds according to the invention display outstanding affinity to the VR1/TRPV1 receptor (Table 2).

In Table 2 the abbreviations below have the following meanings:

Cap=capsaicin

AG=agonist

The value after the "@" symbol indicates the concentration at which the inhibition (as a percentage) was respectively determined.

TABLE 2

| Compound according to Example | (f) $K_i$ (human being) [nM] Cap |
|---|---|
| 1 | 102 |
| 2 | 48%@5 μM |
| 3 | 20 |
| 4 | 26 |
| 5 | 4 |
| 6 | 11 |
| 8 | 71%@5 μM |
| 9 | 95 |
| 14 | 46%@5 μM |
| 17 | 23 |
| 21 | 5 |
| 24 | 5 |
| 25 | 4 |
| 28 | 5 |
| 29 | 5 |
| 30 | 8 |
| 34 | 61 |
| 35 | 53%@5 μM |
| 45 | 80 |
| 46 | 5 |
| 47 | 6 |
| 48 | 87 |
| 49 | 12 |

TABLE 2-continued

| Compound according to Example | (f) $K_i$ (human being) [nM] Cap |
|---|---|
| 50 | AG |
| 51 | 50 |
| 52 | 46 |
| 53 | 5 |
| 54 | 76 |
| 55 | 4 |
| 56 | 38 |
| 57 | 85 |
| 58 | 2 |
| 59 | 1 |
| 60 | 20 |
| 61 | 1 |
| 63 | 55 |
| 64 | 4 |
| 65 | 12%@5 µM |
| 66 | 58%@5 µM |

The invention claimed is:

1. A substituted compound of general formula (I),

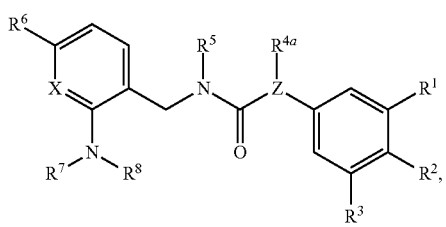

wherein
one of residues $R^1$ and $R^2$ denotes $CH_2-N(R^9)-S(=O)_2-R^{10}$,
wherein $R^9$ represents H, $CH_3$ or $C_2H_5$, and
wherein $R^{10}$ represents $NH_2$, $CH_3$ or $C_2H_5$,
and the respective remaining residue of $R^1$ and $R^2$ is selected from the group consisting of H, F, Cl, Br, I, $CH_3$, $CH_2-OH$, $CH_2-CH_2-OH$, $CH_2-O-CH_3$, $CH_2-CH_2-O-CH_3$, $CF_3$, OH, $O-CH_3$, $O-CH_2-OH$, $O-CH_2-O-CH_3$, $O-C_2H_5$, $O-CH_2-CH_2-OH$, $O-CH_2-CH_2-O-CH_3$ and $NH_2$,
$R^3$ is selected from the group consisting of H, F, Cl, Br, I, $CH_3$, $CF_3$, OH, $O-CH_3$, $O-CF_3$, and $NH_2$,
Z represents N or $C-R^{4b}$,
wherein $R^{4b}$ represents H or $CH_3$,
$R^{4a}$ represents H or $CH_3$,
$R^5$ represents H or $CH_3$,
X represents N or CH;
$R^6$ represents $CF_3$, an unsubstituted, saturated $C_{1-4}$ aliphatic residue or an unsubstituted, saturated $C_{3-6}$ cycloaliphatic residue,
$R^7$ represents H, or an unsubstituted $C_{1-4}$ aliphatic residue,
$R^8$ represents a $C_{1-4}$ aliphatic residue, unsubstituted or mono-, di- or trisubstituted with 1, 2 or 3 substituents selected independently of one another from the group consisting of F, Cl, Br, I, OH, $O-CH_3$, $O-CH_2-OH$, $O-CH_2-O-CH_3$, $O-C_2H_5$, $O-CH_2-CH_2-OH$, $O-CH_2-CH_2-O-CH_3$, $NH_2$, $NH(CH_3)$, and $N(CH_3)_2$;
a $C_{3-6}$ cycloaliphatic residue, optionally bridged via an unsubstituted, saturated $C_{1-4}$ aliphatic group, unsubstituted or mono-, or di-, or trisubstituted with 1, 2 or 3 substituents selected independently of one another from the group consisting of F, Cl, Br, I, $CH_3$, $C_2H_5$, $CH_2-OH$, $CH_2-CH_2-OH$, $CH_2-O-CH_3$, $CH_2-CH_2-O-CH_3$, $CH_2-NH(CH_3)$, $CH_2-N(CH_3)_2$, $CF_3$, OH, $O-CH_3$, $O-CH_2-OH$, $O-CH_2-O-CH_3$, $O-C_2H_5$, $O-CH_2-CH_2-OH$, $O-CH_2-CH_2-O-CH_3$, $NH_2$, $NH(CH_3)$, and $N(CH_3)_2$; aryl or heteroaryl, in each case optionally bridged via an unsubstituted, saturated $C_{1-4}$ aliphatic group, and in each case unsubstituted or mono-, or di- or trisubstituted with 1, 2 or 3 substituents selected independently of one another from the group consisting of F, Cl, Br, I, $CH_3$, $C_2H_5$, $CH_2-OH$, $CH_2-CH_2-OH$, $CH_2-O-CH_3$, $CH_2-CH_2-O-CH_3$, $CF_3$, OH, $O-CH_3$, $O-CH_2-OH$, $O-CH_2-O-CH_3$, $O-C_2H_5$, $O-CH_2-CH_2-OH$, $O-CH_2-CH_2-O-CH_3$, $O-CF_3$, $S-CF_3$, $NH_2$, $NH(CH_3)$, and $N(CH_3)_2$;

or $R^7$ and $R^8$ together with the nitrogen atom connecting them form a 3 to 6 membered heterocycloaliphatic residue, unsubstituted or mono-, or di- or trisubstituted with 1, 2 or 3 substituents selected independently of one another from the group consisting of F, Cl, Br, I, $CH_3$, $C_2H_5$, $CH_2-OH$, $CH_2-CH_2-OH$, $CH_2-O-CH_3$, $CH_2-CH_2-O-CH_3$, $CH_2-NH(CH_3)$, $CH_2-N(CH_3)_2$, $CF_3$, OH, $O-CH_3$, $O-CH_2-OH$, $O-CH_2-O-CH_3$, $O-C_2H_5$, $O-CH_2-CH_2-OH$, $O-CH_2-CH_2-O-CH_3$, $O-CF_3$, SH, $S-CH_3$, $S-CF_3$, $NH_2$, $NH(CH_3)$, $N(CH_3)_2$, phenyl, $C(=O)$-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$, wherein said 3 to 6 membered heterocycloaliphatic residue can optionally be condensed with a further ring selected from the group consisting of phenyl, pyridyl, a $C_{3-6}$ cycloaliphatic residue and a 3 to 6 membered heterocycloaliphatic residue, wherein said furthr ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl, in which an "aliphatic group" and an "aliphatic residue" can in each case, independently of one another, be branched or unbranched, saturated or unsaturated, if not indicated otherwise;

in which a "cycloaliphatic residue" and a "heterocycloaliphatic residue" can in each case, independently of one another, be saturated or unsaturated, if not indicated otherwise;

optionally in the form of a single stereoisomer or a mixture of stereoisomers, in the form of the free compound and/or a physiologically acceptable salt thereof.

2. The substituted compound according to claim 1, wherein one of residues $R^1$ and $R^2$ denotes $CH_2-N(R^9)-S(=O)_2-R^{10}$,
wherein $R^9$ represents H, $CH_3$, or $C_2H_5$, and
wherein $R^{10}$ represents $NH_2$, $CH_3$, or $C_2H_5$,
and the respective remaining residue of $R^1$ and $R^2$ is selected from the group consisting of H, F, Cl, Br, I, $CH_3$, $CH_2-OH$, $CH_2-O-CH_3$, $CF_3$, OH, and $O-CH_3$.

3. The substituted compound according to claim 1, wherein $R^2$ denotes $CH_2-N(R^9)-S(=O)_2-R^{10}$,
wherein $R^9$ represents H, $CH_3$, or $C_2H_5$, and
wherein $R^{10}$ represents $NH_2$, $CH_3$, or $C_2H_5$, and R¹ is selected from the group consisting of H, F, Cl, Br, I, $CH_3$, $CH_2$—OH, $CH_2$—O—$CH_3$, $CF_3$, OH, and O—$CH_3$.

4. The substituted compound according to claim 1, wherein $R^3$ is selected from the group consisting of H, F, Cl, $CH_3$, $CF_3$, OH and O—$CH_3$.

5. The substituted compound according to claim 1, wherein Z represents N and
$R^{4a}$ represents H, or Z represents C—$R^{4b}$,
wherein $R^{4b}$ represents H or $CH_3$, and
$R^{4a}$ represents H.

6. The substituted compound according to claim 1, wherein $R^5$ represents H.

7. The substituted compound according to claim 1, wherein X represents N.

8. The substituted compound according to claim 1, wherein $R^6$ represents $CF_3$, tert.-Butyl or cyclopropyl.

9. The substituted compound according to claim 1, wherein
$R^7$ represents H or an unsubstituted, saturated, $C_{1-4}$ aliphatic residue,
$R^8$ represents a $C_{1-4}$ aliphatic residue, unsubstituted or mono- or disubstituted with 1, 2 or 3 substituents selected independently of one another from the group consisting of F, Cl, OH, and O—$CH_3$;
a $C_{3-6}$ cycloaliphatic residue, unsubstituted or mono-, or di-, or trisubstituted with 1, 2 or 3 substituents selected independently of one another from the group consisting of F, Cl, Br, I, $CH_3$, $C_2H_5$, $CF_3$, OH, O—$CH_3$, $NH_2$, $NH(CH_3)$, and $N(CH_3)_2$;
phenyl or pyridyl, in each case unsubstituted or mono-, or di- or trisubstituted with 1, 2 or 3 substituents selected independently of one another from the group consisting of F, Cl, Br, I, $CH_3$, $C_2H_5$, $CF_3$, OH, O—$CH_3$, O—$CF_3$, S—$CF_3$, $NH_2$, $NH(CH_3)$, and $N(CH_3)_2$;

or $R^7$ and $R^8$ together with the nitrogen atom connecting them form a 3 to 6 membered heterocycloaliphatic residue, unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—$CH_2$—OH, $CH_2$—O—$CH_3$, $CH_2$—$CH_2$—O—$CH_3$, $CH_2$—$NH(CH_3)$, $CH_2$—$N(CH_3)_2$, $CF_3$, OH, O—$CH_3$, O—$CH_2$—OH, O—$CH_2$—O—$CH_3$, O—$C_2H_5$, O—$CH_2$—$CH_2$—OH, O—$CH_2$—$CH_2$—O—$CH_3$, O—$CF_3$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$,
wherein said 3 to 6 membered heterocycloaliphatic residue can optionally be condensed with a further ring selected from the group consisting of phenyl, heteroaryl, a $C_{3-6}$ cycloaliphatic residue and a 3 to 6 membered heterocycloaliphatic residue, wherein said ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl.

10. The substituted compound according to claim 1, wherein
$R^7$ represents H, $CH_3$, $C_2H_5$, n-propyl, iso-propyl, n-butyl or tert.-butyl, $R^8$ represents $CH_3$, $C_2H_5$, n-propyl, iso-propyl, n-butyl, tert.-butyl, cyclopropyl, cyclobutyl, cyclopentyl, cyclohexyl, or phenyl, wherein phenyl can be unsubstituted or mono-, or di- or trisubstituted with 1, 2 or 3 substituents selected independently of one another from the group consisting of F, Cl, Br, I, $CH_3$, $CF_3$, OH, O—$CH_3$, and O—$CF_3$;

or $R^7$ and $R^8$ together with the nitrogen atom connecting them form a 3 to 6 membered heterocycloaliphatic residue selected from the group consisting of azetidinyl, pyrrolidinyl, piperidinyl, piperazinyl and morpholinyl, in each case independently of one another unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—O—$CH_3$, $CH_2$—$NH(CH_3)$, $CH_2$—$N(CH_3)_2$, $CF_3$, OH, O—$CH_3$, O—$CH_2$—O—$CH_3$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$,
wherein said 3 to 6 membered heterocycloaliphatic residue can optionally be condensed with a further ring selected from the group consisting of a $C_{3-6}$ cycloaliphatic residue and a 3 to 6 membered heterocycloaliphatic residue, wherein said ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl.

11. The substituted compound according to claim 1, wherein
one of residues $R^1$ and $R^2$ denotes $CH_2$—$N(R^9)$—S(=O)$_2$—$R^{10}$,
wherein $R^8$ represents H, $CH_3$, or $C_2H_5$, and
wherein $R^{10}$ represents $NH_2$, $CH_3$, or $C_2H_5$,
and the respective remaining residue of $R^1$ and $R^2$ is selected from the group consisting of H, F, Cl, Br, I, $CH_3$, $CH_2$—OH, $CH_2$—O—$CH_3$, $CF_3$, OH, and O—$CH_3$,
$R^3$ is selected from the group consisting of H, F, Cl, $CH_3$, and O—$CH_3$,
Z represents N and
$R^{4a}$ represents H, or Z represents C—$R^{4b}$,
wherein $R^{4b}$ represents H or $CH_3$, and
$R^{4a}$ represents H,
$R^5$ represents H,
X represents N or CH,
$R^6$ represents $CF_3$, tert.-Butyl or cyclopropyl,
$R^7$ represents H, $CH_3$, $C_2H_5$, n-propyl, iso-propyl, n-butyl or tert.-butyl,
$R^8$ represents $CH_3$, $C_2H_5$, n-propyl, iso-propyl, n-butyl, tert.-butyl, cyclopropyl, cyclobutyl, cyclopentyl, cyclohexyl, or phenyl, wherein phenyl can be unsubstituted or mono-, or di- or trisubstituted with 1, 2 or 3 substituents selected independently of one another from the group consisting of F, Cl, Br, I, $CH_3$, $CF_3$, OH, O—$CH_3$, and O—$CF_3$;

or $R^7$ and $R^8$ together with the nitrogen atom connecting them form a 3 to 6 membered heterocycloaliphatic residue selected from the group consisting of azetidinyl, pyrrolidinyl, piperidinyl, piperazinyl and morpholinyl, in each case independently of one another unsubstituted or mono-, or di- or trisubstituted with 1, 2 or 3 substituents selected independently of one another from the group consisting of F, Cl, Br, I, $CH_3$, $C_2H_5$, $CH_2$—OH, $CH_2$—O—$CH_3$, $CH_2$—$NH(CH_3)$, $CH_2$—$N(CH_3)_2$, $CF_3$, OH, O—$CH_3$, O—$CH_2$—O—$CH_3$, $NH_2$, $NH(CH_3)$, $N(CH_3)_2$, phenyl, C(=O)-phenyl, benzyl and pyridyl, wherein phenyl, benzyl and pyridyl can in each case independently of one another be unsubstituted or mono-, or di- or trisubstituted with 1, 2 or 3 substituents selected independently of one another from the group consisting of F, Cl, Br, I, $CH_3$, tert.-butyl, $CF_3$ and $OCH_3$, wherein said 3 to 6 membered heterocycloaliphatic residue can optionally be condensed with a further ring selected from the group consisting of a $C_{3-6}$ cycloaliphatic residue and a 3 to 6 membered heterocycloaliphatic residue, wherein said ring can be unsubstituted or mono-, or di- or trisubstituted with 1, 2 or 3 substituents selected independently of one another from the group consisting of F, Cl, Br, I, $CH_3$, tert.-butyl, $CF_3$, $OCH_3$ and an unsubstituted phenyl.

12. The substituted compound according to claim 1 selected from the group consisting of 1 N-((2-(4-methylpiperidin-1-yl)-6-(trifluoromethyl)pyridin-3-yl)methyl)-2-(3-(methylsulfonamidomethyl)phenyl)propanamide;

2 2-(3-(methylsulfonamidomethyl)phenyl)-N-((2-(pyrrolidin-1-yl)-6-(trifluoromethyl)pyridin-3-yl)methyl)propanamide;

3 2-(4-(methylsulfonamidomethyl)phenyl)-N-((2-(pyrrolidin-1-yl)-6-(trifluoromethyl)pyridin-3-yl)methyl)propanamide;

4 N-(4-(3-((2-(pyrrolidin-1-yl)-6-(trifluoromethyl)pyridin-3-yl)methyl)ureido)benzy)methanesulfonamide;

5 N-(4-(3-((2-(4-methyl piperidin-1-yl)-6-(trifluoromethyl)pyridin-3-yl)methyl)ureido)benzyly)methanesulfonamide;

6 N-((2-(4-methylpiperidin-1-yl)-6-(trifluoromethyl)pyridin-3-yl)methyl)-2-(4-(methylsulfonamidomethyl)phenyl)propanamide;

7 N-((2-(dimethylamino)-6-(trifluoromethyl)pyridin-3-yl)methyl)-2-(3-fluoro-4-(methylsulfonamidomethyl)phenyl)propanamide;

8 N-((2-(ethylamino)-6-(trifluoromethyl)pyridin-3-yl)methyl)-2-(3-fluoro-4-(methylsulfonamidomethyl)phenyl)propanamide;

9 N-((2-(butylamino)-6-(trifluoromethyl)pyridin-3-yl)methyl)-2-(3-fluoro-4-(methylsulfonamidomethyl)phenyl)propanamide;

10 N-((2-(cyclohexylamino)-6-(trifluoromethyl)pyridin-3-yl)methyl)-2-(3-fluoro-4-(methylsulfonamidomethyl)phenyl)propanamide;

11 2-(3-fluoro-4-(methylsulfonamidomethyl)phenyl)-N-((2-(4-fluorophenylamino)-6-(trifluoromethyl)pyridin-3-yl)methyl)propanamide;

12 N-((2-(butyl(methyl)amino)-6-(trifluoromethyl)pyridin-3-yl)methyl)-2-(3-fluoro-4-(methylsulfonamidomethyl)phenyl)propanamide;

13 N-((2-(3,3-difluoroazetidin-1-yl)-6-trifluoromethyl)pyridin-3-yl)methyl)-2-(3-fluoro-4-(methylsulfonamidomethyl)phenyl)propanamide;

14 2-(3-fluoro-4-(methylsulfonamidomethyl)phenyl)-N-((2-(3-methoxyazetidin-1-yl)-6-(trifluoromethyl)pyridin-3-yl)methyl)propanamide;

15 N-(2-fluoro-4-(3-((2-(pyrrolidin-1-yl)-6-(trifluoromethyl)pyridin-3-yl)methyl)ureido)benzyl)methanesulfonamide;

16 2-(3-fluoro-4-(methylsulfonamidomethyl)phenyl)-N-((2-(pyrrolidin-1-yl)-6-(trifluoromethyl)pyridin-3-yl)methyl)acetamide;

17 2-(3-fluoro-4-(methylsulfonamidomethyl)phenyl)-N-((2-(pyrrolidin-1-yl)-6-(trifluoromethyl)pyridin-3-yl)methyl)propanamide;

18 2-(3-fluoro-4-(methylsulfonamidomethyl)phenyl)-N-((2-(2-methylpyrrolidin-1-yl)-6-(trifluoromethyl)pyridin-3-yl)methyl)propanamide;

19 N-((2-((S)-3-(dimethylarnino)pyrrolidin-1-yl)-6-(trifluoromethyl)pyridin-3-yl)methyl)-2-(3-fluoro-4-(methylsulfonamidomethyl)phenyl)propanamide;

20 N-((2-((R)-3-(dimethylamino)pyrrolidin-1-yl)-6-(trifluoromethyl)pyridin-3-yl)methyl)-2-(3-fluoro-4-(methylsulfonamidomethyl)phenyl)propanamide;

21 2-(3-fluoro-4-(methylsulfonamidomethyl)phenyl)-N-((2-(piperidin-1-yl)-6-(trifluoromethyl)pyridin-3-yl)methyl)propanamide;

22 2-(3-fluoro-4-(methylsulfonamidomethyl)phenyl)-N-((2-(4-fluoropiperidin-1-yl)-6-(trifluoromethyl)pyridin-3-yl)methyl)propanamide;

23 2-(3-fluoro-4-(methylsulfonamidomethyl)phenyl)-N-((2-(4-methoxypiperidin-1-yl)-6-(trifluoromethyl)pyridin-3-yl)methyl)propanamide;

24 N-(2-fluoro-4-(3-((2-(4-methylpiperidin-1-yl)-6-(trifluoromethyl)pyridin-3-yl)methyl)ureido)benzyl)methanesulfonamide;

25 2-(3-fluoro-4-(methylsulfonamidomethyl)phenyl)-N-((2-(4-methylpiperidin-1-yl)-6-(trifluoromethyl)pyridin-3-yl)methyl)acetamide;

26 N-((6-cyclopropyl-2-(4-methylpiperidin-1-yl)pyridin-3-yl)methyl)-2-(3-fluoro-4-(methylsulfonamidomethyl)phenyl)propanamide;

27 N-(4-tert-butyl-2-(4-methylpiperidin-1-yl)benzyl)-2-(3-fluoro-4-(methylsulfonamidomethyl)phenyl)propanamide;

28 N-((6-tert-butyl-2-(4-methylpiperidin-1-yl)pyridin-3-yl)methyl)-2-(3-fluoro-4-(methylsulfonamidomethyl)phenyl)propanamide;

29 2-(3-fluoro-4-(methylsulfonamidomethyl)phenyl)-N-(2-(4-methylpiperidin-1-yl)-4-(trifluoromethyl)benzyl)propanamide;

30 2-(3-fluoro-4-(methylsulfonamidomethyl)phenyl)-N-((2-(4-methylpiperidin-1-yl)-6-(trifluoromethyl)pyridin-3-yl)methyl)propanamide;

31 2-(3-fluoro-4-(methylsulfonamidomethyl)phenyl)-N-((2-(4-(methoxymethyl)piperidin-1-yl)-6-(trifluoromethyl)pyridin-3-yl)methyl)propanamide;

32 2-(3-fluoro-4-(methylsulfonamidomethyl)phenyl)-N-((2-(4-phenylpiperidin-1-yl)-6-(trifluoromethyl)pyridin-3-yl)methyl)propanamide;

33 N-((2-(4-benzylpiperidin-1-yl)-6-(trifluoromethyl)pyridin-3-yl)methyl)-2-(3-fluoro-4-(methylsulfonamidomethyl)phenyl)propanamide;

34 N-((2-(4-(di methylamino)-4-phenyl piperidin-1-yl)-6-(trifluoromethyl)pyridin-3-yl)methyl)-2-(3-fluoro-4-(methylsulfonamidomethyl)phenyl)propanamide;

35 2-(3-fluoro-4-(methylsulfonamidomethyl)phenyl)-N-((2-morpholino-6-(trifluoromethyl)pyridin-3-yl)methyl)propanamide;

36 N-((2-((2S,6R)-2,6-dimethylmorpholino)-6-(trifluoromethyl)pyridin-3-yl)methyl)-2-(3-fluoro-4-(methylsulfonamidomethyl)phenyl)propanamide;

37 2-(3-fluoro-4-(methylsulfonamidomethyl)phenyl)-N-((2-(4-methylpiperazin-1-yl)-6-(trifluoromethyl)pyridin-3-yl)methyl)propanamide;

38 2-(3-fluoro-4-(methylsulfonamidomethyl)phenyl)-N-((2-(4-phenylpiperazin-1-yl)-6-(trifluoromethyl)pyridin-3-yl)methyl)propanamide;

39 2-(3-fluoro-4-(methylsulfonamidomethyl)phenyl)-N-((2-(4-(pyridin-2-yl)piperazin-1-yl)-6-(trifluoromethyl)pyridin-3-yl)methyl)propanamide;

40 N-((2-(4-((dimethylamino)methyl)piperidin-1-yl)-6-(trifluoromethyl)pyridin-3-yl)methyl)-2-(3-fluoro-4-(methylsulfonamidomethyl)phenyl)propanamide;

41 2-(3-fluoro-4-(methylsulfonamidomethyl)phenyl)-N-((2-(4-(4-fluorobenzoyl)piperidin-1-yl)-6-(trifluoromethyl)pyridin-3-yl)methyl)propanamide;

42 N-((2-(3-tert-butyl-1-oxa-2,8-diazaspiro[4.5]dec-2-en-8-yl)-6-(trifluoromethyl)pyridin-3-yl)methyl)-2-(3-fluoro-4-(methylsulfonamidomethyl)phenyl)propanamide;

43 2-(3-fluoro-4-(methylsulfonamidomethyl)phenyl)-N-((2-(3-phenyl-1-oxa-2,8-diazaspiro[4.5]dec-2-en-8-yl)-6-(trifluoromethyl)pyridin-3-yl)methyl)propanamide;

44 N-(2,6-difluoro-4-(3-((2-(4-methylpiperidin-1-yl)-6-(trifluoromethyl)pyridin-3-yl)methyl)ureido)benzyl)methanesulfonamide;

45 2-(3-chloro-4-(methylsulfonamidomethyl)phenyl)-N-((2-(pyrrolidin-1-yl)-6-(trifluoromethyl)pyridin-3-yl)methyl)propanamide;

46 2-(3-chloro-4-(methylsulfonamidomethyl)phenyl)-N-((2-(4-methylpiperidin-1-yl)-6-(trifluoromethyl)pyridin-3-yl)methyl)propanamide;

47 N-(2-hydroxy-4-(3-((2-(4-methylpiperidin-1-yl)-6-(trifluoromethyl)pyridin-3-yl)methyl)ureido)benzyl)methanesulfonamide;

48 2-(3-methoxy-4-(methylsulfonamidomethyl)phenyl)-N-((2-(pyrrolidin-1-yl)-6-(trifluoromethyl)pyridin-3-yl)methyl)propanamide;

49 N-(2-methoxy-4-(3-((2-(4-methylpiperidin-1-yl)-6-(trifluoromethyl)pyridin-3-yl)methyl)ureido)benzyl)methanesulfonamide;

50 2-(3-methoxy-4-(methylsulfonamidomethyl)phenyl)-N-((2-(4-methylpiperidin-1-yl)-6-(trifluoromethyl)pyridin-3-yl)methyl)propanamide;

51 2-(3-methyl-4-(methylsulfonamidomethyl)phenyl)-N-((2-(pyrrolidin-1-yl)-6-(trifluoromethyl)pyridin-3-yl)methyl)propanamide;

52 N-(2-methyl-4-(3-((2-(pyrrolidin-1-yl)-6-(trifluoromethyl)pyridin-3-yl)methyl)ureido)benzyl)methanesulfonamide;

53 N-(2-methyl-4-(3-((2-(4-methylpiperidin-1-yl)-6-(trifluoromethyl)pyridin-3-yl)methyl)ureido)benzyl)methanesulfonamide;

54 2-(4-(ethylsulfonamidomethyl)-3-fluorophenyl)-N-((2-(pyrrolidin-1-yl)-6-(trifluoromethyl)pyridin-3-yl)methyl)propanamide;

55 2-(4-(ethylsulfonamidomethyl)-3-fluorophenyl)-N-((2-(4-methylpiperidin-1-yl)-6-(trifluoromethyl)pyridin-3-yl)methyl)propanamide;

56 1-{[2-pyrrolidin-1-yl-6-(trifluoromethyl)pyridin-3-yl]methyl}-3-{4-[(sulfamoylamino)methyl]phenyl}propanamide;

57 1-{[2-pyrrolidin-1-yl-6-(trifluoromethyl)pyridin-3-yl]methyl}-3-{4-[(sulfamoylamino)methyl]phenyl}urea;

58 N-((2-(4-methylpiperidin-1-yl)-6-(trifluoromethyl)pyridin-3-yl)methyl)-2-(4-((sulfamoylamino)methyl)phenyl)propanamide;

59 1-{[2-(4-methylpiperidin-1-yl)-6-(trifluoromethyl)pyridin-3-yl]mnethyl}-3-{4-[(sulfamoylamino)methyl]phenyl}urea;

60 1-{3-fluoro-4-[(sulfamoylamino)methyl]phenyl}-3-{[2-pyrrolidin-1-yl-6-(trifluoromethyl)pyridin-3-yl]methyl}urea;

61 1-{3-fluoro-4-[(sulfamoylamino)methyl]phenyl}-3-{[2-(4-methylpiperidin-1-yl)1-6-(trifluoromethyl)pyridin-3-yl]methyl}urea;

62 2-(3-fluoro-4-((N-methylmethylsulfonamido)methyl)phenyl)-N-((2-(pyrrolidin-1-yl)-6-(trifluoromethyl)pyridin-3-yl)methyl)propanamide;

63 2-(3-fluoro-4-((N-methylmethylsulfonamido)methyl)phenyl)-N-((2-(4-methylpiperidin-1-yl)-6-(trifluoromethyl)pyridin-3-yl)methyl)propanamide;

64 2-(3-fluoro-4-((sulfamoylamino)methyl)phenyl)-N-((2-(4-methylpiperidin-1-yl)-6-(trifluoromethyl)pyridin-3-yl)methyl)propanamide;

65 N-(2-fluoro-5-(3-((2-(4-methylpiperidin-1-yl)-6-(trifluoromethyl)pyridin-3-yl)methyl)ureido)benzyl)methanesulfonamide;

66 2-(4-fluoro-3-(methylsulfonamidomethyl)phenyl)-N-((2-(4-methylpiperidin-1-yl)-6-(trifluoromethyl)pyridin-3-yl)methyl)propanamide;

67 N-((2-(piperidin-1-yl)-6-(trifluoromethyl)pyridin-3-yl)methyl)-2-(4-((sulfamoylamino)methyl)phenyl)propanamide;

68 2-(3-fluoro-4-((sulfamoylamino)methyl)phenyl)-N-((2-(piperidin-1-yl)-6-(trifluoromethyl)pyridin-3-yl)methyl)propanamide;

69 (S)—N-((2-(piperidin-1-yl)-6-(trifluoromethyl)pyridin-3-yl)methyl)-2-(4-((sulfamoylamino)methyl)phenyl)propanamide;

70 (R)—N-((2-(piperidin-1-yl)-6-(trifluoromethyl)pyridin-3-yl)methyl)-2-(4-((sulfamoylamino)methyl)phenyl)propanamide;

71 (S)-2-(3-fluoro-4-((sulfamoylamino)methyl)phenyl)-N-((2-(piperidin-1-yl)-6-(trifluoromethyl)pyridin-3-yl)methyl)propanamide; and 72 (R)-2-(3-fluoro-4-((sulfamoylamino)methyl)phenyl)-N-((2-(piperidin-1-yl)-6-(trifluoromethyl)pyridin-3-yl)methyl)propanamide, optionally in the form of a single stereoisomer or a mixture of stereoisomers, in the form of the free compound and/or a physiologically acceptable salt thereof.

13. A pharmaceutical composition comprising at least one substituted compound according to claim 1.

14. A method for treating a disorder or disease selected from the group consisting of pain; hyperalgesia; allodynia; causalgia; migraine; depression; nervous affection; an axonal injury; a neurodegenerative disease; a cognitive dysfunction; epilepsy; a respiratory disease; a cough; urinary incontinence; overactive bladder (OAB); a disorder and/or injury of the gastrointestinal tract; a duodenal ulcer; a gastric ulcer; irritable bowel syndrome; a stroke; an eye irritation; a skin irritation; a neurotic skin disease; an allergic skin disease; psoriasis; vitiligo; herpes simplex; an inflammation; diarrhoea; pruritus; osteoporosis; arthritis; osteoarthritis; a rheumatic disease; an eating disorder; medication dependency; misuse of medication; withdrawal symptoms in medication dependency; development of tolerance to medication; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects triggered by administration of a vanilloid receptor 1 agonist, comprising administering to a mammal an effective amount of at least one compound according to claim 1.

15. The method according to claim 14, wherein the pain is selected from the group consisting of acute pain, chronic pain, neuropathic pain, visceral pain and joint pain.

16. The method according to claim 14, wherein the neurodegenerative disease is selected from the group consisting of multiple sclerosis, Alzheimer's disease, Parkinson's disease and Huntington's disease.

17. The method according to claim 14, wherein the cognitive dysfunction is a cognitive deficiency state.

18. The method according to claim 17, wherein the cognitive dysfunction is a memory disorder.

19. The method according to claim 14, wherein the respiratory disease is selected from the group consisting of asthma, bronchitis and pulmonary inflammation.

20. The method according to claim 14, wherein the inflammation is an inflammation of the intestine, the eyes, the bladder, the skin or the nasal mucous membrane.

21. The method according to claim 14, wherein the eating disorder is selected from the group consisting of bulimia, cachexia, anorexia and obesity.

22. The method according to claim 14, wherein the development of tolerance to medication is the development of tolerance to natural or synthetic opioids.

23. The method according to claim 14, wherein the undesirable side effects are selected from the group consisting of hyperthermia, hypertension and bronchoconstriction and the vanilloid receptor 1 agonist is selected from the group consisting of capsaicin, resiniferatoxin, olvanil, arvanil, SDZ-249665, SDZ-249482, nuvanil and capsavanil.

* * * * *